US012705732B2

(12) United States Patent
Tscholl et al.

(10) Patent No.: US 12,705,732 B2
(45) Date of Patent: Aug. 11, 2026

(54) METHOD AND SYSTEM FOR DISPLAYING AND MONITORING A PATIENT'S BLOOD COAGULATION FUNCTION

(71) Applicant: Universität Zürich, Zürich (CH)

(72) Inventors: David W. Tscholl, Zollikon Dorf (CH); Christoph B. Noethiger, Oberwil-Lieli (CH); Donat R. Spahn, Zürich (CH)

(73) Assignee: UNIVERSITÄT ZÜRICH, Zurich (CH)

( * ) Notice: Subject to any disclaimer, the term of this patent is extended or adjusted under 35 U.S.C. 154(b) by 1112 days.

(21) Appl. No.: 17/651,692

(22) Filed: Feb. 18, 2022

(65) Prior Publication Data

US 2022/0172362 A1 Jun. 2, 2022

Related U.S. Application Data

(63) Continuation of application No. PCT/EP2020/073005, filed on Aug. 17, 2020.

(30) Foreign Application Priority Data

Aug. 22, 2019 (EP) .................................... 19193196

(51) Int. Cl.

| | |
|---|---|
| ***G06T 7/00*** | (2017.01) |
| ***A61B 5/0205*** | (2006.01) |
| ***A61B 5/024*** | (2006.01) |
| ***G06T 11/10*** | (2026.01) |
| ***G06T 15/00*** | (2011.01) |

(52) U.S. Cl.

CPC ............ *G06T 7/0012* (2013.01); *G06T 11/10* (2026.01); *G06T 15/00* (2013.01); *A61B 5/02055* (2013.01); *A61B 5/024* (2013.01); *G06T 2207/30104* (2013.01); *G06T 2215/16* (2013.01)

(58) Field of Classification Search

CPC ..... G06T 7/0012; G06T 11/001; G06T 15/00; G06T 2207/30104; G06T 2215/16; A61B 5/02055; A61B 5/024; G16H 50/50; G16B 5/30

See application file for complete search history.

(56) References Cited

PUBLICATIONS

Yazdanbod I and Marcus S. An Agent-Based Simulation of Blood Coagulation Processes. Journal of Undergraduate Research in Alberta 1: 13-18 (2011). Retrieved from: https://journalhosting.ucalgary.ca/index.php/jura/article/view/30037. (Year: 2011).*

Mu J, Liu X, Kamocka MM et al. Segmentation, Reconstruction, and Analysis of Blood Thrombus Formation in 3D 2-Photon Microscopy Images. EURASIP J. Adv. Signal Process. 2010: 147216 (2009). DOI: https://doi.org/10.1155/2010/147216. (Year: 2009).*

Schmid B, Tripal P, Fraaß T et al. 3Dscript: Animating 3D/4D microscopy data using a natural-language-based syntax. Nat Methods 16: 278-280 (2019). DOI: https://doi.org/10.1038/s41592-019-0359-1. (Year: 2019).*

J. Benes et al.: "Viscoelastic Methods of Blood Clotting Assessment—A Multidisciplinary Review", Frontiers in Medicine; vol. 2, Article 62; www.frontiersin.org; Sep. 14, 2015, 9 pages.

R. Lakshmanan et al.: "Smartphone-Based Optical System for Blood Coagulation Self-Monitoring", Biomedical Diagnostics Institute, Dublin City University, Dublin Ireland; Apr. 1, 2016, 7 pages.

S. Nayak et al.: "Using a Systems Pharmacology Model of the Blood Coagulation Network to Predict the Effects of Various Therapies on Biomarkers", CPT Pharmacometrics Systems Pharmacology; vol. 4, No. 7; Jun. 19, 2015, pp. 396-405.

S. Yesudasan et al.: "Recent Advances in Computational Modeling of Thrombosis Machine Learning for Molecular Dynamics View Project", School of Chemical, Materials and Biomedical Engineering, University of Georgia; Jan. 1, 2018, 16 pages.

* cited by examiner

*Primary Examiner* — Lori A. Clow
*Assistant Examiner* — Diana P Sanford
(74) *Attorney, Agent, or Firm* — Brake Hughes Bellermann LLP

(57) ABSTRACT

Multiple streams of raw blood coagulation function data may be synthesized into a single display or instrument, showing a synthetic model of a blood clot, which is generated according to algorithms and rendered dynamically in real time by a graphics processor. Dynamic alterations in the states or attributes of specified parts of a displayed blood clot may be used. The dynamic alterations involve, but are not limited to, the shape of parts, changes in the volume of parts, in a three-dimensional representation, or the area of parts, in a two-dimensional representation, number and movement of parts, and changes in the color of parts. The blood clot may be looked at from all angles according to user input. The dynamically altered parts of the visual clot model may include background, drug indicator, fibrin mesh indicator, plasmatic coagulation factor indicator, blood drops and pool of blood indicator, and platelet indicator.

17 Claims, 37 Drawing Sheets

Plasmatic drug level

Patient laboratory blood test results

Viscoelastic test output

Patient monitoring vital signs

Patient diagnoses and characteristics parameter value number of drug indicators

25

25

A

A

METHOD AND SYSTEM FOR DISPLAYING AND MONITORING A PATIENT'S BLOOD COAGULATION FUNCTION

CROSS REFERENCE TO RELATED APPLICATIONS

This application claims priority to, and is a continuation of PCT/EP2020/073005, filed on Aug. 17, 2020 and entitled "METHOD AND SYSTEM FOR DISPLAYING AND MONITORING A PATIENT'S BLOOD COAGULATION FUNCTION," which in turn claims priority to EP Application No. 19193196.3 filed on Aug. 22, 2019, both of which are hereby incorporated by reference in their entireties.

TECHNICAL FIELD

The present description in general is directed to the field of monitoring the clinical state of a patient, and more in particular relates to an appropriate synthesis of coagulation system monitoring information for a health care provider or another user of a blood coagulation monitoring device, e.g., a personal consumer using an e-health app.

BACKGROUND

Contemporary health care settings such as intensive care units, operating rooms, hospital wards, and doctors' offices make extensive use of devices measuring or displaying blood coagulation function data. These devices are used for diagnosing bleeding disorders, for measuring the response to drug therapy, for evaluating perioperative hemostasis and in transfusion medicine. Furthermore, blood coagulation function data is being used and displayed in telemedicine products, online and offline hardware and software applications, and a broad scope of consumer health products, e.g., e-health applications for smart devices, for use at home or in retirement homes. A contemporary blood coagulation monitoring system may display thirty or more different raw coagulation function data points and geometrical forms on a single screen. However, the number of data points displayed is huge and overwhelms users with information. With a growing number of parameters monitored, it quickly becomes impossible to consistently comprehend all of the information and remain aware of the patient's blood coagulation situation. However, the correct and rapid understanding of a patient's blood coagulation situation by the attending physician is vital for the patient. Only with a correct understanding and a high level of certainty that the diagnosis is correct can a doctor quickly administer the right medication to correct blood coagulation.

SUMMARY

One solution to this information complexity problem is a computer-generated instrument, i.e., a graphical display, synthesizing the raw coagulation system function data into a single dynamic two- or three-dimensional synthetic blood clot model, representing the condition of the monitored patient's blood coagulation according to the raw data input. Compared to a conventional monitoring device, a computer-generated user interface generated by described embodiments can be read and understood by healthcare providers and personal consumers much more easily; a significant advantage when they must make quick decisions under stress. For this purpose, a visual blood clot model is created from data received from blood coagulation monitoring devices, or hospital information systems, or data stored in a relational database, or from other methods that come to the mind of those skilled in the art.

A computer-implemented method, a corresponding computer program product and a system is provided for rendering an image of a two- or three-dimensional graphic of a synthetic blood clot model for display either as addition to a monitoring device, incorporated within a conventional patient monitoring device, or as a hologram.

In one embodiment, all monitoring information is presented in a single, easy-to-understand instrument, which is dynamically rendered and shown on a display device. It may be presented in a wearable electronic device such as a smartwatch or augmented reality device, or as a hologram or virtual hologram. The display in accordance with an embodiment may be two or three-dimensional. The visual clot model may be presented: A: as a separate standalone device in addition to a state-of-the-art blood coagulation monitoring system; B: integrated with a conventional blood coagulation monitoring device (single monitor showing both the visual clot instrument and conventional monitoring parameters); C: projected as a hologram. A blood sample is taken from a patient and inserted into a device performing blood coagulation function measurement with patient's blood. The resulting coagulation function data may be presented in alphanumeric form, or in geometrical form, e.g., viscoelastic test result, platelet function test result. The visual clot model may be displayed on a separate display device or integrated in a display device together with the alphanumeric coagulation function data, or it may be projected as a hologram.

A blood clot is altered according to raw coagulation function data inputs, including, but not limited to: standard laboratory blood analyses, e.g., hemoglobin concentration, thrombocyte count, individual plasmatic factor function data, e.g., fibrinogen concentration, factor V (five) function, factor XIII (thirteen) function, international normalized ratio and quick-value, activated partial thromboplastin time, drug specific anti-factor-ten-a-activity, specific plasmatic levels of drugs affecting coagulation, e.g., rivaroxaban plasma level, thrombocyte function tests, e.g., light transmission aggregometry and viscoelastic tests, e.g., clotting time, r time maximum clot firmness, maximum amplitude, maximum lysis. To render the image, the raw data is organized and processed according to algorithms and sent to the graphics processor for rendering. In one embodiment, a computer-implemented method creates an instrument showing a synthetic rendering of a blood clot model according to the raw data input representing the state of a patient's blood coagulation. The method uses alterations of the attributes of specified parts of a blood clot model, including the presence or absence of parts, volume and area of parts, number of parts, and color of parts. According to the algorithms incorporated into the system, the inputs of the individual raw monitoring data for each parameter cause alterations of the attributes of one or more parts of the blood clot model. The method also proportions the extent of change of the parts of the blood clot model according to the data input and the algorithms. The required changes of the attributes of the parts of the visual clot representation are forwarded to a graphics processor for rendering as a two- or three-dimensional image. The features of described embodiments are hereinafter fully described and particularly pointed out in the following descriptions, the annexed drawings, and the claims, setting forth in detail one or more illustrative embodiments. These being indicative, however, of but one or a few of various ways in which the principles underlying the various embodiments can be employed.

BRIEF DESCRIPTION OF THE DRAWINGS

FIG. 5: A schematic overview of the allocation of the data points to parts of the blood clot model according to one embodiment of the.

DETAILED DESCRIPTION

Figure 1:
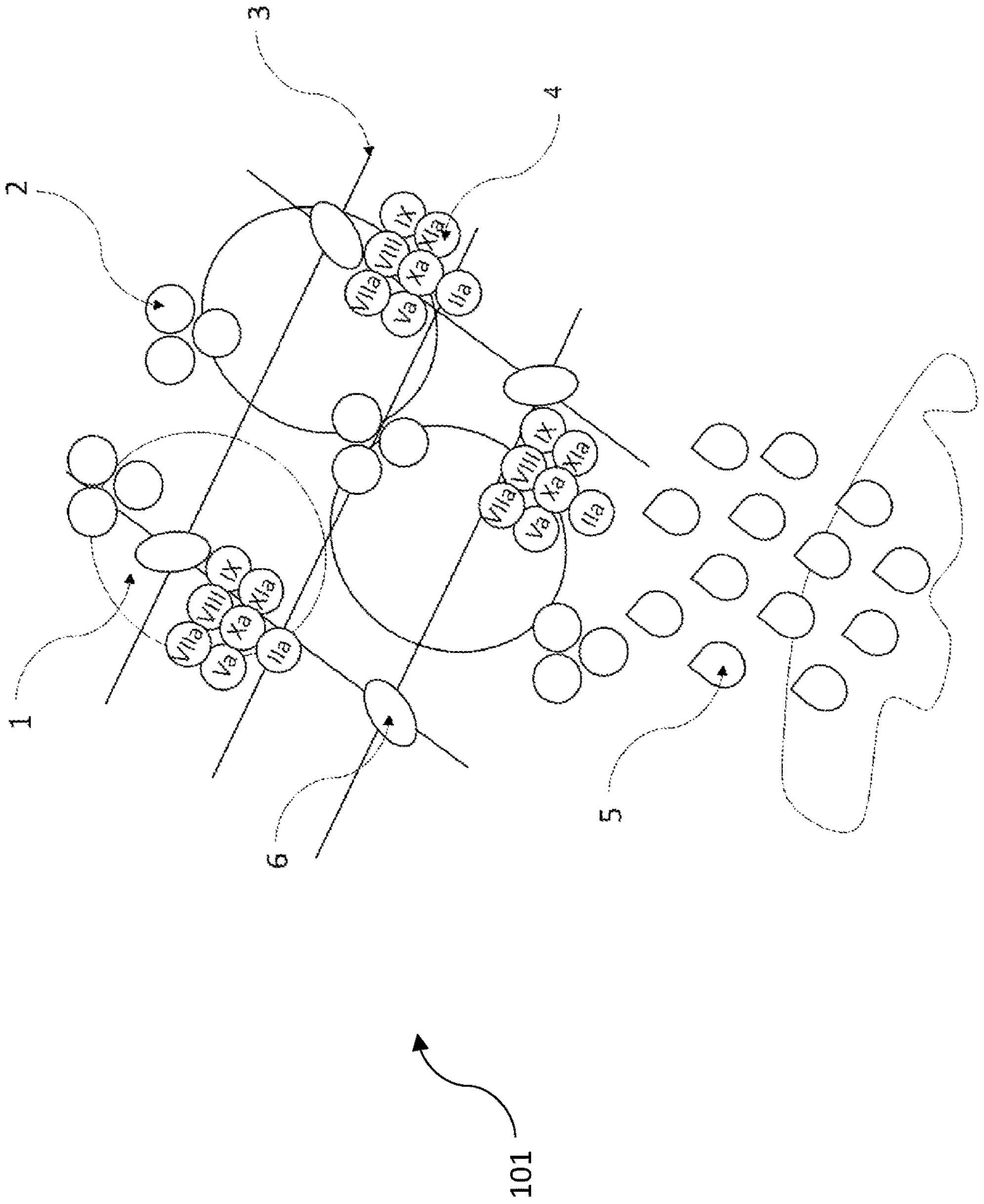
FIG. 1: basic design of a blood clot model and parts that are altered according to an example embodiment.

FIG. 1 illustrates a basic design example of a blood clot model 101 with the parts that are altered according to example embodiments. The dynamic alterations of the characteristics of the parts of the blood clot include, but are not limited to, their presence or absence, as well as changes in number, volume, area, and color of parts. The blood clot may be looked at from all angles according to user input. The dynamically altered parts of the visual clot model in the example model include background (1), drug indicator (2), fibrin mesh indicator (3), plasmatic coagulation factor indicator (4), blood drops and pool of blood indicator (5), and platelet indicator (6).

Figure 2:
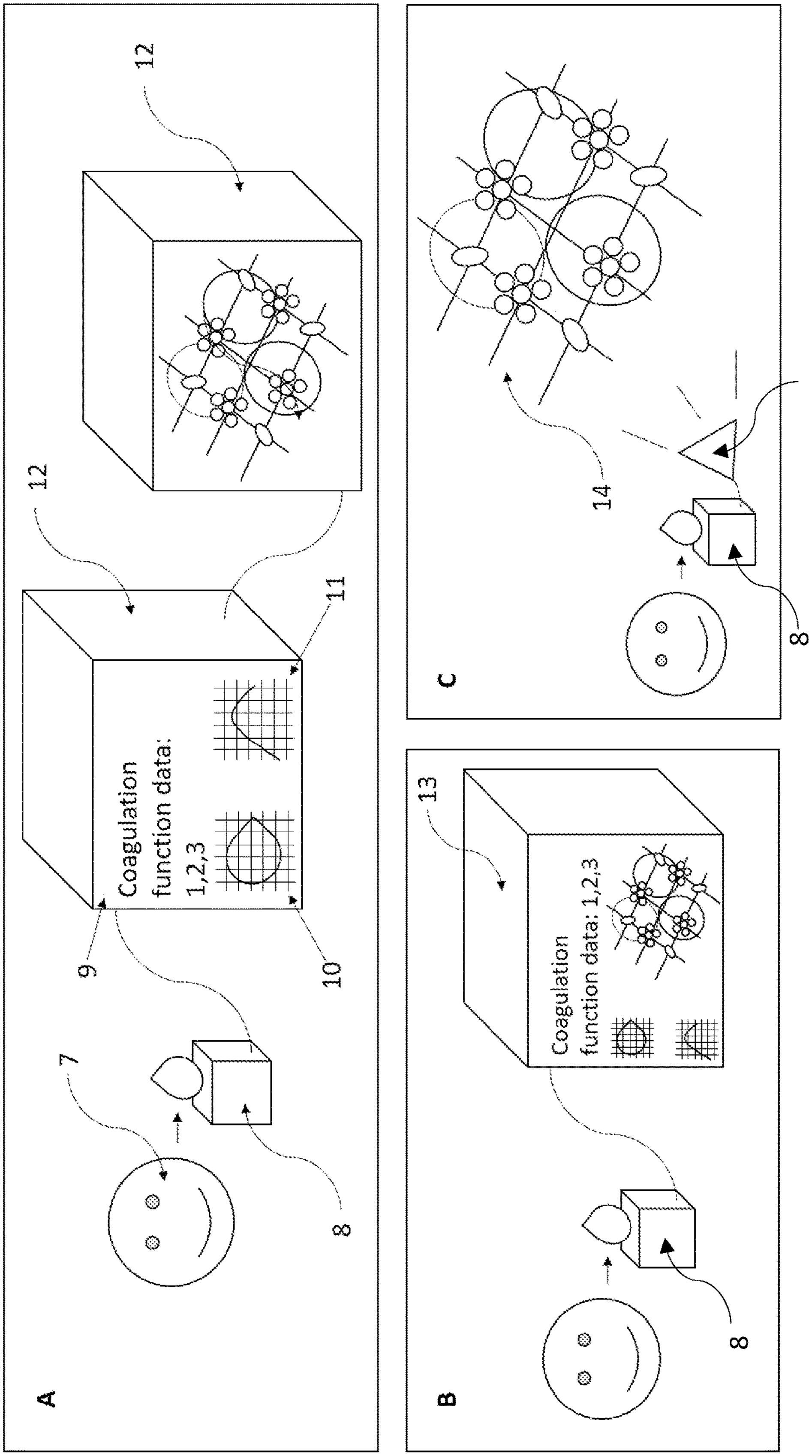
FIG. 2: Various visual clot model representations.

FIG. 2 illustrates various visual clot model representations 12, 13, 14 as presented to a user 7 with respect to a blood sample 8 of a patient, including:

- section A: as a separate standalone device 12 in addition to a state-of-the-art blood coagulation monitoring system 9 with respective user interface elements 10, 11;
- section B: integrated with a conventional blood coagulation monitoring device (single monitor 13 showing both the visual clot instrument and conventional monitoring parameters);
- section C: projected as a hologram 14 by an appropriate hologram projector 14-1.

The disclosed concept is particularly suited to be used integrated with a conventional blood coagulation monitoring device, i.e., a single screen showing both the visual clot instrument and raw conventional numerical or geometrical coagulation function data, as shown in FIG. 2 section B 13. However, it may also be used as a secondary separate instrument shown on a separate display, in addition to a primary patient monitoring device, as shown in FIG. 2 section A 12. The display device may be, for example, a cathode ray tube, a liquid crystal display screen, a gas plasma-based flat-panel display, an organic light-emitting diode display, an augmented reality device such as a head-mounted display, e.g. virtual reality headset, eyeglasses, contact lenses or any other form of augmented reality device. Furthermore, the visualization may be presented on a computerized wristwatch (smart watch), as a hologram, as shown in FIG. 2 section C 14, or other devices suitable for display of the instrument.

Example embodiments provide for the creation of a two- or three-dimensional instrument from the synthesis of raw conventional numerical or geometrical coagulation function data. According to the raw monitoring data, an example embodiment creates a blood clot model 101, which is a synthetic representation of the condition of the actual monitored patient's coagulation function. A graphics processor dynamically renders the image.

Figure 3:
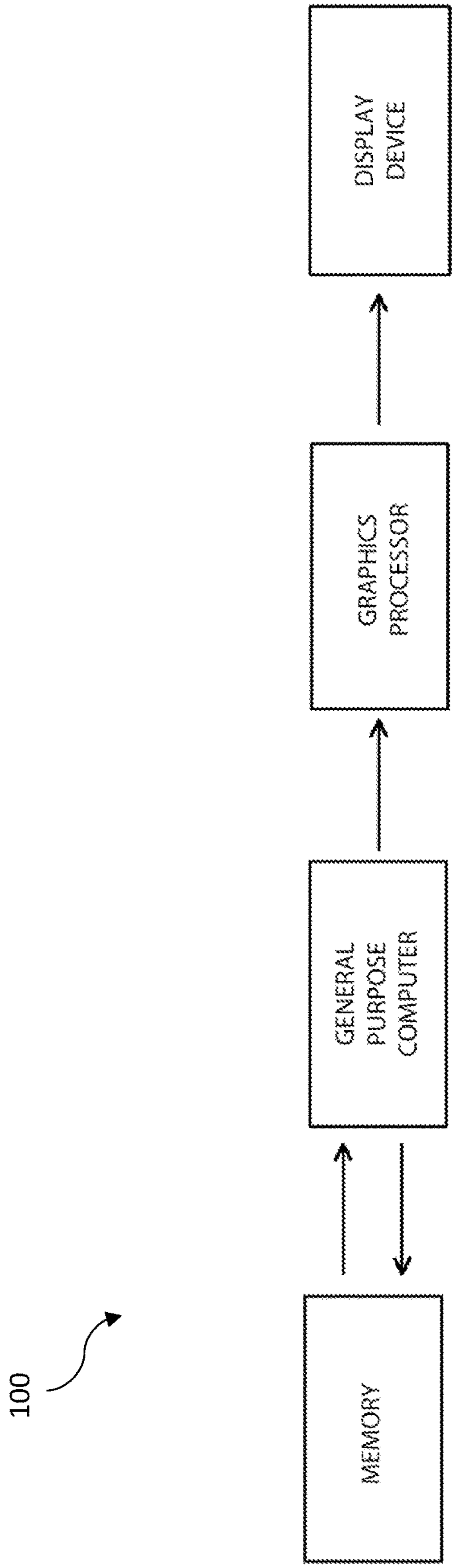
FIG. 3: A schematic overview of the computer system according to an embodiment.

An overview of a computer system 100 for carrying out the computer-implemented method in accordance with an embodiment is shown schematically in FIG. 3. The system 100 includes a computer, which may be a general purpose computer or a dedicated, specially designed computer, the memory containing the software code with the algorithms, a graphics processor, and a display device.

Figure 4:
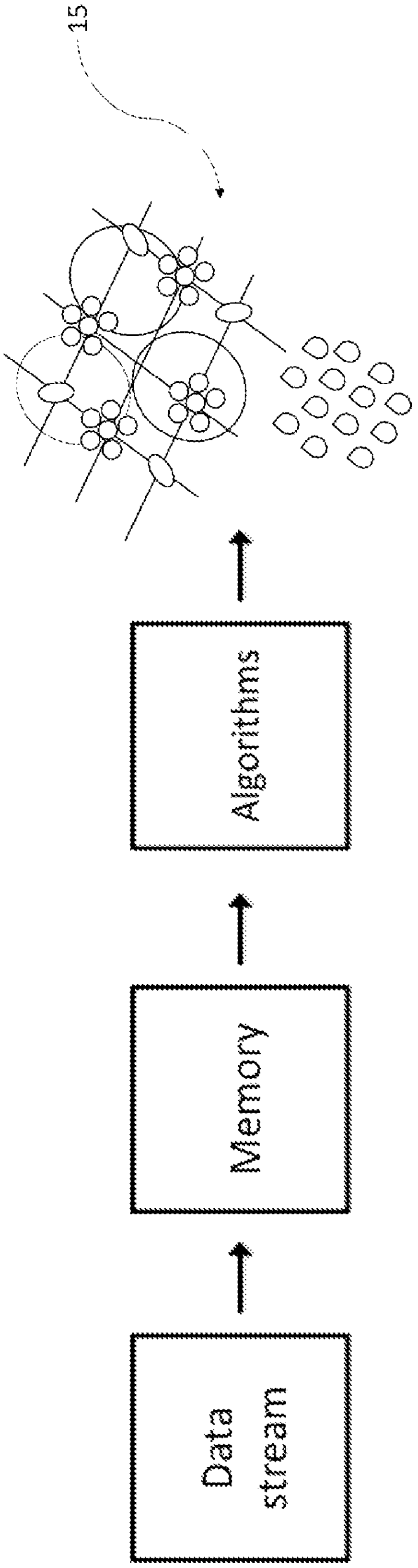
FIG. 4: The visual clot algorithm: A schematic overview of the process of creating an instrument showing an appropriate synthesis of blood coagulation function monitoring data according to an embodiment.

The process of rendering an instrument, i.e., the visual clot model (15) from the raw conventional numerical or geometrical coagulation function data, according to an example embodiment, takes place in two broad steps, which are detailed hereafter and outlined in FIG. 4.

In step 1 the raw input data (i.e., "Data stream" in FIG. 4) is loaded into system memory (i.e., "Memory" in FIG. 4) and is transformed by the general purpose computer into data points, which can be utilized for further processing. The raw conventional numerical or geometrical coagulation function data may come from commercially or otherwise available devices, e.g. a blood coagulation measurement device, or a relational database which stores such measurement data. A stream of raw conventional numerical or geometrical coagulation function data are loaded into memory and transformed by algorithms so that each data point can be utilized directly by the example embodiment. This data stream may contain, but is not limited to, any one of the following parameters: hemoglobin concentration, thrombocyte count, individual plasmatic factor function, international normalized ratio and quick-value, activated partial thromboplastin time, drug-specific anti-factor-ten-a-activity, specific plasmatic drug level, thrombocyte function test output variables, viscoelastic test output variables and all other output variables of coagulation function test.

This generation of data points is continuously repeated as data is retrieved from the coagulation monitoring device or software. The resulting data points are a representation of each coagulation function parameter. If the raw data from a coagulation device is processed on-site, it is loaded directly into the memory. If it is delivered from a remote coagulation function monitoring device, an additional data store is prepared as required.

Figure 5:
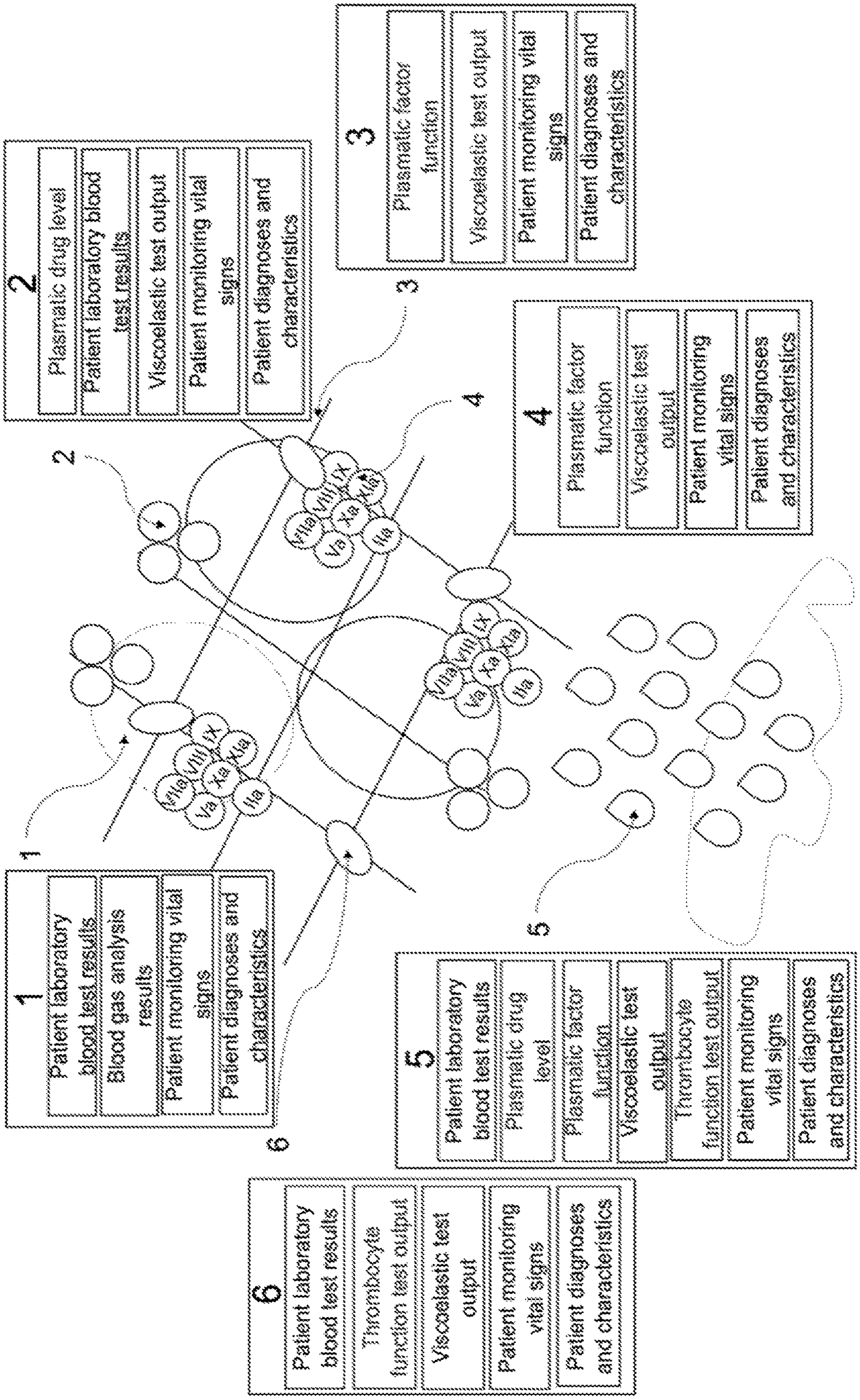

In step 2, the data points are transformed by the general purpose computer according to the algorithms of the various example embodiments, i.e., "ALGORITHMS" in FIG. 4, into one or multiple alterations in the states of specified parts 15 of a blood clot model 101. The computer-implemented method according to an example uses changes in the attributes of specified parts of a blood clot model 101. These alterations (i.e., "ALTERATIONS" in FIG. 4) include the presence and absence of parts, the volume and area of parts, the number of parts, the color of parts and the movement of parts of the blood clot model 101. The graphics processor renders the image on a display device, i.e., the parts of the clot model are changed dynamically, according to the pertinent information. In order to establish data to render the image on the display, data points are allocated to one or more representative parts of the blood clot model 101 (FIG. 5). A schematic overview of the allocation of the data points to parts of the blood clot model 101 according to one example embodiment is provided with respect to Part 1: background (showing blood cells in the graphical example of a preferred embodiment). (1), part 2: drug indicator (2), part 3: fibrin mesh indicator (3), part 4: plasmatic coagulation factor indicator (4), part 5: blood drop and pool of blood indicator (5), part 6: platelet indicator (showing non activated thrombocytes in the graphical example) (6). This assignment of coagulation function measurements and parameters represents only one of many possible assignments, according to an example embodiment. Experts in the field of blood coagulation function may come up with many other possible assignments. However, other assignments would not deviate from the scope of the description.

While one process of selecting one or more specific parts of the visual clot model for each data point has been disclosed, others are possible and other methods of assigning data points to parts of the visual clot model will occur to those skilled in the art and may be used in applications without varying from the scope of this description.

According to an example embodiment, the rendering of the real-time instrument, showing the visual clot model takes place following the subroutines outlined hereafter (i.e., subroutines A and B).

Figure 6:
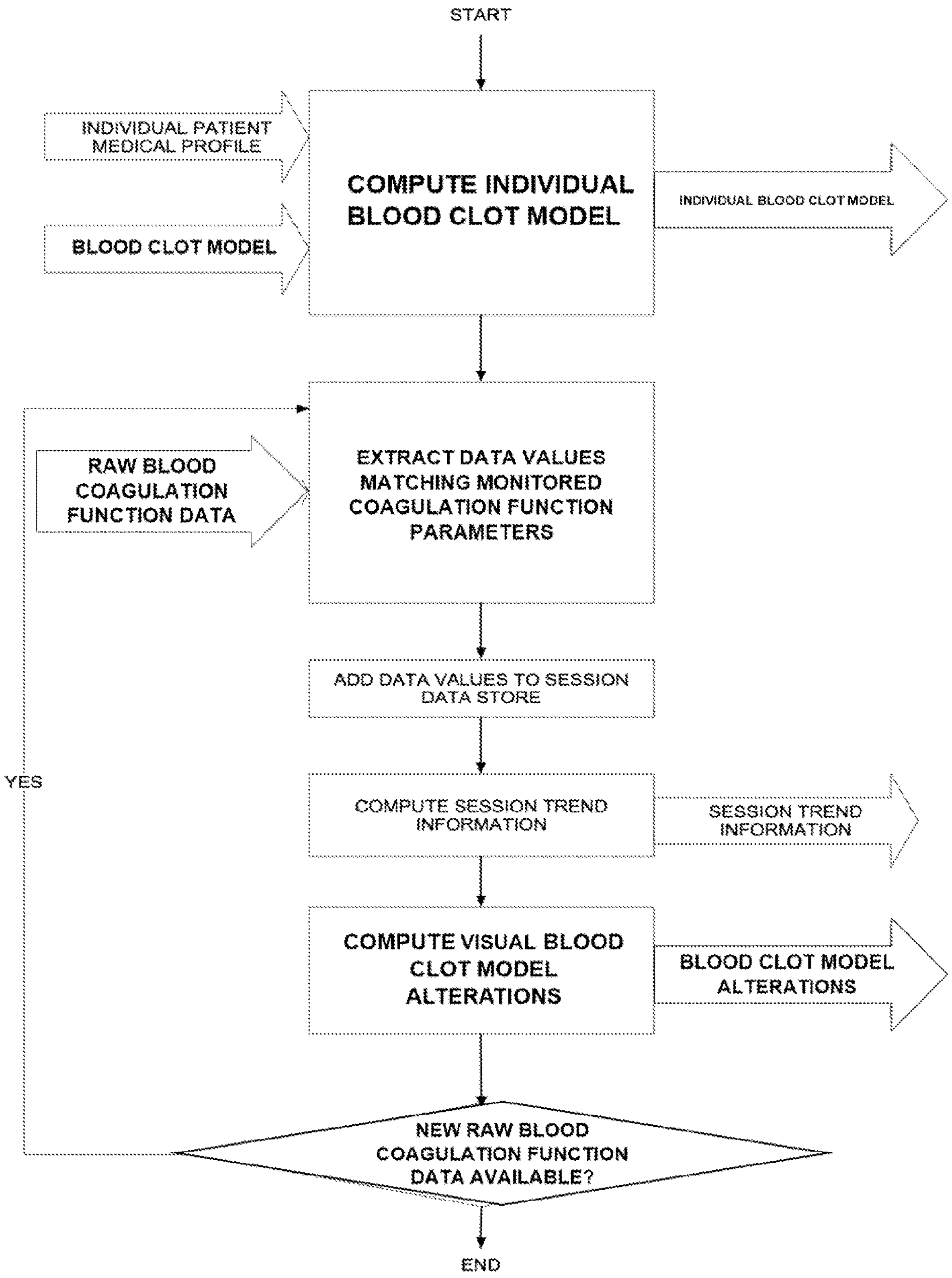
FIG. 6: showing a flow diagram of a first subroutine illustrating the procedure of generating an individual visual blood clot model, session trend information, and visual blood clot model animations.

FIG. 6 shows a flow diagram of a first subroutine A illustrating the procedure of generating an individual blood clot model 101 (i.e., a blood clot model tailored to the coagulation function parameters of an individual patient), session trend information, and visual blood clot model 101 animations according to data from the individual patient medical profile, the default visual blood clot model 101, and the raw blood coagulation function parameters data stream. Session trend information provides data representing the monitoring session history (data which were recorded during a monitoring session for a patient).

Figure 7:
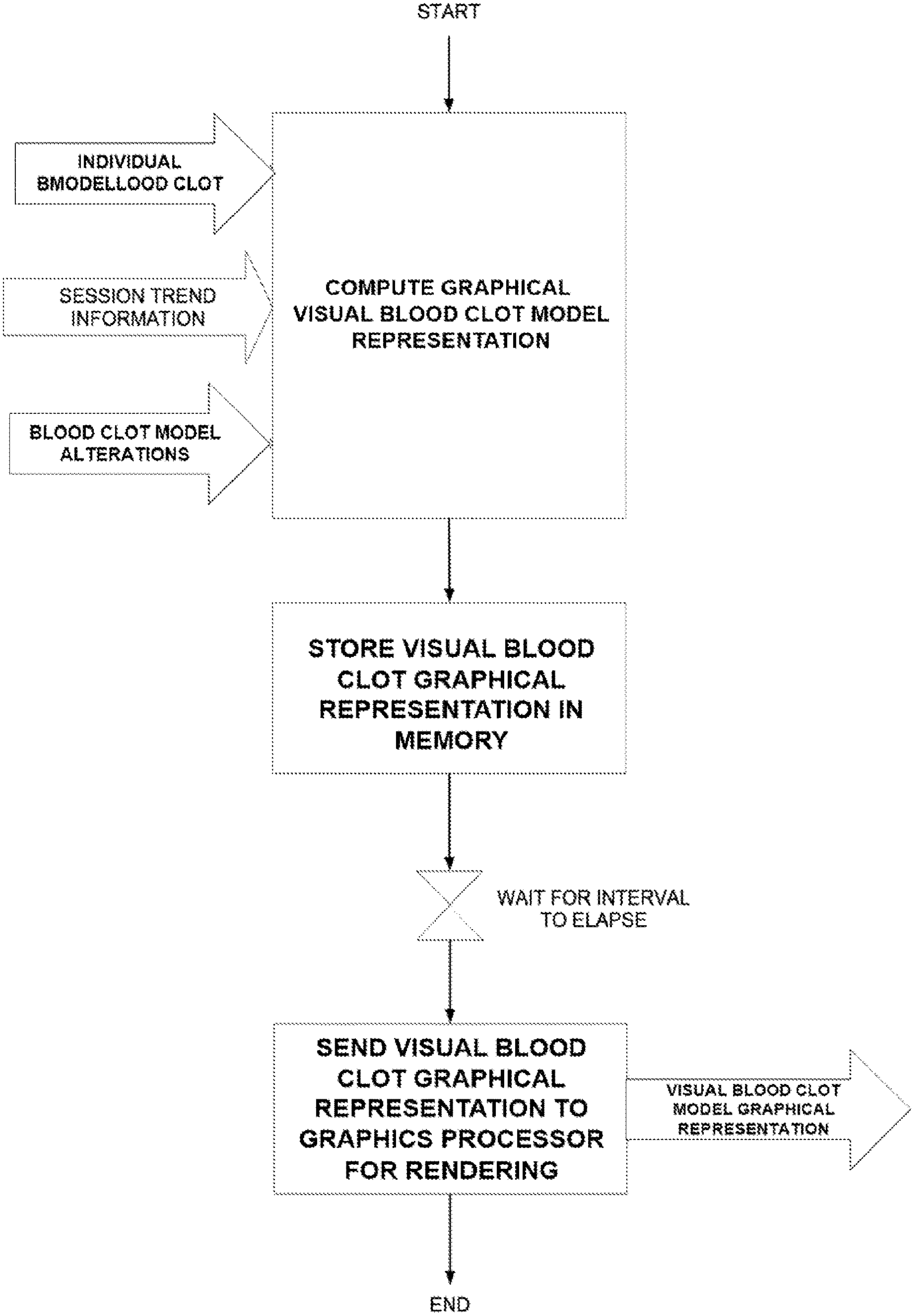
FIG. 7: showing a flow diagram of a second subroutine of a visual blood clot overall algorithm according to an embodiment.

FIG. 7 shows a flow diagram of a second subroutine B of the visual blood clot overall algorithm (cf. FIG. 4) according to an embodiment. Thereby, subroutine A fills a data buffer in memory that is loaded and consumed by subroutine B for further processing. In detail, the two- or three-dimensional blood clot model 101 is computed ("COMPUTE VISUAL BLOOD CLOT GRAPHICAL MODEL REPRESENTATION") by using the individualized visual blood clot model 101 (i.e., the customized blood clot avatar), session trend information (i.e., the monitoring session history), and the model animations to be performed in the individual visual blood clot model 101.

While subroutine A (cf. FIG. 6) generates input data for subroutine B (cf. FIG. 7), they may be executed autonomously. In detail, subroutine A may generate data and temporarily store it in a data buffer until subroutine B consumes the data for further processing. Both subroutine A and subroutine B are connected through the overall visual patient monitoring algorithm (cf. FIG. 4).

Subroutine A starts by computing an individual visual blood clot model based on the patient's medical profile (i.e., age, weight, gender, height, pediatric, medical conditions, e.g. obesity) by altering a default blood clot model creating a "customized blood clot avatar". The outcome (depicted as "INDIVIDUAL VISUAL BLOOD CLOT MODEL" in FIG. 6) of this procedure (depicted as "COMPUTE INDIVIDUAL VISUAL BLOOD CLOT MODEL" in FIG. 6) is used as an input for subroutine B (FIG. 7) of the algorithm.

After the individual blood clot model has been established, the next step is to handle the incoming patient monitoring data. In case blood coagulation function data arrives in form of a data stream ("RAW BLOOD COAGULATION FUNCTION DATA STREAM" in FIG. 6), data points that match the monitored blood coagulation function parameters are extracted from the data stream, loaded into memory and transformed into data points, as described in step one above. Then, these data points are associated with the current timestamp and added to the session data store (i.e., a storage medium containing the saved monitoring session data) ("ADD DATA POINTS TO SESSION DATA STORE" in FIG. 6) so that session trend information (i.e., the monitoring session history) can be computed in a subsequent step ("COMPUTE SESSION TREND INFORMATION" in FIG. 6). Furthermore, session trend information is used as an input for subroutine B (FIG. 7) of the algorithm and may be represented on the display.

Next, the computer takes the available individual data points (i.e., the patient's blood coagulation function parameters) and supplies them to the specific algorithms. Subsequently, these algorithms compute the state of each part of the visual blood clot model 101 ("COMPUTE INDIVIDUAL VISUAL BLOOD CLOT MODEL ALTERATIONS" in FIG. 6). The individual algorithms are described in detail in the section "DESCRIPTION OF ALGORITHMS". Once the individual animations have been computed, they are passed to subroutine B (FIG. 7) of the overall visual blood clot algorithm.

Furthermore, when new blood coagulation function data becomes available, the process starting from "EXTRACT DATA POINTS MATCHING MONITORED BLOOD COAGULATION PARAMETERS" in FIG. 6 is repeated until any more data can be extracted from the data stream.

FIG. 7 represents subroutine B of the visual blood clot overall algorithm (FIG. 4) according to a preferred embodiment, in which subroutine A fills a data buffer in memory that is loaded and consumed by subroutine B for further processing. In detail, the two- or three-dimensional blood clot model 101 is computed ("COMPUTE VISUAL BLOOD CLOT GRAPHICAL MODEL REPRESENTATION" in FIG. 7) by using the individualized visual blood clot model 101 (i.e., the customized blood clot avatar), session trend information (i.e., the monitoring session history), and the model animations to be performed in the individual visual blood clot model 101.

Once the two- or three-dimensional representation of the visual blood clot model 101 has been established, it is stored in memory ("STORE VISUAL BLOOD CLOT GRAPHICAL MODEL REPRESENTATION IN MEMORY") for later rendering by the graphics processor. In order to accommodate existing hardware limitations as imposed by the graphics processor, data stream, general purpose computer, or other involved components, the next step is to wait for a specific interval to be elapsed ("WAIT FOR INTERVAL TO ELAPSE" in FIG. 7) before sending the two- or three-dimensional model representation ("VISUAL BLOOD CLOT MODEL GRAPHICAL REPRESENTATION" in FIG. 7) to the graphics processor for rendering purposes (SEND VISUAL BLOOD CLOT GRAPHICAL REPRESENTATION TO GRAPHICS PROCESSOR FOR RENDERING). Hence, the latter timespan, which is pre- or dynamically determined, represents the sequence of image change by the display device (i.e., the display refresh rate). Subroutine B is repeated as long as data is present in the data buffer filled by subroutine A.

Computer readable instructions of a computer program product, which when loaded into a memory and executed by one or more processors of a computer system, cause the computer system to carry out the computer implemented method in accordance with an example embodiment. Such instructions may be stored in any recordable medium such as a hard drive, magnetically recordable tape, a compact disk, or as written instructions on paper. They may be stored in the memory (i.e., MEMORY in FIG. 4). The memory may include both volatile and nonvolatile memory components. Volatile components are those that do not retain data upon loss of power. Nonvolatile components are those that retain data upon a loss of power.

Thus, the memory may comprise, for example, random access memory (RAM), read-only memory (ROM), hard disk drives, solid state drives and/or other memory components, or a combination of any two or more of these memory components. The RAM may comprise, for example, static random access memory (SRAM), dynamic random access memory (DRAM), or magnetic random access memory (MRAM), non-volatile random-access memory (NVRAM), and other forms of memory. The ROM may comprise, for example, a programmable read-only memory (PROM), an erasable programmable read-only memory (EPROM), an electrically erasable programmable read-only memory (EEPROM), compact flash memory, or other like memory device.

DESCRIPTION OF ALGORITHMS

TABLE 1

This table outlines the parts of the visual blood clot model 101 that are affected by data points, and the attributes of the parts, which are altered according to algorithms 1-30 described in the following. According to an example embodiment, the algorithms use the inputs described in this table. However, the algorithms are not limited to the disclosed algorithms or by the disclosed algorithms, as persons skilled in the art may think of additional inputs without departing from the scope of the claimed description.

| Part within visual blood clot model | Affected by data points: | Changed attributes: | Name of algorithm |
|---|---|---|---|
| Part 1 (Blood cell and Background indicator) | Patient laboratory blood test results. For example, but not limited to: hemoglobin concentration, red and white blood cell parameters (e.g., cell count), c-reactive protein, transferrin saturation. | Volume of blood cells (3D) or area (2D). Form of blood cells. Number of blood cells displayed. Color of blood cells. Display of indicator labels. | Visual blood clot algorithms 1-5 |
| | Patient blood gas analysis results. For example, but not limited to: calcium ion concentration, pH. | Volume of blood cells (3D) or area (2D). Form of blood cells. Number of blood cells displayed. Color of blood cells. Display of indicator labels. | Visual blood clot algorithms 1-5 |
| | Patient monitoring vital signs. For example, but not limited to: body temperature, pulse rate. | Volume of blood cells (3D) or area (2D). Form of blood cells. Number of blood cells displayed. Color of blood cells. Display of indicator labels. | Visual blood clot algorithms 1-5 |
| | Patient diagnoses and characteristics, For example, but not limited to: anemia, sickle cell disease, von-Willebrandt disease. | Volume of blood cells (3D) or area (2D). Form of blood cells. Number of blood cells displayed. Color of blood cells. Display of indicator labels. | Visual blood clot algorithms 1-5 |
| Part 2 (Drug Indicator) | Plasmatic drug levels. For example, but not limited to: Edoxaban plasma levels. | Volume of drug indicator (3D) or area (2D). Form of drug indicator. Number of drug indicators displayed. Color of drug indicator. Display of indicator labels. | Visual blood clot algorithms 6-10 |

TABLE 1-continued

This table outlines the parts of the visual blood clot model 101 that are affected by data points, and the attributes of the parts, which are altered according to algorithms 1-30 described in the following. According to an example embodiment, the algorithms use the inputs described in this table. However, the algorithms are not limited to the disclosed algorithms or by the disclosed algorithms, as persons skilled in the art may think of additional inputs without departing from the scope of the claimed description.

| Part within visual blood clot model | Affected by data points: | Changed attributes: | Name of algorithm |
|---|---|---|---|
| | Patient laboratory blood test results. For example, but not limited to: specific Rivaroxaban anti-factor-ten-a activity, unspecific anti-factor-ten-a-activity. | Volume of drug indicator (3D) or area (2D). Form of drug indicator. Number of drug indicators displayed. Color of drug indicator. Display of indicator labels. | Visual blood clot algorithms 6-10 |
| | Viscoelastic test output. For example, but not limited to: difference in clotting time between ROTEM INTEM and HEPTEM channels. | Volume of drug indicator (3D) or area (2D). Form of drug indicator. Number of drug indicators displayed. Color of drug indicator. Display of indicator labels. | Visual blood clot algorithms 6-10 |
| | Patient monitoring vital signs. For example, but not limited to: body temperature, pulse rate. | Volume of drug indicator (3D) or area (2D). Form of drug indicator. Number of drug indicators displayed. Color of drug indicator. Display of indicator labels. | Visual blood clot algorithms 6-10 |
| Part 3 (Fibrin mesh indicator) | Plasmatic factor function. For example, but not limited to: factor 1 (fibrin) concentration, factor 13 (fibrin stabilizing factor). | Volume of fibrin mesh (3D) or area (2D). Form of fibrin mesh indicator. Number of fibrin mesh indicators displayed. Color of fibrin mesh indicator. Display of indicator labels. | Visual blood clot algorithms 11-15 |
| | Viscoelastic test output. For example, but not limited to: maximum clot firmness in ROTEM output. | Volume of fibrin mesh (3D) or area (2D). Form of fibrin mesh indicator. Number of fibrin mesh indicators displayed. Color of fibrin mesh indicator. Display of indicator labels. | Visual blood clot algorithms 11-15 |
| | Patient diagnoses and characteristics. For example, but not limited to: disseminated intravascular coagulation. | Volume of fibrin mesh (3D) or area (2D). Form of fibrin mesh indicator. Number of fibrin mesh indicators displayed. Color of fibrin mesh indicator. Display of indicator labels. | Visual blood clot algorithms 11-15 |
| | Patient laboratory blood test results. For example, but not limited to: low fibrinogen concentration in plasma. | Volume of fibrin mesh (3D) or area (2D). Form of fibrin mesh indicator. Number of fibrin mesh indicators displayed. Color of fibrin mesh indicator. Display of indicator labels. | Visual blood clot algorithms 11-15 |
| Part 4 (Plasmatic coagulation factor and co-factor indicator) | Plasmatic factor function For example, but not limited to: Coagulation Factor V, Factor XIII activity | Volume of plasmatic factor indicator (3D) or area (2D). Form of plasmatic factor indicator. Number of plasmatic factor indicators displayed. Color of plasmatic factor indicator. Display of plasmatic factor indicator labels. | Visual blood clot algorithms 16-20 |

TABLE 1-continued

This table outlines the parts of the visual blood clot model 101 that are affected by data points, and the attributes of the parts, which are altered according to algorithms 1-30 described in the following. According to an example embodiment, the algorithms use the inputs described in this table. However, the algorithms are not limited to the disclosed algorithms or by the disclosed algorithms, as persons skilled in the art may think of additional inputs without departing from the scope of the claimed description.

| Part within visual blood clot model | Affected by data points: | Changed attributes: | Name of algorithm |
|---|---|---|---|
| | Viscoelastic test output For example, but not limited to: Maximum Clot Firmness in ROTEM output | Volume of plasmatic factor indicator (3D) or area (2D). Form of plasmatic factor indicator. Number of plasmatic factor indicators displayed. Color of plasmatic factor indicator. Display of plasmatic factor indicator labels. | Visual blood clot algorithms 16-20 |
| Part 5 (Blood drops and pool of blood indicator) | Patient laboratory blood test results. For example, but not limited to: international normalized ratio, cell counts. | Volume of pool of blood drops and blood indicator (3D) or area (2D). Form of pool of blood drops and pool of blood indicator. Color of blood drops and pool of blood indicators. Number of blood drops displayed. Display of indicator labels. | Visual blood clot algorithms 21-25 |
| | Plasmatic drug levels. For example, but not limited to: Apixaban plasma level. | Volume of pool of blood drops and blood indicator (3D) or area (2D). Form of pool of blood drops and pool of blood indicator. Color of blood drops and pool of blood indicators. Number of blood drops displayed. Display of indicator labels. | Visual blood clot algorithms 21-25 |
| | Plasmatic factor function For example, but not limited to: Coagulation Factor VII (proconvertin) activity, Factor II (thrombin) activity | Volume of pool of blood drops and blood indicator (3D) or area (2D). Form of pool of blood drops and pool of blood indicator. Color of blood drops and pool of blood indicators. Number of blood drops displayed. Display of indicator labels. | Visual blood clot algorithms 21-25 |
| | Viscoelastic test output For example, but not limited to: Maximum lysis at 30 minutes in TEG output | Volume of pool of blood drops and blood indicator (3D) or area (2D). Form of pool of blood drops and pool of blood indicator. Color of blood drops and pool of blood indicators. Number of blood drops displayed. Display of indicator labels. | Visual blood clot algorithms 21-25 |
| | Thrombocyte function test output For example, but not limited to: Aspirin activity in Verify NOW System | Volume of pool of blood drops and blood indicator (3D) or area (2D). Form of pool of blood drops and pool of blood indicator. Color of blood drops and pool of blood indicators. Number of blood drops displayed. Display of indicator labels. | Visual blood clot algorithms 21-25 |

TABLE 1-continued

This table outlines the parts of the visual blood clot model 101 that are affected by data points, and the attributes of the parts, which are altered according to algorithms 1-30 described in the following. According to an example embodiment, the algorithms use the inputs described in this table. However, the algorithms are not limited to the disclosed algorithms or by the disclosed algorithms, as persons skilled in the art may think of additional inputs without departing from the scope of the claimed description.

| Part within visual blood clot model | Affected by data points: | Changed attributes: | Name of algorithm |
|---|---|---|---|
| Part 6 (Thrombocyte indicator) | Patient laboratory blood test results. For example, but not limited to: thrombocyte count. | Volume of thrombocyte indicator (3D) or area (2D). Form of thrombocyte indicator. Color of thrombocyte indicators. Number of thrombocyte indicator. Display of thrombocyte indicator. | Visual blood clot algorithms 26-30 |
| | Thrombocyte function test output For example, but not limited to: ADP test output in Multiplate System | Volume of thrombocyte indicator (3D) or area (2D). Form of thrombocyte indicator. Color of thrombocyte indicators. Number of thrombocyte indicator. Display of thrombocyte indicator. | Visual blood clot algorithms 26-30 |
| | Viscoelastic test output For example, but not limited to: MCF in ROTEM output | Volume of thrombocyte indicator (3D) or area (2D). Form of thrombocyte indicator. Color of thrombocyte indicators. Number of thrombocyte indicator. Display of thrombocyte indicator. | Visual blood clot algorithms 26-30 |

Visual Blood Clot Algorithm A1 (Volume [3D] and Area [2D] of Blood Cells) and Algorithm A2 (Form of Blood Cells)

These algorithms are used to make part 1 (FIG. 1) of the visual blood clot model (background) appear in an individualized way, which is modeled after and has logical commonality with the characteristics a blood clot would have in the real patient that the input data comes from. Algorithms A1 and A2 use the following inputs, however, are not limited to these or by these, as persons skilled in the art may think of additional inputs without departing from the scope of the description: Patient laboratory blood test results, blood gas analysis results, patient monitoring vital signs, patient diagnoses and characteristics.

Figure 8:
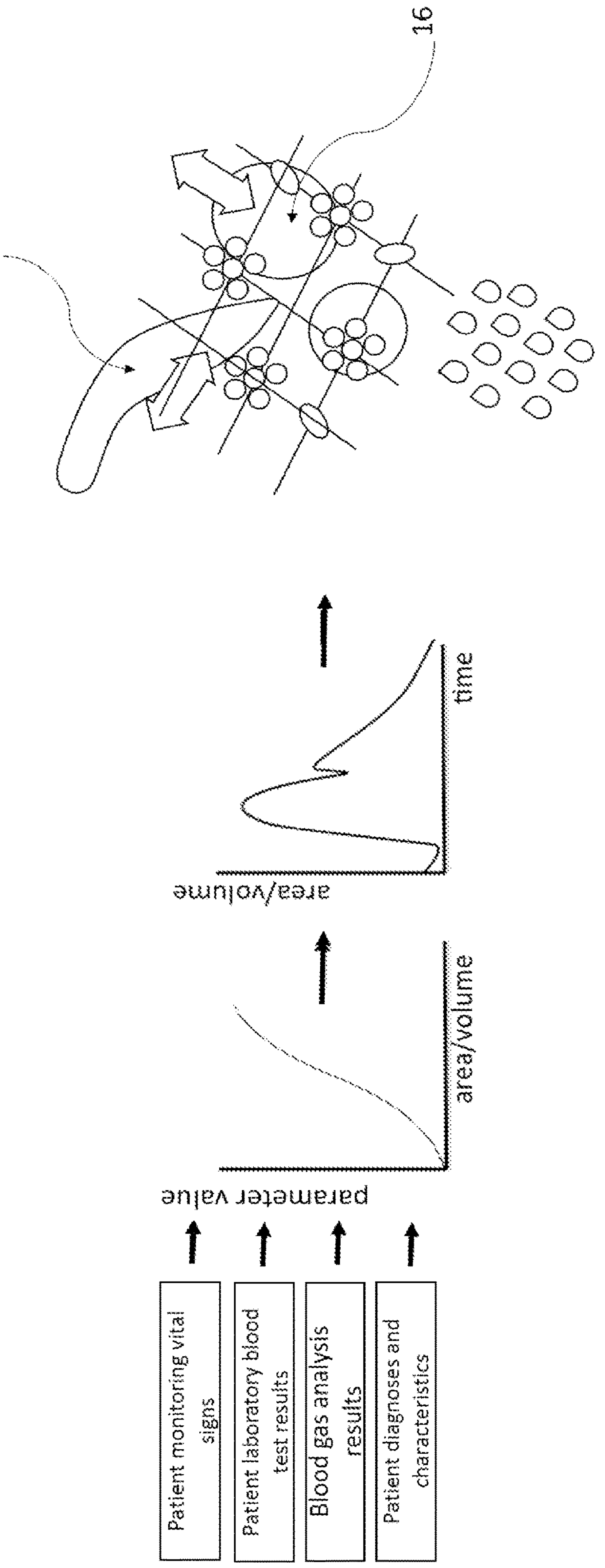
FIGS. 8 to 31: showing schematic overviews of the logic of various visual blood clot algorithms.

According to algorithms A1 and A2, changes in patient laboratory blood test results, blood gas analysis results, patient diagnoses and characteristics, and patient monitoring vital signs lead to a change in volume (3D) or area (2D) of the blood cells shown in the background of the visual blood clot model following an ease in ease out function. The ease in/out function causes very low and very high values of input coagulation function parameters to cause more extensive changes in volume or area of parts (3D) or area (2D) of blood cells compared to normal and less low and less high input parameter values. This function serves to enable users to detect low and high-extremes. FIG. 8 provides a schematic overview of these algorithms. Figure shows a schematic overview of the logic of the visual blood clot algorithm A1 and A2 with respective graphical examples: 1) The input "sickle cell disease" causes the algorithm to change the shape of the red blood cells shown in the background to the form of a sickle cell, and 2) The input: "high or low erythrocyte volume" causes the algorithm to change the volume (3D) or area (2D) of the blood cells. For specific pre-defined diagnoses and characteristics stored in memory, the algorithms create specific changes in volume (3D), area (2D), or form of blood cells, also stored in memory. Depending on specific vital sign values or patient characteristics, the blood cells or other background components can change their volume or area according to vital values, as for example, pulse rate or arterial pressure curve.

Examples: 1) The patient data management system input "blood loss" causes the algorithms to make the blood cells appear smaller. 2) The input: "high erythrocyte volume" (laboratory blood test result) causes the algorithms to make the blood cells 16 appear larger. 3) The input high plasma sodium concentration causes the blood cells to appear smaller. 4) The input sickle cell disease (patient diagnosis and characteristic input) causes the algorithms to change the shape of the red blood cells shown in the background to the form of a sickle cell 17.

Visual Blood Clot Algorithm A3 (Number of Blood Cells Displayed)

This algorithm is used to make part 1 (FIG. 1) of the visual blood clot model 101 (background) appear in an individualized way, which is modeled after and has logical commonality with, the characteristics a blood clot would have in the real patient that the input data comes from. Algorithm A3 uses the following inputs, however, is not limited to these or by these, as persons skilled in the art may think of additional inputs without departing from the scope of the description: laboratory blood test results, blood gas analysis results, patient diagnoses, characteristics, and patient monitoring vital signs.

Figure 9:
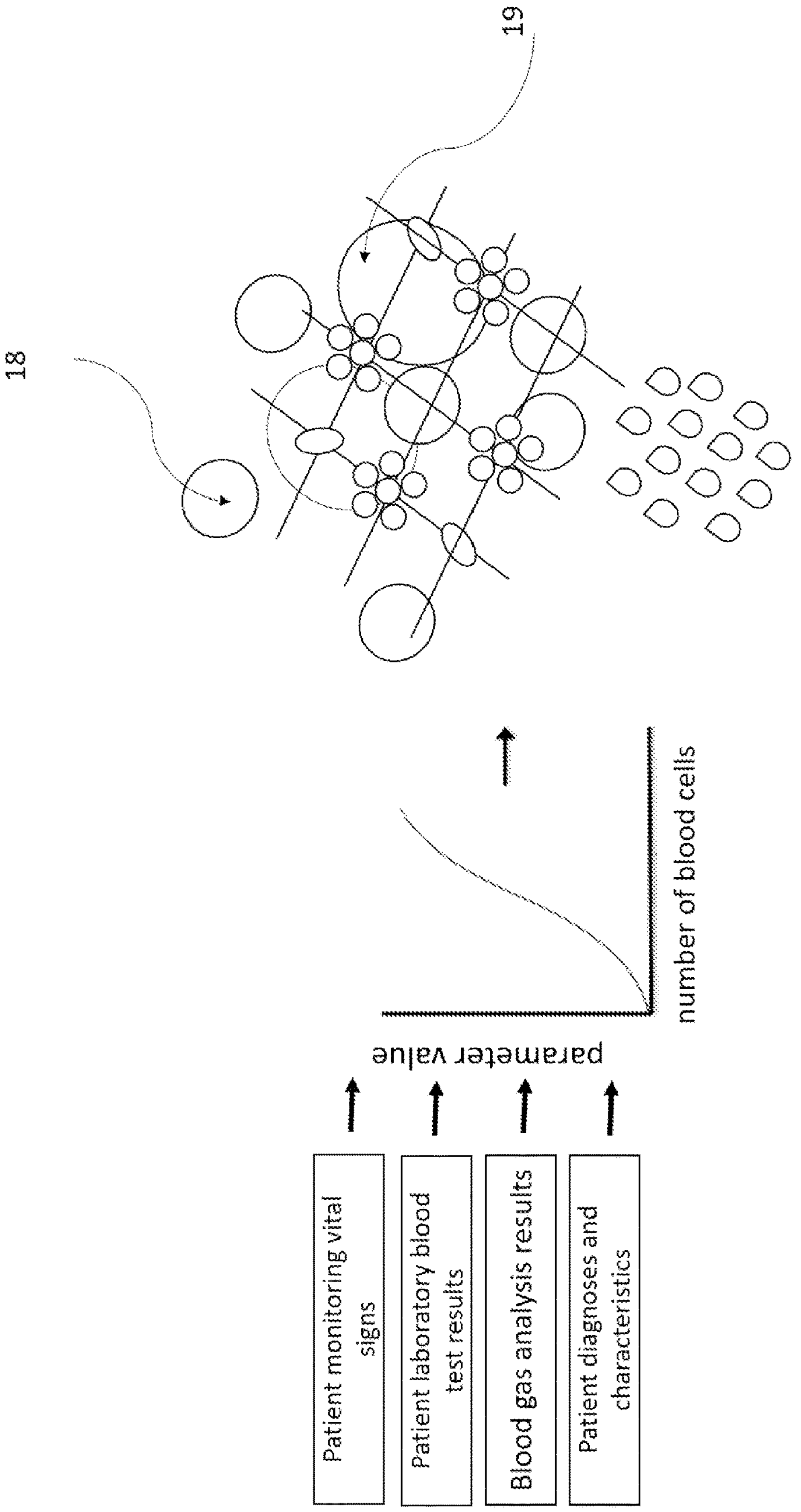

According to algorithm A3, changes in patient laboratory blood test results, blood gas analysis results, patient diagnoses and characteristics, and patient monitoring vital signs lead to a change in the number of blood cells shown in the background of the visual blood clot model 101 following an ease in ease out function. The ease in/out function causes very low and very high values of input coagulation function parameters to cause more extensive changes in number of blood cells compared to normal and less low and less high input parameter values. This function serves to enable users to detect low and high-extremes. FIG. 9 provides a schematic overview of this algorithm. For specific pre-defined diagnoses and characteristics stored in memory, the algorithm creates specific changes in the number of displayed blood cells, also stored in memory.

Examples: 1) The input: "high white blood cell count" causes the algorithm to increase the number of white blood cells 18 displayed. 2) The input "low red blood cell count" causes the algorithm to reduce the number of red blood cells 19 shown in the background. 3) The patient monitoring input "blood loss" causes the algorithm to show fewer blood cells. 4) The input: "leukocytosis" (laboratory blood test result) causes the algorithm to show more white blood cells. 5) The input low hemoglobin (blood gas analysis input) causes fewer blood cells to appear. 6) The input anemia (patient diagnosis and characteristic input) causes the algorithm to reduce the number of the red blood cells shown in the background.

Visual Blood Clot Algorithm A4 (Color of Blood Cells Displayed)

This algorithm is used to make part 1 (FIG. 1) of the visual blood clot model 101 (background) appear in an individualized way, which is modeled after and has logical commonality with, the characteristics a blood clot would have in the real patient that the input data comes from. Algorithm A4 uses the following inputs, however, is not limited to these or by these, as persons skilled in the art may think of additional inputs without departing from the scope of the description: Patient laboratory blood test results, blood gas analysis results, patient monitoring vital signs, patient diagnoses and characteristics.

Figure 10:
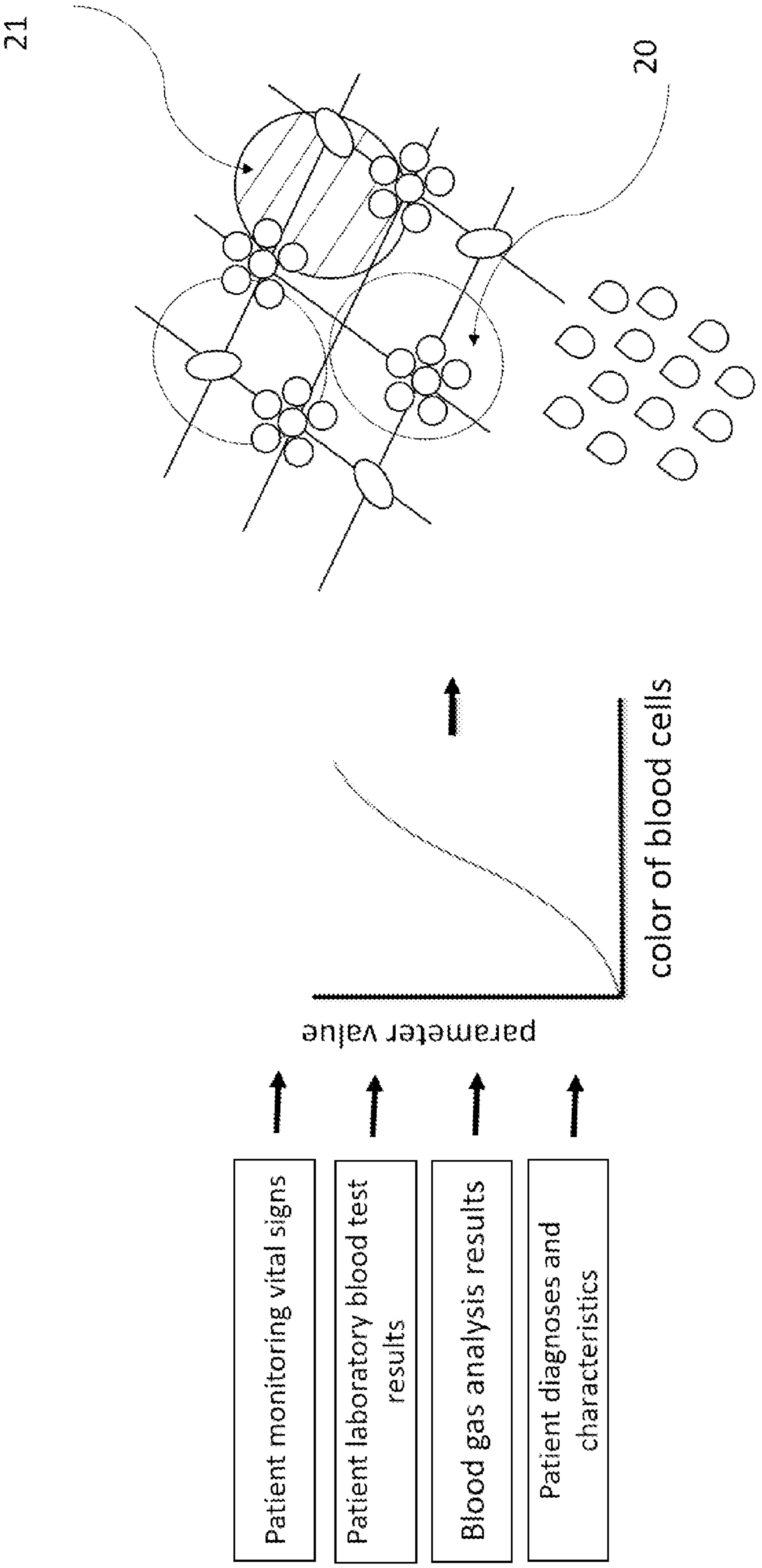

Changes patient laboratory blood test results, blood gas analysis results, patient diagnoses and characteristics, and patient monitoring vital signs lead to a change in the color of the blood cells shown in the background or part 1 of the visual blood clot model 101 following an ease in ease out function. The ease in/out function causes very low and very high values of input coagulation function parameters to cause more extensive changes in color of blood cells compared to normal and less low and less high input parameter values. This function serves to enable users to detect low and high-extremes. FIG. 10 provides a schematic overview of this algorithm. For specific pre-defined diagnoses and characteristics stored in memory, the algorithms create specific changes in the color of blood cells, also stored in memory.

Examples: 1) The coagulation function inputs "hypochromic anemia", or "low corpuscular hemoglobin concentration", or "low hemoglobin" (laboratory blood test result, blood gas analysis result, or patient diagnosis and characteristic) causes the algorithm to show a lighter red color of red blood cells (e.g., HEX color: #F9C8C8) 20 compared to "no anemia" input (e.g., HEX color: #F40E0E) 21.

Visual Blood Clot Algorithm A5 (Display of Specific Background Indicator Labels)

This algorithm is used to make part 1 (FIG. 1) of the visual blood clot model 101 (background) appear in an individualized way, which is modeled after and has logical commonality with, the characteristics a blood clot would have in the real patient that the input data comes from. Algorithm A5 uses the following inputs, however, is not limited to these or by these, as persons skilled in the art may think of additional inputs without departing from the scope of the description: laboratory blood test results, blood gas analysis results, patient diagnoses, characteristics, and patient monitoring vital signs.

Figure 11:
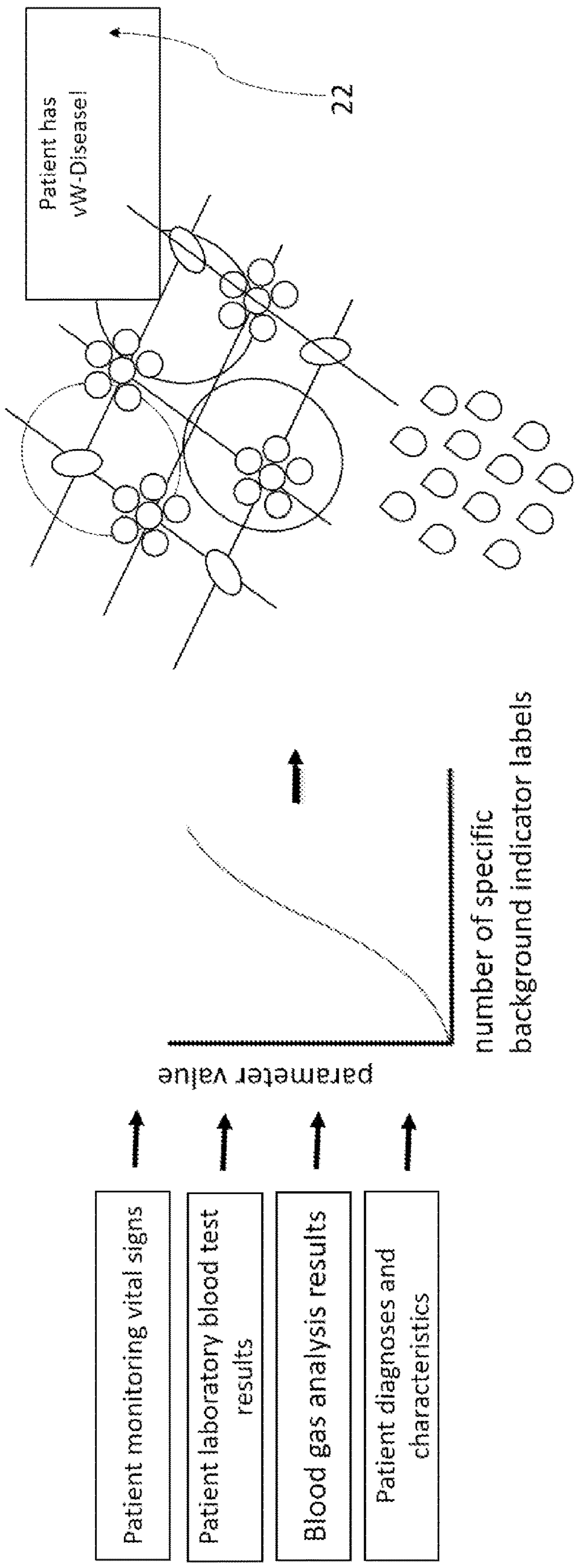

Changes in patient laboratory blood test results, blood gas analysis results, patient diagnoses and characteristics, and patient monitoring vital signs lead to a display of specific background indicator labels in the background or part 1 of the visual blood clot model 101 following an ease in ease out function. The ease in/out function causes very low and very high values of input coagulation function parameters to cause more or fewer specific background indicator labels compared to normal and less low and less high input parameter values. This function serves to enable users to detect low and high-extremes. FIG. 11 provides a schematic overview of this algorithm. For specific pre-defined diagnoses and characteristics stored in memory, the algorithm displays specific background indicator labels, also stored in memory. These background indicator labels may be in alphanumeric format, i.e. consist of text and numbers or be two or three-dimensional graphical indicators. Example: 1) The coagulation function input "Von Willebrand disease" (laboratory blood test result or patient diagnosis and characteristic) causes the algorithm to show a "Patient has vW-Disease" label 22 in the background of the visual blood clot model 101.

Visual Blood Clot Algorithm A6 (Volume [3D] and Area [2D] of Drug Indicators) and Algorithm A7 (Form of Drug Indicators)

These algorithms are used to make part 2 (FIG. 1) of the visual blood clot model 101 (drug indicator) appear in an individualized way, which is modeled after and has logical commonality with the characteristics a blood clot would have in the real patient that the input data comes from. Algorithms A6 and A7 use the following inputs, however, are not limited to these or by these, as persons skilled in the art may think of additional inputs without departing from the scope of the description: Patient laboratory blood test results, plasmatic drug levels, viscoelastic test outputs, patient diagnoses and characteristics, and patient monitoring vital signs.

Figure 12:
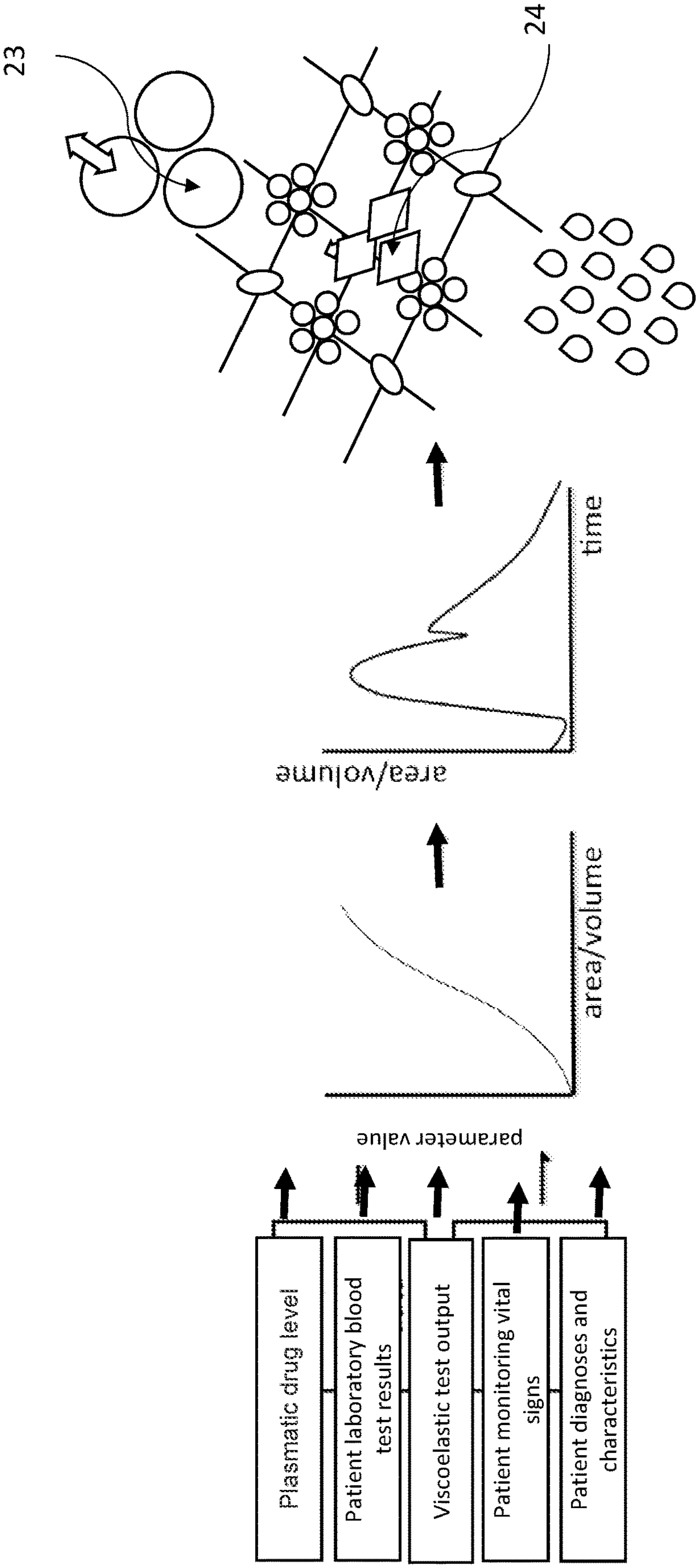

According to algorithms A6 and A7, changes in patient laboratory blood test results, blood gas analysis results, patient diagnoses and characteristics, and patient monitoring vital signs lead to a change in volume (3D) or area (2D) of the drug indicators shown in the visual blood clot model 101 following an ease in ease out function. The ease in/out function causes very low and very high values of input coagulation function parameters to cause more extensive changes in volume or area of parts (3D) or area (2D) of drug indicators compared to normal and less low and less high input parameter values. This function serves to enable users to detect low and high-extremes. FIG. 12 provides a schematic overview of these algorithms. For specific pre-defined diagnoses and characteristics stored in memory, the algorithms create specific changes in volume (3D), area (2D), or form of drug indicators, also stored in memory. Depending on specific patient characteristics, the drug indicators can change their volume or area according to vital values, as for example, pulse rate or arterial pressure curve.

Examples: 1) The patient monitoring input “rivaroxaban level high”, or “high plasmatic edoxaban level” (laboratory blood test result) causes the algorithms to make the drug indicators 23 appear larger. 2) The input: “low heparin concentration” (viscoelastic test result) causes the algorithms to make the drug indicator appear smaller. 3) The input “aspirin intake” causes the algorithm to change the shape of the drug indicators shown to the form of a diamond 24.

Visual Blood Clot Algorithm A8 (Number of Drug Indicators Displayed)

This algorithm is used to make part 2 (FIG. 1) of the visual blood clot model 101 (drug indicator) appear in an individualized way, which is modeled after and has logical commonality with, the characteristics a blood clot would have in the real patient that the input data comes from. Algorithm A8 uses the following inputs, however, is not limited to these or by these, as persons skilled in the art may think of additional inputs without departing from the scope of the description: Patient laboratory blood test results, plasmatic drug levels, viscoelastic test outputs, patient diagnoses and characteristics, and patient monitoring vital signs.

Figure 13:
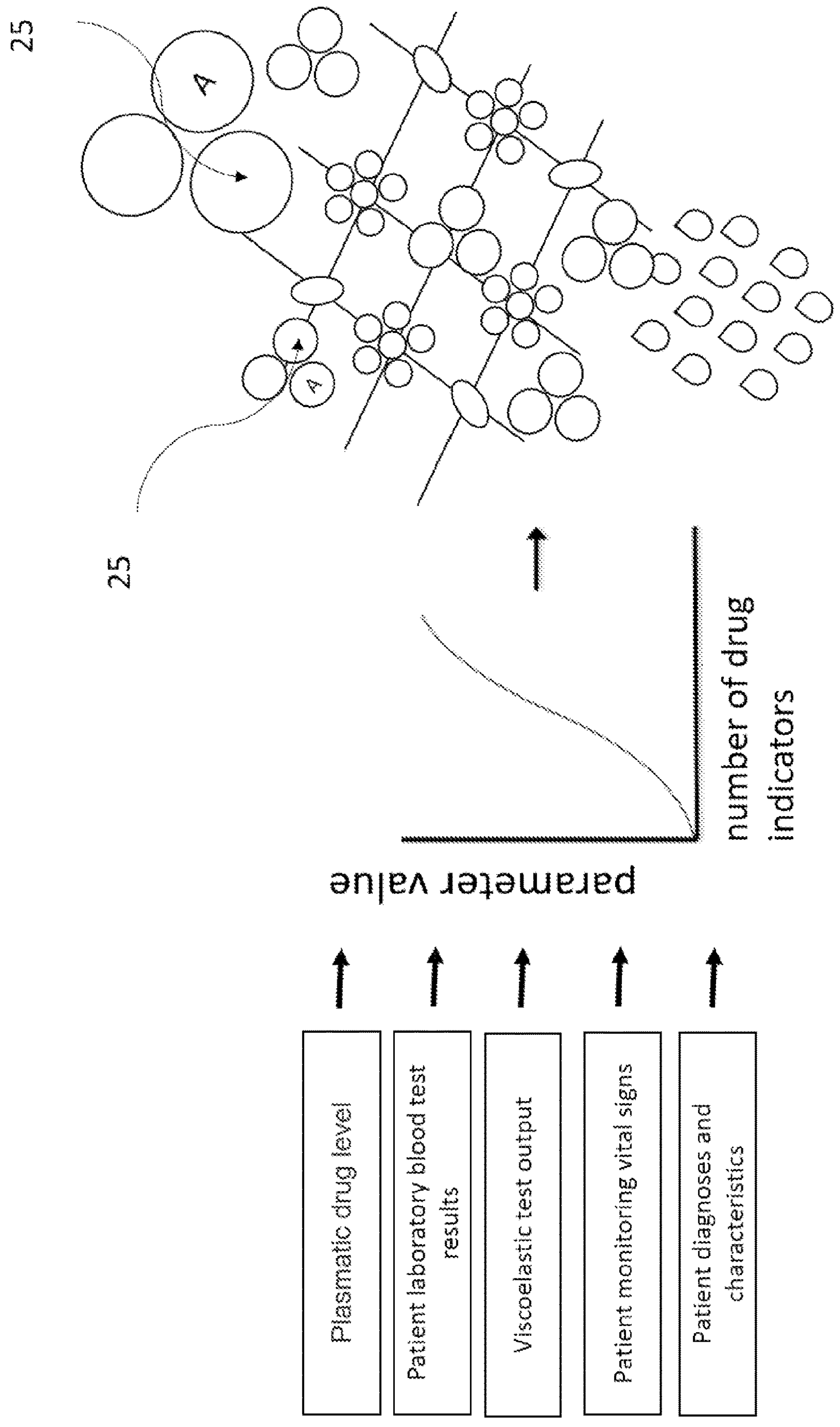

According to algorithm A8, changes in patient laboratory blood test results, blood gas analysis results, patient diagnoses and characteristics, and patient monitoring vital signs lead to a change in the number of drug indicators shown in the visual blood clot model 101 following an ease in ease out function. The ease in/out function causes very low and very high values of input coagulation function parameters to cause more extensive changes in number of drug indicators compared to normal and less low and less high input parameter values. This function serves to enable users to detect low and high-extremes. FIG. 13 provides a schematic overview of this algorithm. For specific pre-defined diagnoses and characteristics stored in memory, the algorithm creates specific changes in the number of displayed drug indicators, also stored in memory.

Examples: 1) The patient monitoring input “high apixaban” causes the algorithm to show more apixaban-specific drug indicators 25. 2) The input: “high heparin specific anti-factor-ten-a activity” (laboratory blood test result) causes the algorithm to show more heparin specific anti-factor-ten-a-activity drug indicators.

Visual Blood Clot Algorithm A9 (Color of Drug Indicators Displayed)

This algorithm is used to make part 2 (FIG. 1) of the visual blood clot model 101 (drug indicator) appear in an individualized way, which is modeled after and has logical commonality with, the characteristics a blood clot would have in the real patient that the input data comes from. Algorithm A9 uses the following inputs, however, is not limited to these or by these, as persons skilled in the art may think of additional inputs without departing from the scope of the description: Patient laboratory blood test results, plasmatic drug levels, viscoelastic test outputs, patient diagnoses and characteristics, and patient monitoring vital signs.

Figure 14:
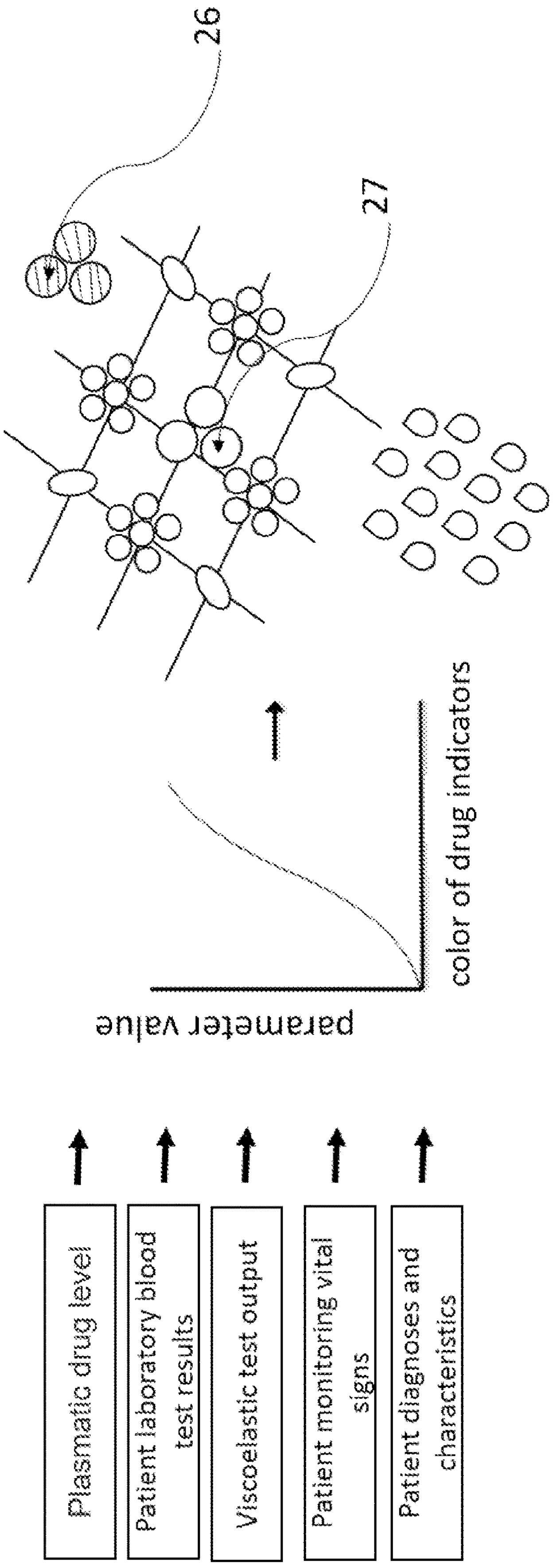

According to algorithm A9, changes in patient laboratory blood test results, blood gas analysis results, patient diagnoses and characteristics, and patient monitoring vital signs lead to a change in the color of the drug indicators shown in the visual blood clot model 101 following an ease in ease out function. The ease in/out function causes very low and very high values of input coagulation function parameters to cause more extensive changes in color of drug indicators compared to normal and less low and less high input parameter values. This function serves to enable users to detect low and high-extremes. FIG. 14 provides a schematic overview of this algorithm. For specific pre-defined diagnoses and characteristics stored in memory, the algorithms create specific changes in the color of drug indicators, also stored in memory.

Example: The coagulation function input “heparin detected”, or “high heparin-specific anti-factor-ten-a-activity” (viscoelastic whole blood test result or patient diagnosis and characteristic) causes the algorithm to show a green color of drug indicators (e.g., HEX color: #32CD32) 26 compared to a white “no heparin detected” drug indicator (e.g., HEX color: #FFFFFF) 27.

Visual Blood Clot Algorithm A10 (Display of Specific Drug Indicator Labels)

This algorithm is used to make part 2 (FIG. 1) of the visual blood clot model 101 (drug indicator) appear in an individualized way, which is modeled after and has logical commonality with, the characteristics a blood clot would have in the real patient that the input data comes from. Algorithm A10 uses the following inputs, however, is not limited to these or by these, as persons skilled in the art may think of additional inputs without departing from the scope of the description: Patient laboratory blood test results, plasmatic drug levels, viscoelastic test outputs, patient diagnoses and characteristics, and patient monitoring vital signs.

Figure 15:
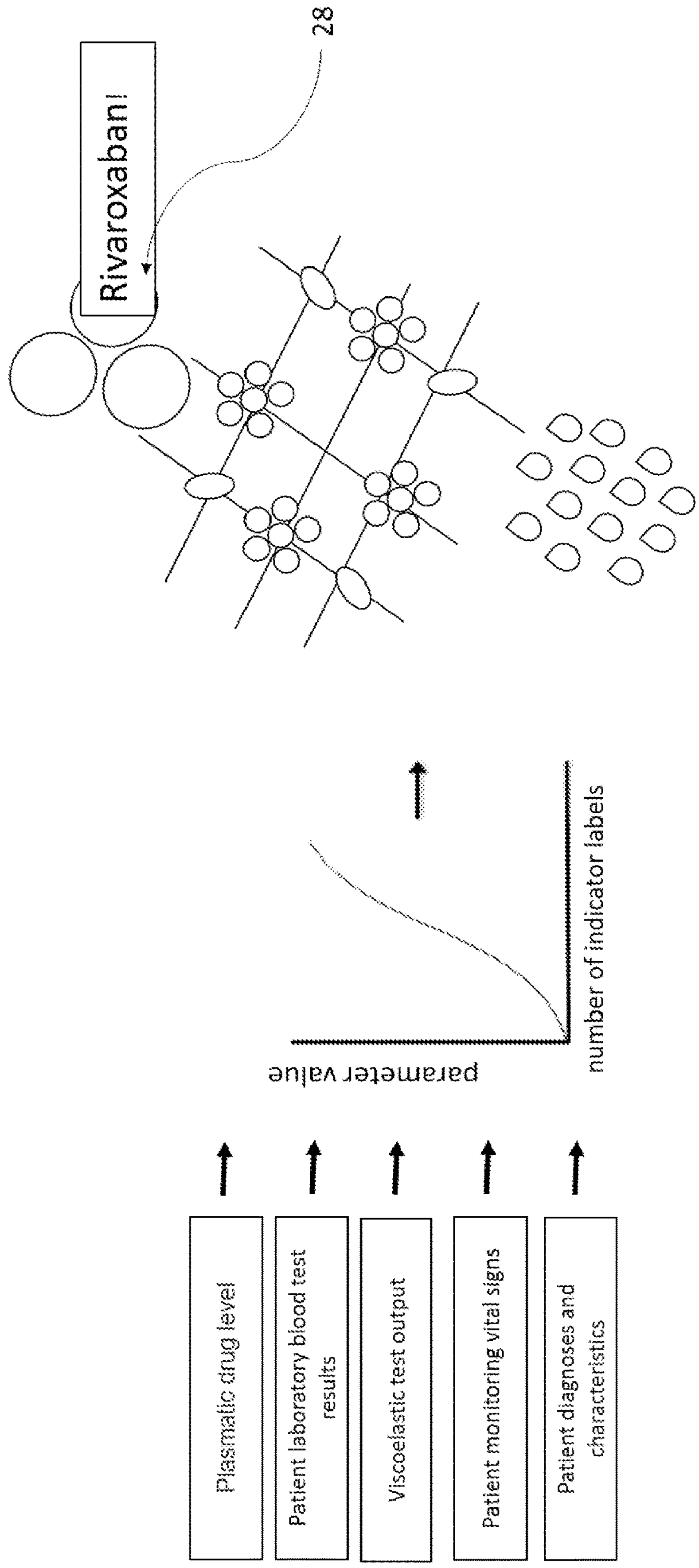

Changes in patient laboratory blood test results, plasmatic drug levels, viscoelastic test outputs, patient diagnoses and characteristics, and patient monitoring vital signs lead to a display of specific drug indicator labels in part 2 of the visual blood clot model 101 following an ease in ease out function. The ease in/out function causes very low and very high values of input coagulation function parameters to cause more or fewer specific background indicator labels compared to normal and less low and less high input parameter values. This function serves to enable users to detect low and high-extremes. FIG. 15 provides a schematic overview of this algorithm. For specific pre-defined diagnoses and characteristics stored in memory, the algorithm displays specific drug indicator labels, also stored in memory. These drug indicator labels may be in alphanumeric format, i.e. consist of text and numbers or be two or three-dimensional graphical indicators.

Example: 1) The coagulation function input “Rivaroxaban level high” (laboratory blood test result or patient diagnosis and characteristic) causes the algorithm to show a graphical or alphanumeric “Rivaroxaban” label in the drug indicators 28 of the visual blood clot model 101.

Visual Blood Clot Algorithm A11 (Volume [3D] and Area [2D] of Fibrin Mesh Indicator) and Algorithm A12 (Form of Fibrin Mesh Indicator)

These algorithms are used to make part 3 (FIG. 1) of the visual blood clot model 101 (fibrin mesh indicator) appear in an individualized way, which is modeled after and has logical commonality with, the characteristics a blood clot would have in the real patient that the input data comes from. Algorithms A11 and A12 use the following inputs, however, are not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 16:
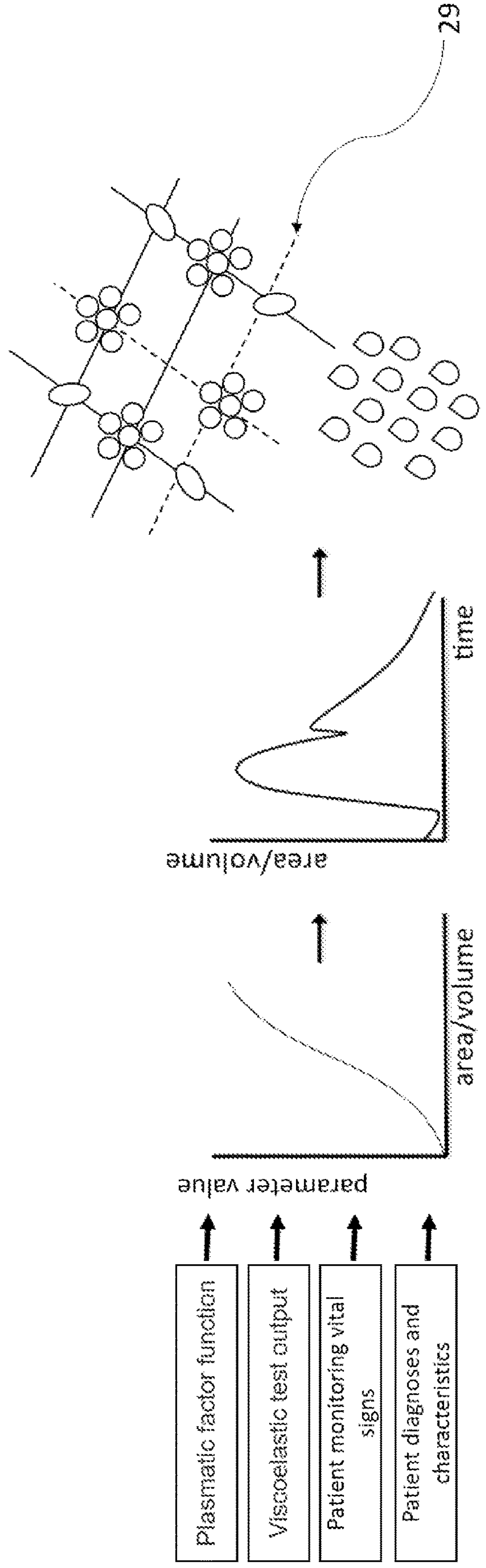

According to algorithms A11 and A12, changes in patient laboratory blood test results (plasmatic coagulation factor function), viscoelastic test output, patient monitoring vital signs, patient diagnoses and characteristics lead to a change in volume (3D) or area (2D) of the fibrin mesh indicator shown in the visual blood clot model 101 following an ease in ease out function. The ease in/out function causes very low and very high values of input coagulation function parameters to cause more extensive changes in volume or area of parts (3D) or area (2D) of fibrin mesh indicator compared to normal and less low and less high input parameter values. This function serves to enable users to detect low and high-extremes. FIG. 16 provides a schematic overview of the logic of the visual blood clot algorithms A11 and A12 with graphical examples. 1: The input "low fibrin" causes the algorithm to change the form of the fibrin mesh indicator (1 and 2) to appear broken (2). For specific pre-defined diagnoses and characteristics stored in memory, the algorithms create specific changes in volume (3D), area (2D), or form of the fibrin mesh indicator, also stored in memory. Depending on specific vital sign values or patient characteristics, the blood cells or other background components can change their volume or area according to vital values, as for example, pulse rate or arterial pressure curve.

Examples: 1) The patient data management system input "low plasmatic coagulation factor 13 activity" (laboratory blood test result) causes the algorithms to make the fibrin mesh indicator appear interrupted or broken 2) The input: "low maximum clot firmness in FIBTEM" (viscoelastic test output) causes the algorithms to make the fibrin mesh indicator appear smaller.

Visual Blood Clot Algorithm A13 (Number of Fibrin Mesh Indicators Displayed)

This algorithm is used to make part 3 (FIG. 1) of the visual blood clot model 101 (fibrin mesh indicator) appear in an individualized way, which is modeled after and has logical commonality with, the characteristics a blood clot would have in the real patient that the input data comes from. Algorithm A13 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 17:
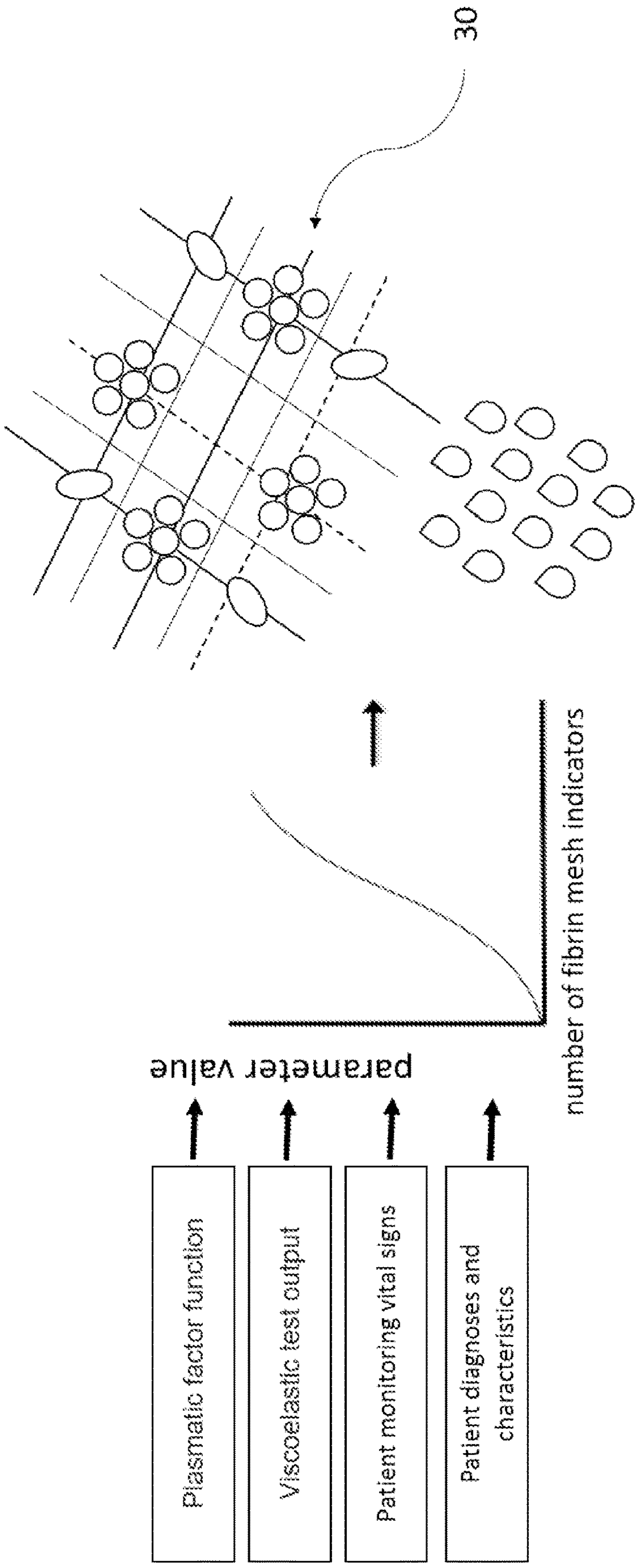

According to algorithm A13, changes in patient laboratory blood test results (plasmatic coagulation factor function), viscoelastic test output, patient monitoring vital signs, patient diagnoses and characteristics lead to a change in the number of fibrin mesh indicators shown in the visual blood clot model 101 following an ease in ease out function. The ease in/out function causes very low and very high values of input coagulation function parameters to cause more extensive changes in number of fibrin mesh indicators compared to normal and less low and less high input parameter values. This function serves to enable users to detect low and high-extremes. FIG. 17 provides a schematic overview of this algorithm. For specific pre-defined diagnoses and characteristics stored in memory, the algorithm creates specific changes in the number of displayed fibrin mesh indicators, also stored in memory.

Examples: 1) The patient laboratory blood test result "low fibrin concentration" causes the algorithm to show fewer fibrin mesh indicators (29) instead of normal fibrin mesh indicators (2). 2: The input: "high MCF in FIBTEM" (viscoelastic test output) causes the algorithm to show more fibrin mesh indicators (30)

Visual Blood Clot Algorithm A14 (Color of Fibrin Mesh Indicators Displayed)

This algorithm is used to make part 3 (FIG. 1) of the visual blood clot model 101 (fibrin mesh indicator) appear in an individualized way, which is modeled after and has logical commonality with, the characteristics a blood clot would have in the real patient that the input data comes from. Algorithm A14 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 18:
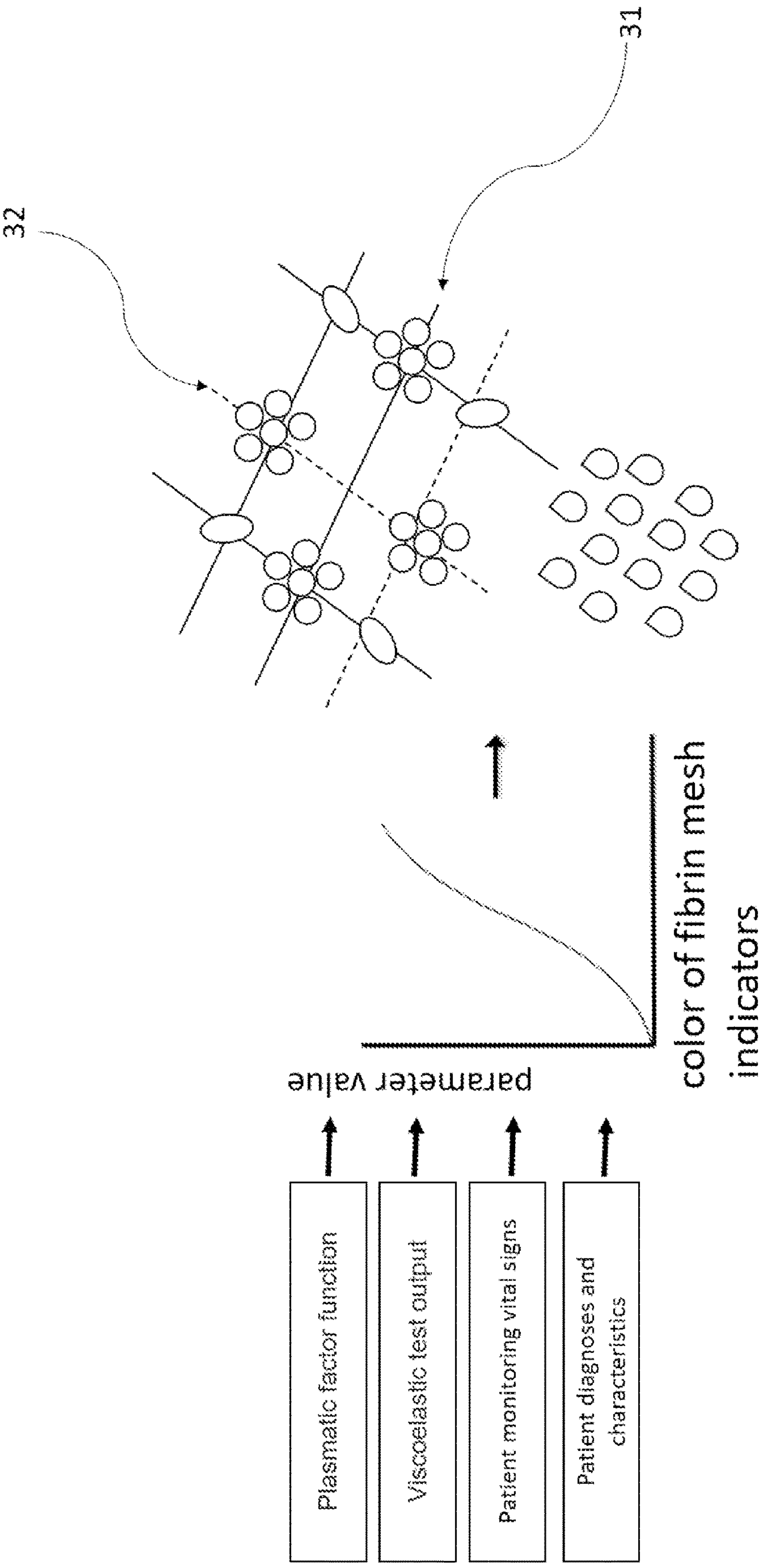

According to algorithm A14, changes in patient laboratory blood test results (plasmatic coagulation factor function), viscoelastic test output, patient monitoring vital signs, patient diagnoses and characteristics lead to a change in the color of the fibrin mesh indicators or part 3 of the visual blood clot model 101 following an ease in ease out function. The ease in/out function causes very low and very high values of input coagulation function parameters to cause more extensive changes in color of fibrin mesh compared to normal and less low and less high input parameter values. This function serves to enable users to detect low and high-extremes. FIG. 18 provides a schematic overview of this algorithm. For specific pre-defined diagnoses and characteristics stored in memory, the algorithms create specific changes in the color of fibrin mesh, also stored in memory.

Examples: 1) The coagulation function input "high fibrin concentration" (laboratory blood test result or patient diagnosis and characteristic) causes the algorithm to show the fibrin mesh indicators in a darker color of yellow (e.g., HEX color: #FFD000) 31 compared to "low fibrin concentration" input (e.g., HEX color: #EFF7BA) 32.

Visual Blood Clot Algorithm A15 (Display of Specific Fibrin Mesh Indicator Labels)

This algorithm is used to make part 3 (FIG. 1) of the visual blood clot model 101 (fibrin mesh indicator) appear in an individualized way, which is modeled after and has logical commonality with, the characteristics a blood clot would have in the real patient that the input data comes from. Algorithm A15 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 19:
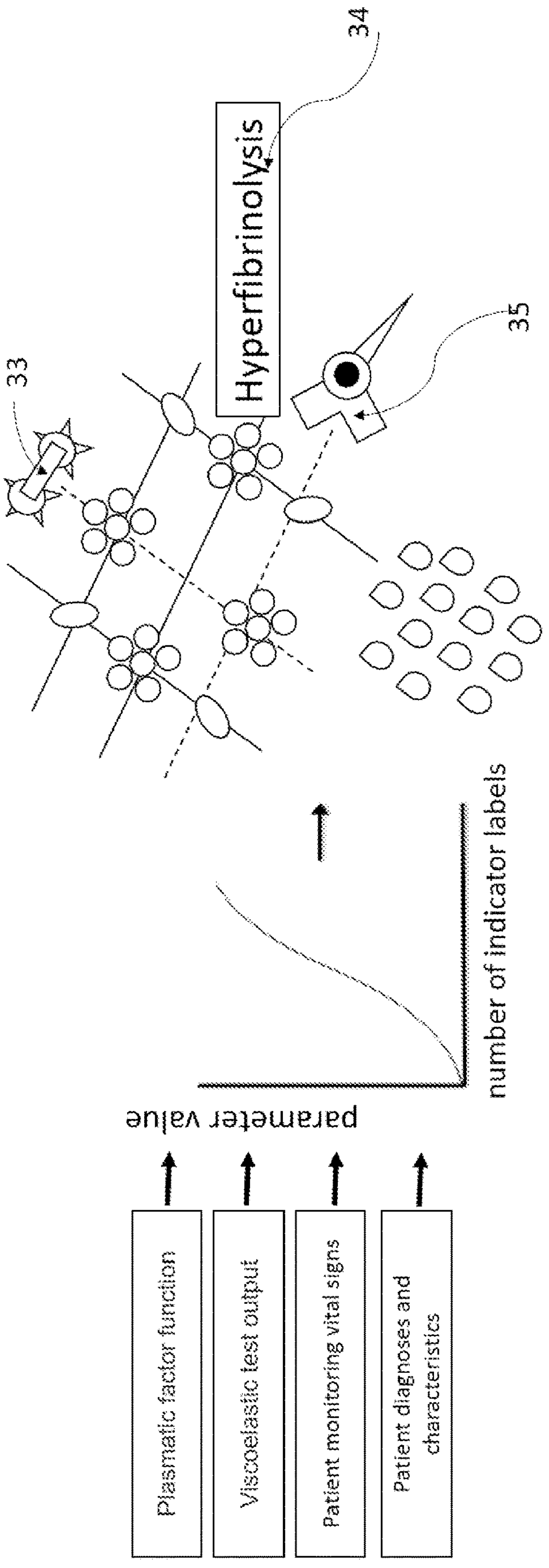

According to algorithm A15, changes in patient laboratory blood test results (plasmatic coagulation factor function), viscoelastic test output, patient monitoring vital signs, patient diagnoses and characteristics lead to a display of specific background indicator labels in part 3 (fibrin mesh indicator) of the visual blood clot model 101 following an ease in ease out function. The ease in/out function causes very low and very high values of input coagulation function parameters to cause more or fewer specific background indicator labels compared to normal and less low and less high input parameter values. This function serves to enable users to detect low and high-extremes. FIG. 19 provides a schematic overview of this algorithm. For specific pre-defined diagnoses and characteristics stored in memory, the algorithm displays specific background indicator labels, also stored in memory. These background indicator labels may be in alphanumeric format, i.e. consist of text and numbers or be two or three-dimensional graphical indicators.

Example: 1) The coagulation function input "Hyperfibrinolysis" (viscoelastic test output) causes the algorithm to show a graphical enzyme label 33 or an eating crocodile label (34) above part 3 (fibrin mesh indicator) of the visual blood clot model 101.

Visual Blood Clot Algorithm A16 (Volume [3D] and Area [2D] of Plasmatic Factor Indicator) and Algorithm A17 (Form of Plasmatic Factor Indicator)

These algorithms are used to make part 4 (FIG. 1) of the visual blood clot model 101 (plasmatic factor indicator) appear in an individualized way, which is modeled after and has logical commonality with, the characteristics a blood clot would have in the real patient that the input data comes from. Algorithms A16 and A17 use the following inputs, however, are not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 20:
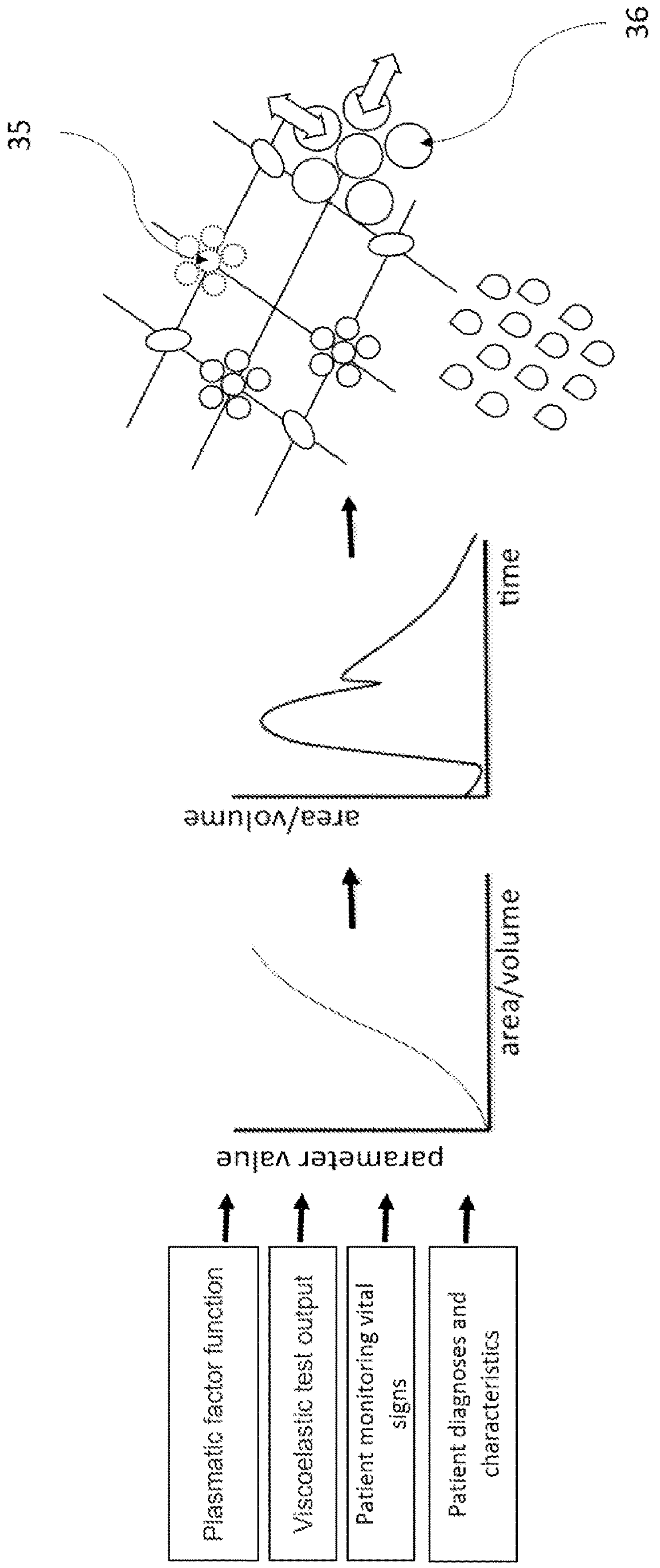

According to algorithms A16 and A17, changes in patient laboratory blood test results (plasmatic coagulation factor function), viscoelastic test output, patient monitoring vital signs, patient diagnoses and characteristics lead to a change in volume (3D) or area (2D) of the plasmatic factor indicator shown in the visual blood clot model 101 following an ease in ease out function. The ease in/out function causes very low and very high values of input coagulation function parameters to cause more extensive changes in volume or area of parts (3D) or area (2D) of plasmatic factor indicator compared to normal and less low and less high input parameter values. This function serves to enable users to detect low and high-extremes. FIG. 20 provides a schematic overview of these algorithms. For specific pre-defined diagnoses and characteristics stored in memory, the algorithms create specific changes in volume (3D), area (2D), or form of the plasmatic factor indicator, also stored in memory. Depending on specific vital sign values or patient characteristics, the blood cells or other background components can change their volume or area according to vital values, as for example, pulse rate or arterial pressure curve.

Examples: 1) The patient data management system input "low plasmatic coagulation factor 13 activity" (laboratory blood test result) causes the algorithms to make the plasmatic factor indicators 35 appear interrupted or broken. 2) The input: "long clotting time in EXTEM INTEM (viscoelastic test output) causes the algorithms to make the clotting factors 36 appear smaller.

Visual Blood Clot Algorithm A18 (Number of Plasmatic Factor Indicators Displayed)

This algorithm is used to make part 4 (FIG. 1) of the visual blood clot model 101 (plasmatic factor indicator) appear in an individualized way, which is modeled after and has logical commonality with, the characteristics a blood clot would have in the real patient that the input data comes from. Algorithm A18 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 21:
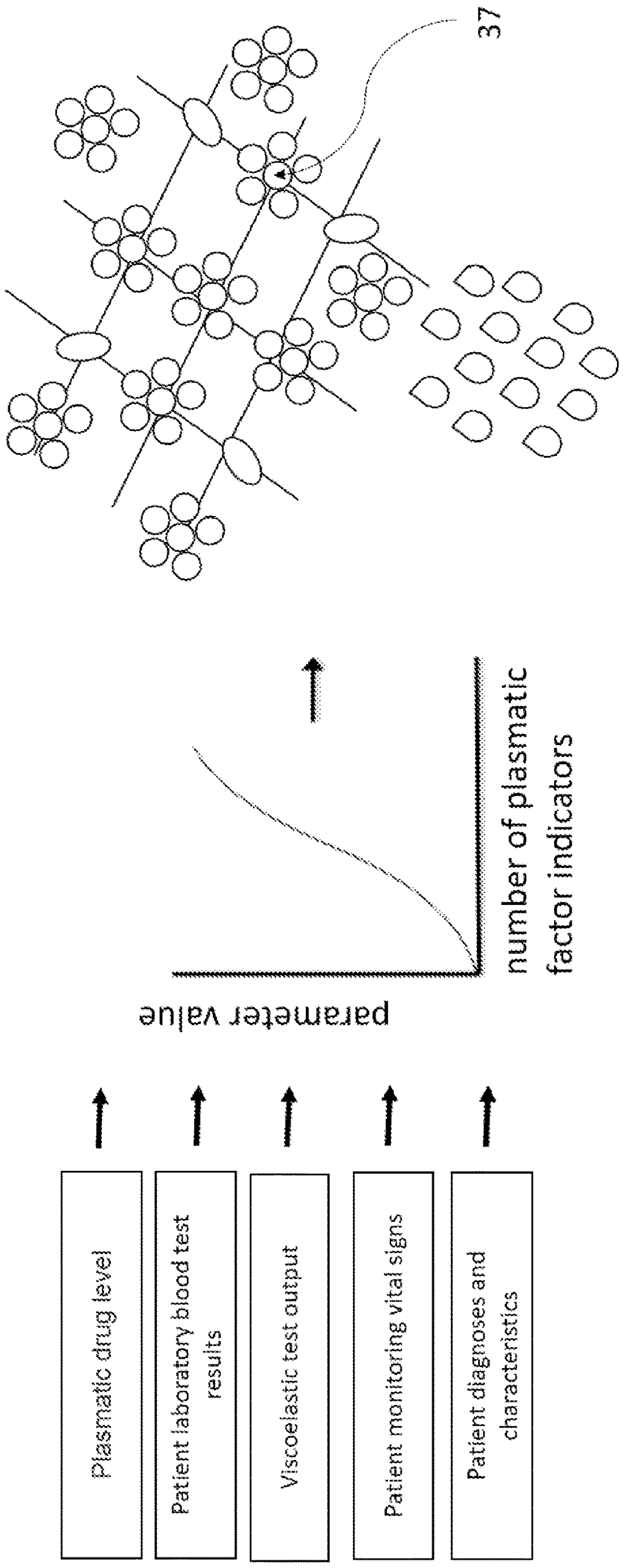

According to algorithm A18, changes in patient laboratory blood test results (plasmatic coagulation factor function), viscoelastic test output, patient monitoring vital signs, patient diagnoses and characteristics lead to a change in the number of plasmatic factor indicators shown in the visual blood clot model 101 following an ease in ease out function. The ease in/out function causes very low and very high values of input coagulation function parameters to cause more extensive changes in number of plasmatic factor indicators compared to normal and less low and less high input parameter values. This function serves to enable users to detect low and high-extremes. FIG. 21 provides a schematic overview of this algorithm. For specific pre-defined diagnoses and characteristics stored in memory, the algorithm creates specific changes in the number of displayed plasmatic factor indicators, also stored in memory.

Examples: 1) The input: "hemophilia" causes the algorithm to decrease the number of plasmatic factor indicators displayed. 2) The input: "Prothrombin gene mutation" causes the algorithm to increase the number of plasmatic factor indicators 37 displayed.

Visual Blood Clot Algorithm A19 (Color of Plasmatic Factor Indicators Displayed)

This algorithm is used to make part 4 (FIG. 1) of the visual blood clot model 101 (plasmatic factor indicators) appear in an individualized way, which is modeled after and has logical commonality with, the characteristics a blood clot would have in the real patient that the input data comes from. Algorithm A19 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 22:
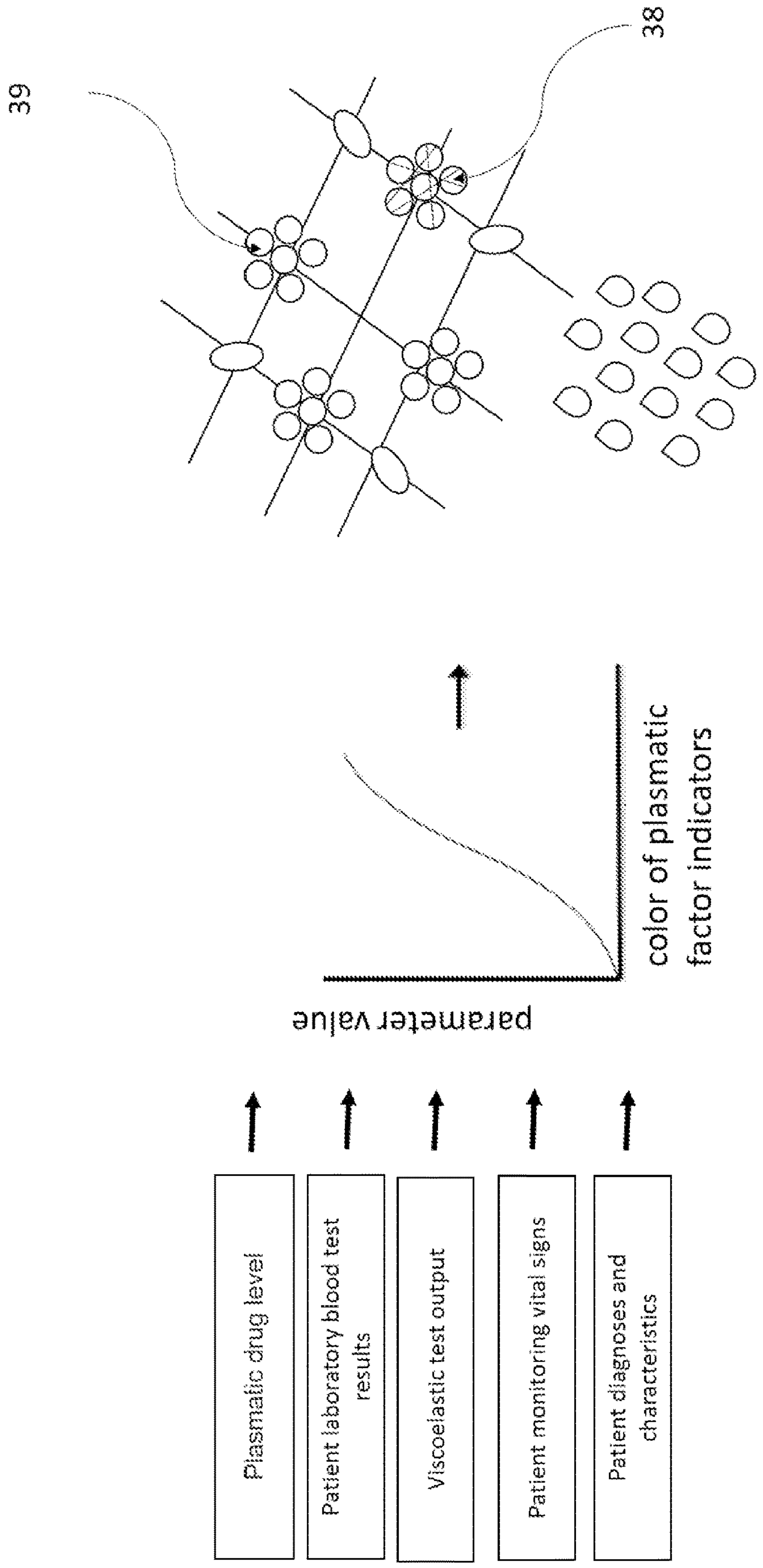

According to algorithm A19, changes in patient laboratory blood test results (plasmatic coagulation factor function), viscoelastic test output, patient monitoring vital signs, patient diagnoses and characteristics lead to a change in the color of the plasmatic factor indicators or part 4 of the visual blood clot model 101 following an ease in ease out function. The ease in/out function causes very low and very high values of input coagulation function parameters to cause more extensive changes in color of plasmatic factor indicators compared to normal and less low and less high input parameter values. This function serves to enable users to detect low and high-extremes. FIG. 22 provides a schematic overview of this algorithm. For specific pre-defined diagnoses and characteristics stored in memory, the algorithms create specific changes in the color of plasmatic factor indicators, also stored in memory.

Example: The input: "high coagulation factor 13 activity" causes the algorithm to show a more intense color of the plasmatic factor indicators displayed (e.g., HEX color: #6A046D) (38), compared to the normal color (e.g., HEX color: #F1DEF2) (39).

Visual Blood Clot Algorithm A20 (Display of Specific Plasmatic Factor Indicator Labels)

This algorithm is used to make part 4 (FIG. 1) of the visual blood clot model 101 (plasmatic factor indicators) appear in an individualized way, which is modeled after and has logical commonality with, the characteristics a blood clot would have in the real patient that the input data comes from. Algorithm A20 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 23:
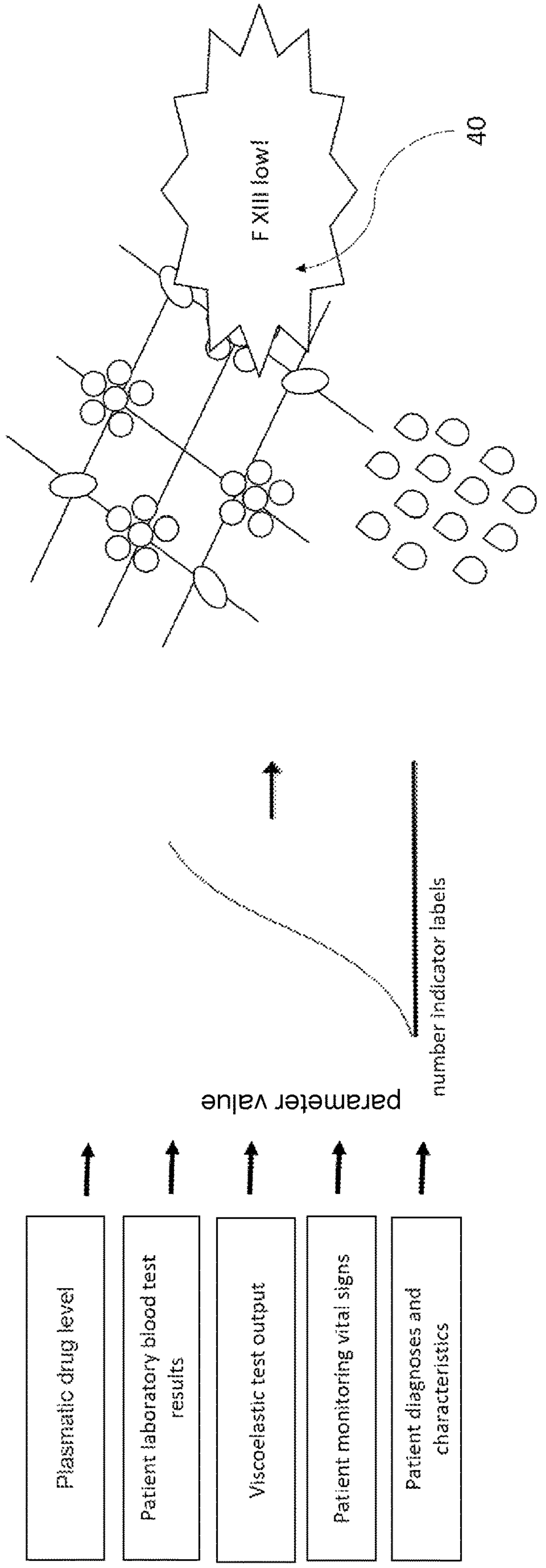

According to algorithm A20, changes in patient laboratory blood test results (plasmatic coagulation factor function), viscoelastic test output, patient monitoring vital signs, patient diagnoses and characteristics lead to a display of specific background indicator labels in part 4 (plasmatic factor indicators) of the visual blood clot model 101 following an ease in ease out function. The ease in/out function causes very low and very high values of input coagulation function parameters to cause more or fewer specific background indicator labels compared to normal and less low and less high input parameter values. This function serves to enable users to detect low and high-extremes. FIG. 23 provides a schematic overview of this algorithm. For specific pre-defined diagnoses and characteristics stored in memory, the algorithm displays specific background indicator labels, also stored in memory. These background indicator labels may be in alphanumeric format, i.e. consist of text and numbers or be two or three-dimensional graphical indicators. Example: The input: "Factor XIII low" causes the algorithm to show a Factor XIII low indicator label 40 above part 4 of the blood clot model 101.

Visual Blood Clot Algorithm A21 (Volume [3D] and Area [2D] of Blood Drops and Pool of Blood Indicators) and Algorithm A22 (Form of Blood Drops and Pool of Blood Indicators)

These algorithms are used to make part 5 (FIG. 1) of the visual blood clot model 101 (blood drops and pool of blood indicators) appear in an individualized way, which is modeled after and has logical commonality with, the characteristics a blood clot would have in the real patient that the input data comes from. Algorithms A21 and A22 use the following inputs, however, are not limited to these or by these, as persons skilled in the art may think of additional inputs without departing from the scope of the description: Patient laboratory blood test results (plasmatic coagulation factor function and plasmatic drug levels), viscoelastic test output, thrombocyte function tests, patient monitoring vital signs, patient diagnoses and characteristics.

Figure 24:
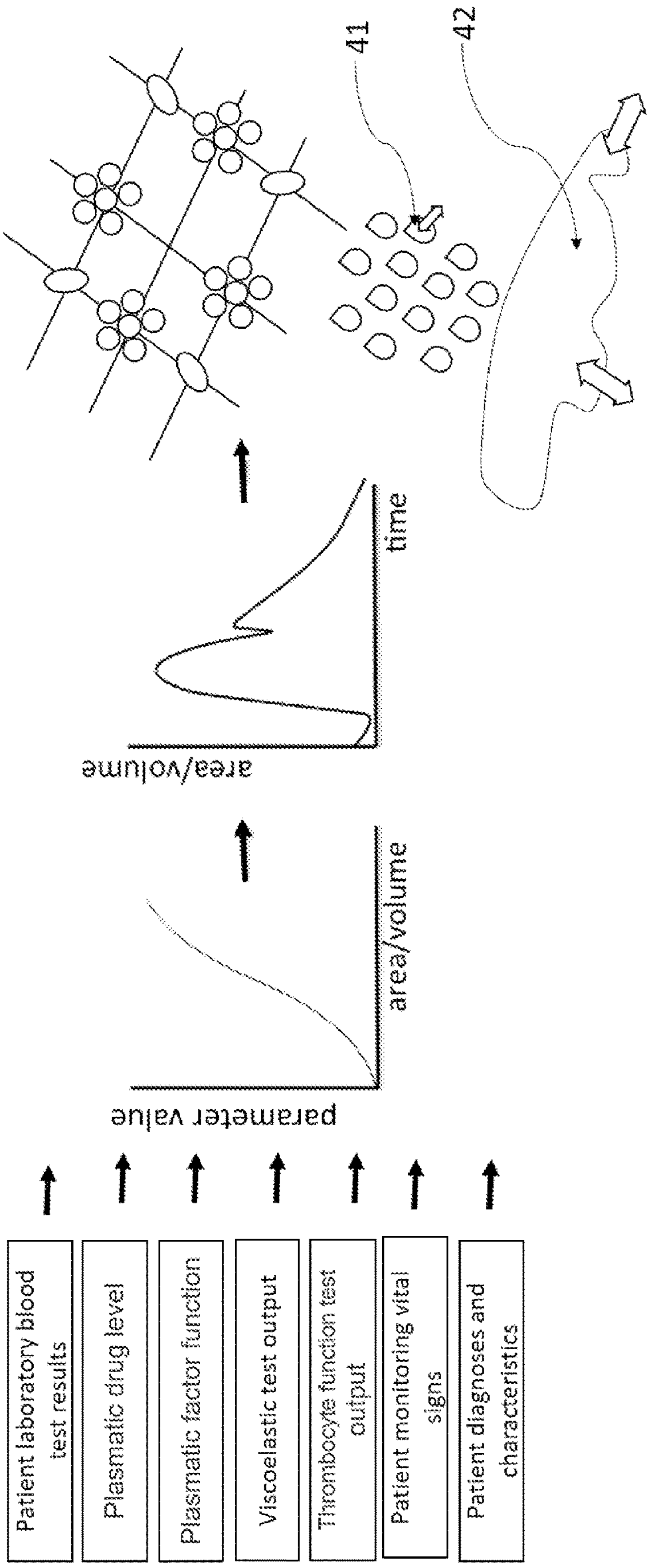

According to algorithms A21 and A22, changes in patient laboratory blood test results (plasmatic coagulation factor function and plasmatic drug levels), viscoelastic test output, thrombocyte function tests, patient monitoring vital signs, patient diagnoses and characteristics lead to a change in volume (3D) or area (2D) of the blood drops and pool of blood indicators shown in the visual blood clot model 101 following an ease in ease out function. The ease in/out function causes very low and very high values of input coagulation function parameters to cause more extensive changes in volume or area of parts (3D) or area (2D) of blood drops and pool of blood indicators compared to normal and less low and less high input parameter values. This function serves to enable users to detect low and high-extremes. FIG. 24 provides a schematic overview of these algorithms. For specific pre-defined diagnoses and characteristics stored in memory, the algorithms create specific changes in volume (3D), area (2D), or form of the blood drops and pool of blood indicators, also stored in memory. Depending on specific vital sign values or patient characteristics, the blood drops and pool of blood indicators can change their volume or area according to vital values, as for example, pulse rate or arterial pressure curve.

Example: 1) The input "high blood loss" from the patient data management system causes the algorithm to change the form of the blood drops 41 and pool of blood indicators 42 to appear larger.

Visual Blood Clot Algorithm A23 (Number of Blood Drops and Pool of Blood Indicators Displayed)

This algorithm is used to make part 5 (FIG. 1) of the visual blood clot model 101 (blood drops and pool of blood indicators) appear in an individualized way, which is modeled after and has logical commonality with, the characteristics a blood clot would have in the real patient that the input data comes from. Algorithm A23 uses the following inputs, however, is not limited to these or by these, as persons skilled in the art may think of additional inputs without departing from the scope of the description: Patient laboratory blood test results (plasmatic coagulation factor function and plasmatic drug levels), viscoelastic test output, thrombocyte function tests, patient monitoring vital signs, patient diagnoses and characteristics.

Figure 25:
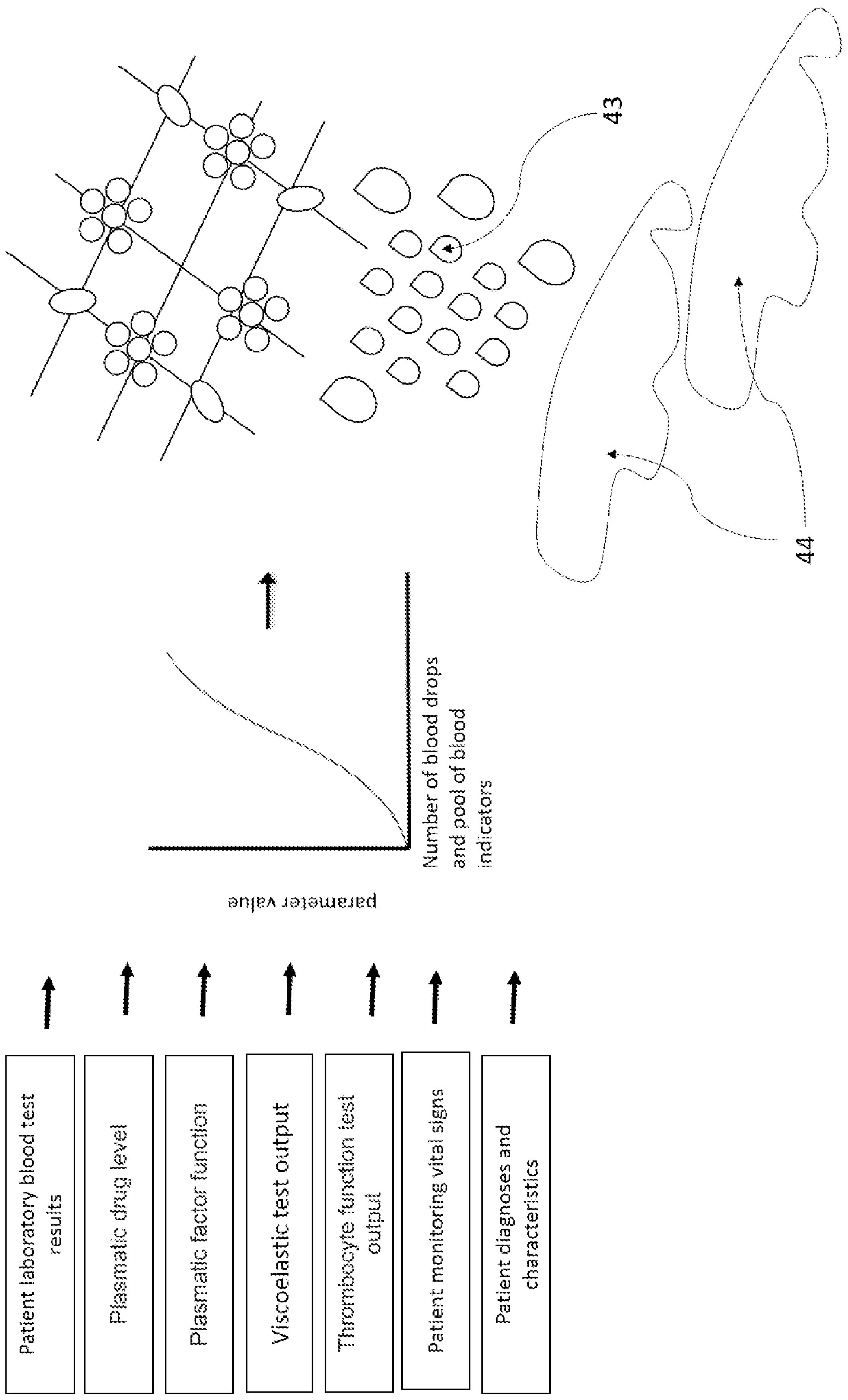

According to algorithm A23, changes in patient laboratory blood test results (plasmatic coagulation factor function and plasmatic drug levels), viscoelastic test output, thrombocyte function tests, patient monitoring vital signs, patient diagnoses and characteristics lead to a change in the number of blood drops and pool of blood indicators shown in the visual blood clot model 101 following an ease in ease out function. The ease in/out function causes very low and very high values of input coagulation function parameters to cause more extensive changes in number of blood drops and pool of blood indicators compared to normal and less low and less high input parameter values. This function serves to enable users to detect low and high-extremes. FIG. 25 provides a schematic overview of this algorithm. For specific pre-defined diagnoses and characteristics stored in memory, the algorithm creates specific changes in the number of displayed blood drops and pool of blood indicators, also stored in memory.

Example: The input "long clotting time in EXTEM and INTEM viscoelastic test" causes the algorithm to increase the number of blood drops and pool of blood indicators displayed. The input: "low MCF in FIBTEM viscoelastic test" causes the algorithm to increase the number of blood drops 43 and pool of blood indicators 44 displayed.

Visual Blood Clot Algorithm A24 (Color of Blood Drops and Pool of Blood Indicators Displayed)

This algorithm is used to make part 5 (FIG. 1) of the visual blood clot model 101 (blood drops and pool of blood indicators) appear in an individualized way, which is modeled after and has logical commonality with, the characteristics a blood clot would have in the real patient that the input data comes from. Algorithm A24 uses the following inputs, however, is not limited to these or by these, as persons skilled in the art may think of additional inputs without departing from the scope of the description: Patient laboratory blood test results (plasmatic coagulation factor function and plasmatic drug levels), viscoelastic test output, thrombocyte function tests, patient monitoring vital signs, patient diagnoses and characteristics.

Figure 26:
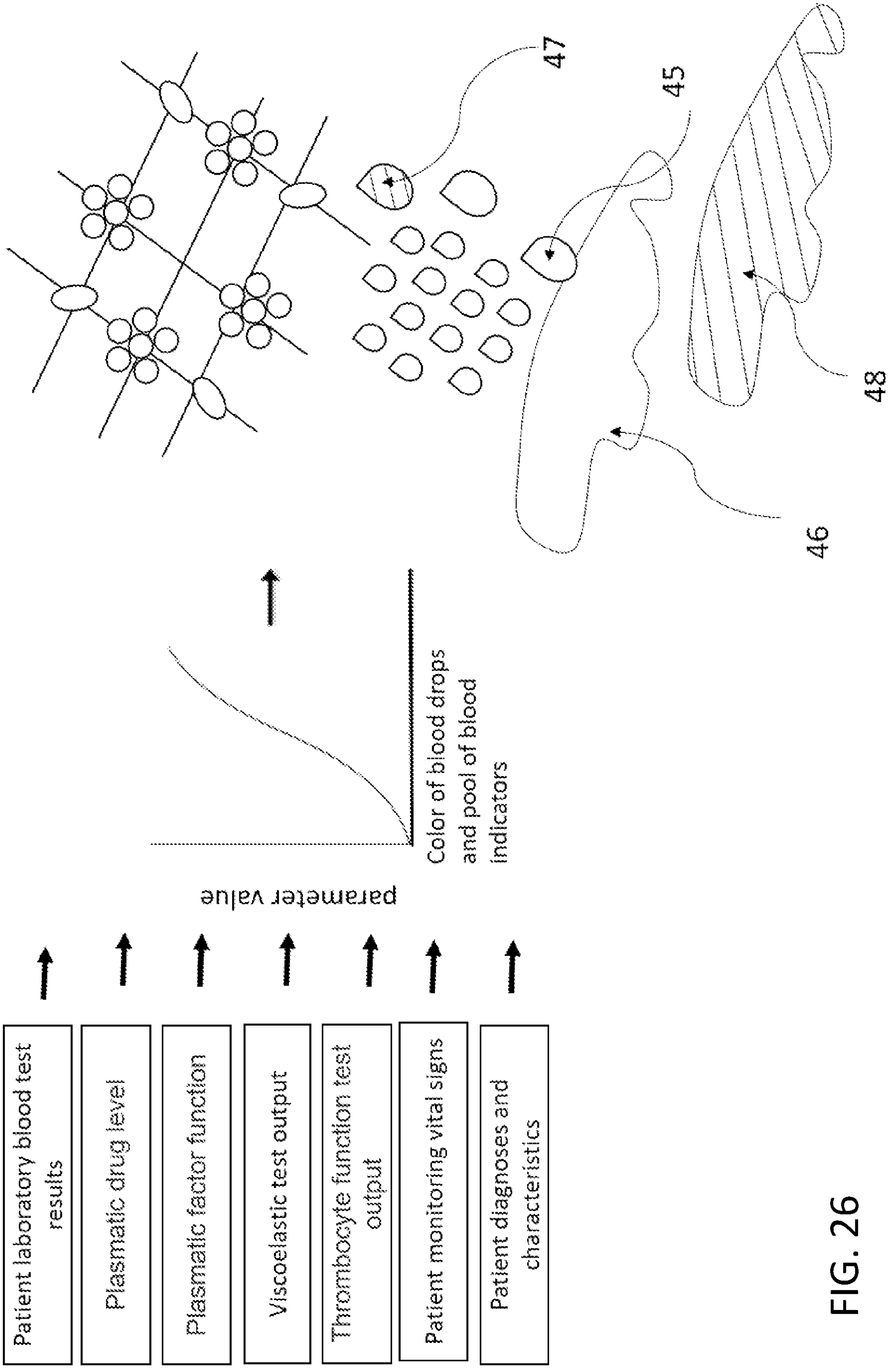

According to algorithm A24, changes in patient laboratory blood test results (plasmatic coagulation factor function and plasmatic drug levels), viscoelastic test output, thrombocyte function tests, patient monitoring vital signs, patient diagnoses and characteristics lead to a change in the color of the blood drops and pool of blood indicators or part 5 of the visual blood clot model 101 following an ease in ease out function. The ease in/out function causes very low and very high values of input coagulation function parameters to cause more extensive changes in color of fibrin mesh compared to normal and less low and less high input parameter values. This function serves to enable users to detect low and high-extremes. FIG. 26 provides a schematic overview of this algorithm. For specific pre-defined diagnoses and characteristics stored in memory, the algorithms create specific changes in the color of blood drops and pool of blood indicators, also stored in memory.

Examples: The input: "high crystalloid volume substitution" causes the algorithm to show a less intense color of the blood drops 46 and pool of blood indicators 45 (e.g., HEX color: #EDDBD5), compared to the input normal quick value (e.g., HEX color: #FF0000) 46, 47.

Visual Blood Clot Algorithm A25 (Display of Specific Blood Drops and Pool of Blood Indicators Labels)

This algorithm is used to make part 5 (FIG. 1) of the visual blood clot model 101 (blood drops and pool of blood indicators) appear in an individualized way, which is modeled after and has logical commonality with, the characteristics a blood clot would have in the real patient that the input data comes from. Algorithm A25 uses the following inputs, however, is not limited to these or by these, as persons skilled in the art may think of additional inputs without departing from the scope of the description: Patient laboratory blood test results (plasmatic coagulation factor function and plasmatic drug levels), viscoelastic test output, thrombocyte function tests, patient monitoring vital signs, patient diagnoses and characteristics.

Figure 27:
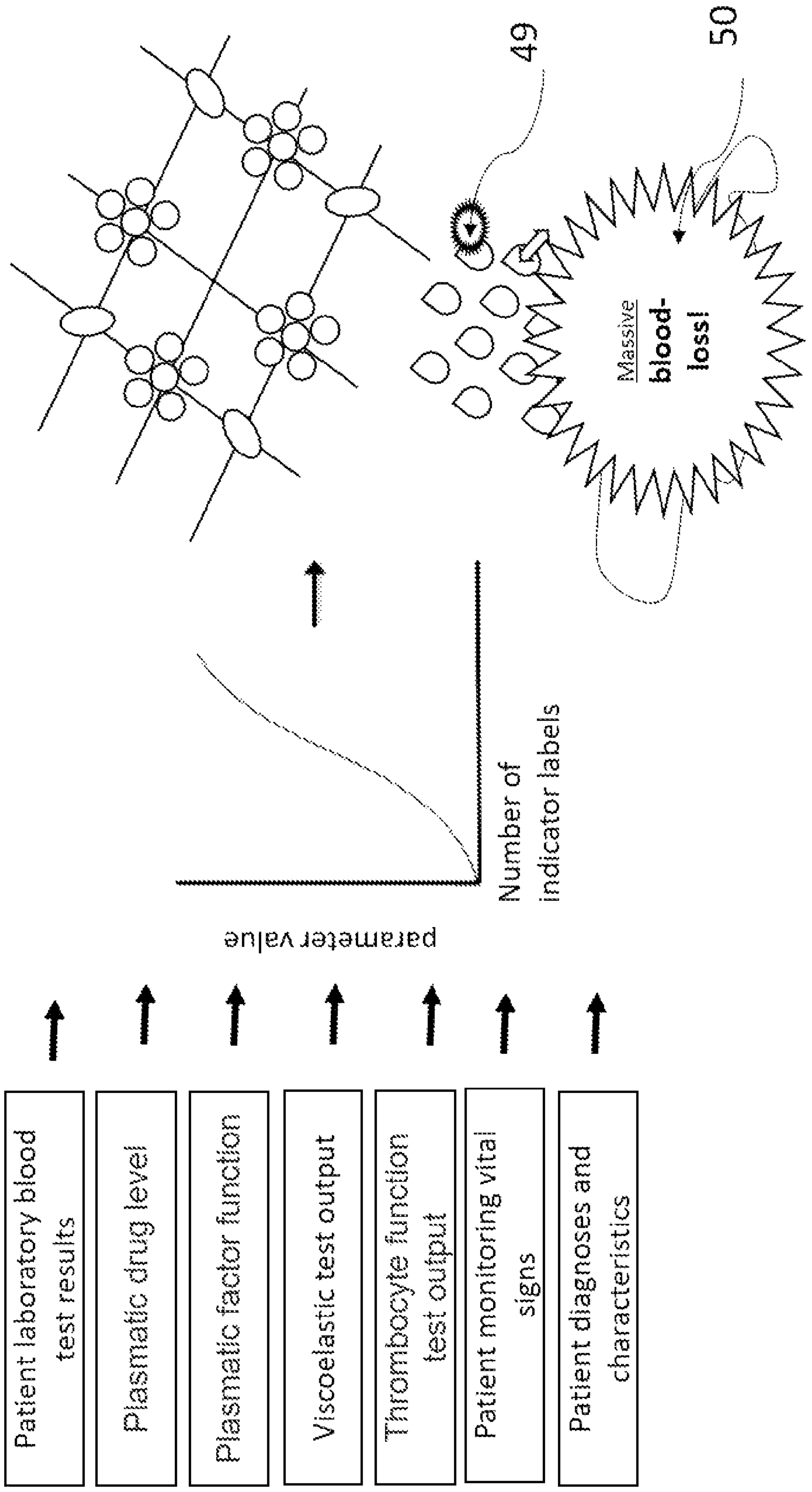

According to algorithm A25, changes in patient laboratory blood test results (plasmatic coagulation factor function and plasmatic drug levels), viscoelastic test output, thrombocyte function tests, patient monitoring vital signs, patient diagnoses and characteristics lead to a display of specific background indicator labels in part 5 (blood drops and pool of blood indicators) of the visual blood clot model 101 following an ease in ease out function. The ease in/out function causes very low and very high values of input coagulation function parameters to cause more or fewer specific blood drops and pool of blood indicators labels compared to normal and less low and less high input parameter values. This function serves to enable users to detect low and high-extremes. FIG. 27 provides a schematic overview of this algorithm. For specific pre-defined diagnoses and characteristics stored in memory, the algorithm displays specific background indicator labels, also stored in memory. These background indicator labels may be in alphanumeric format, i.e. consist of text and numbers or be two or three-dimensional graphical indicators.

Example 1) The input: "massive blood loss" from the patient data management system causes the algorithm to show specific blood drops 49 and pool of blood indicators 50.

Visual Blood Clot Algorithm A26 (Volume [3D] and Area [2D] of Thrombocyte Indicators) and Algorithm A27 (Form of Thrombocyte Indicators)

These algorithms are used to make part 6 (FIG. 1) of the visual blood clot model 101 (thrombocyte indicators) appear in an individualized way, which is modeled after and has logical commonality with, the characteristics a blood clot would have in the real patient that the input data comes from. Algorithms A26 and A27 use the following inputs, however, are not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 28:
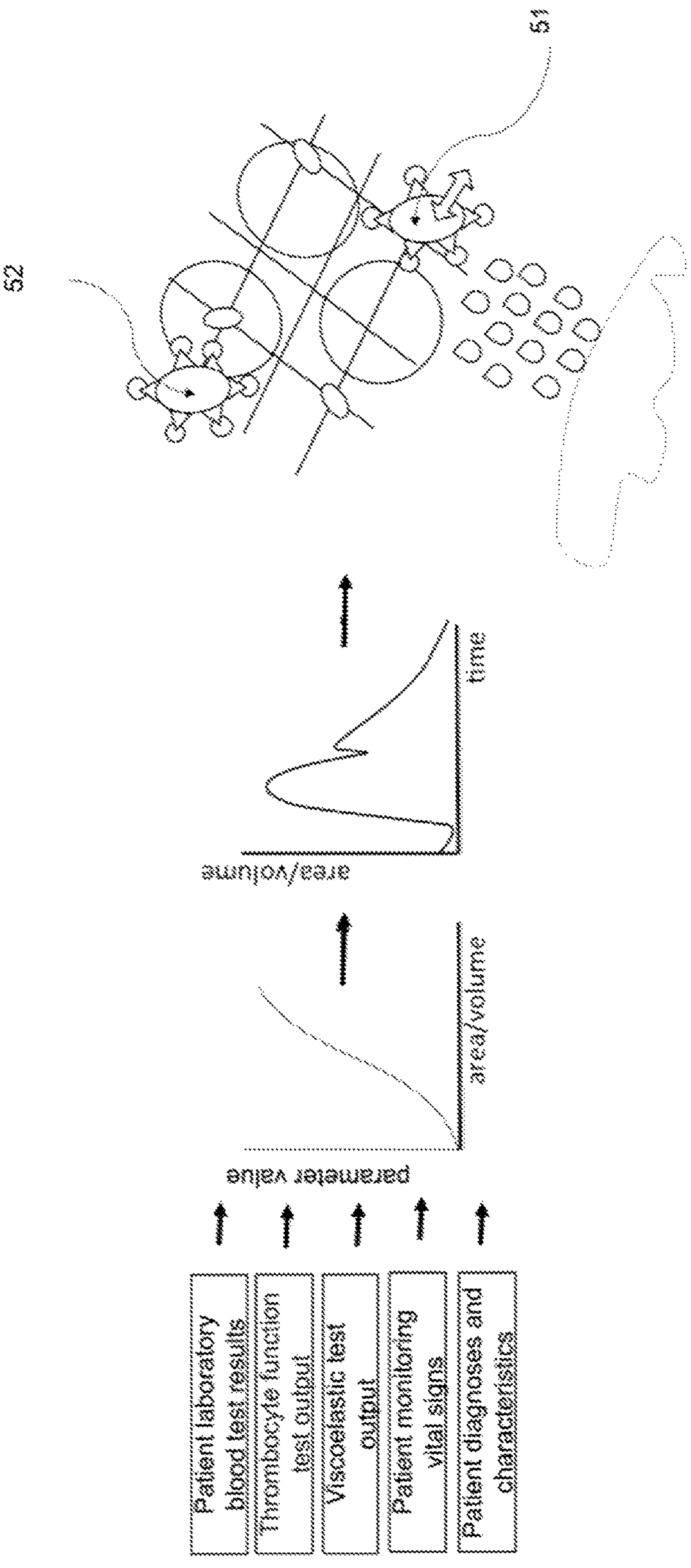

According to algorithms A26 and A27, changes in patient laboratory blood test results (plasmatic coagulation factor function), viscoelastic test output, patient monitoring vital signs, patient diagnoses and characteristics lead to a change in volume (3D) or area (2D) of the blood drops and pool of blood indicators shown in the visual blood clot model 101 following an ease in ease out function. The ease in/out function causes very low and very high values of input coagulation function parameters to cause more extensive changes in volume or area of parts (3D) or area (2D) of thrombocyte indicators compared to normal and less low and less high input parameter values. This function serves to enable users to detect low and high-extremes. FIG. 28 provides a schematic overview of these algorithms. For specific pre-defined diagnoses and characteristics stored in memory, the algorithms create specific changes in volume (3D), area (2D), or form of the thrombocyte indicators, also stored in memory. Depending on specific vital sign values or patient characteristics, the thrombocyte indicators can change their volume or area according to vital values, as for example:

Examples 1) The input "high MCF in EXTEM" causes the algorithm to change the form of thrombocyte indicators to appear activated (podocytes) 52 and large 51. 2) The input "high thrombocyte count" causes to thrombocytes to appear large and activated 52.

Visual Blood Clot Algorithm A28 (Color of Thrombocyte Indicators Displayed)

This algorithm is used to make part 6 (FIG. 1) of the visual blood clot model 101 (thrombocyte indicators) appear in an individualized way, which is modeled after and has logical commonality with, the characteristics a blood clot would have in the real patient that the input data comes from. Algorithm A28 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 29:
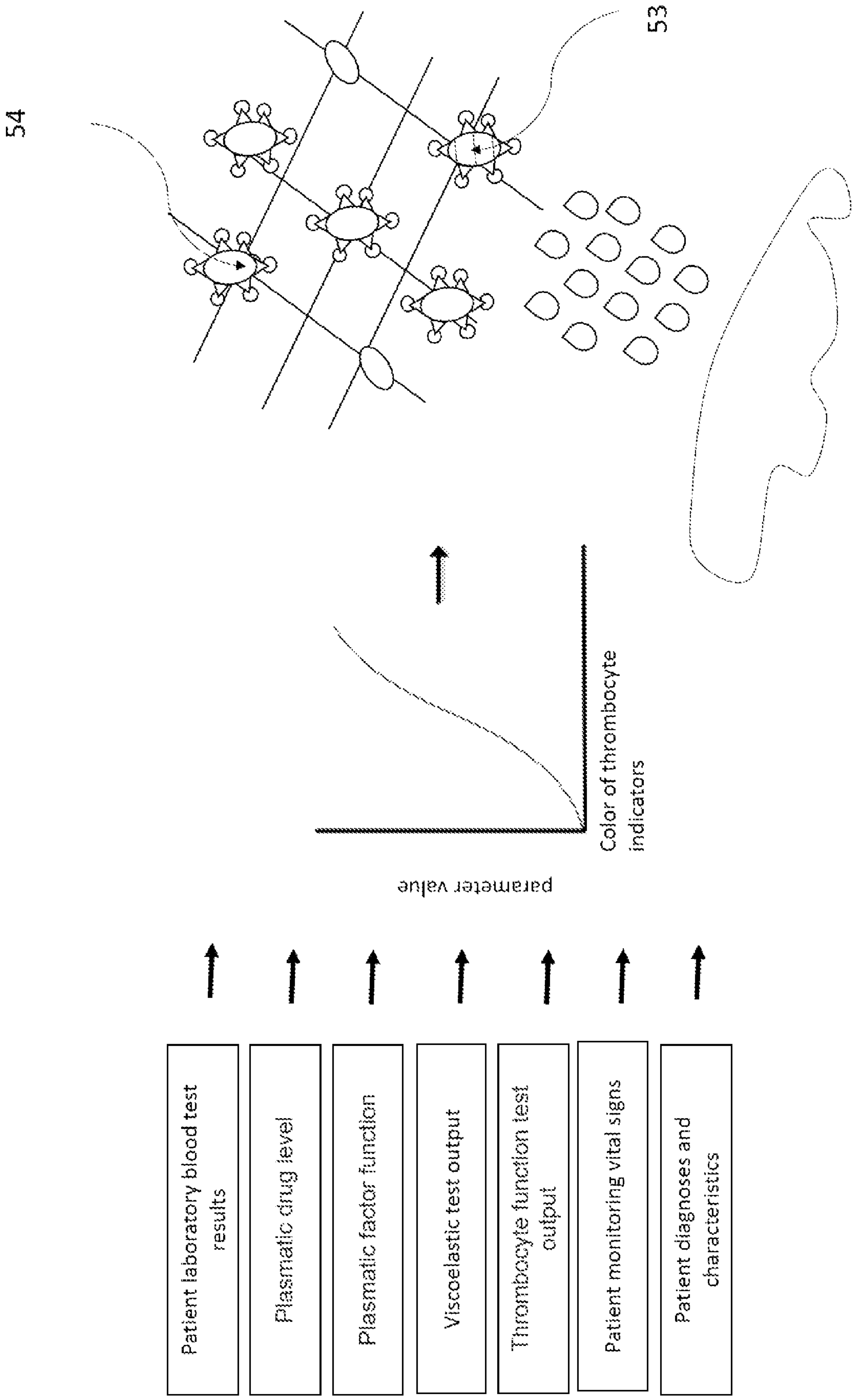

According to algorithm A28, changes in patient laboratory blood test results (plasmatic coagulation factor function), viscoelastic test output, patient monitoring vital signs, patient diagnoses and characteristics lead to a change in the color of the thrombocyte indicators or part 6 of the visual blood clot model 101 following an ease in ease out function. The ease in/out function causes very low and very high values of input coagulation function parameters to cause more extensive changes in color of fibrin mesh compared to normal and less low and less high input parameter values. This function serves to enable users to detect low and high-extremes. FIG. 29 provides a schematic overview of this algorithm. For specific pre-defined diagnoses and characteristics stored in memory, the algorithms create specific changes in the color of thrombocyte indicators, also stored in memory.

Example 1) The input: "decreased thrombocyte function" causes the algorithm to show a less intense color of the thrombocyte indicators (e.g., HEX color: # #F2EEE3) 53, compared to the normal thrombocyte activity input (e.g., HEX color: #AFA787) 54.

Visual Blood Clot Algorithm A29 (Number of Thrombocyte Indicators Displayed)

This algorithm is used to make part 6 (FIG. 1) of the visual blood clot model 101 (thrombocyte indicators) appear in an individualized way, which is modeled after and has logical commonality with, the characteristics a blood clot would have in the real patient that the input data comes from. Algorithm A29 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 30:
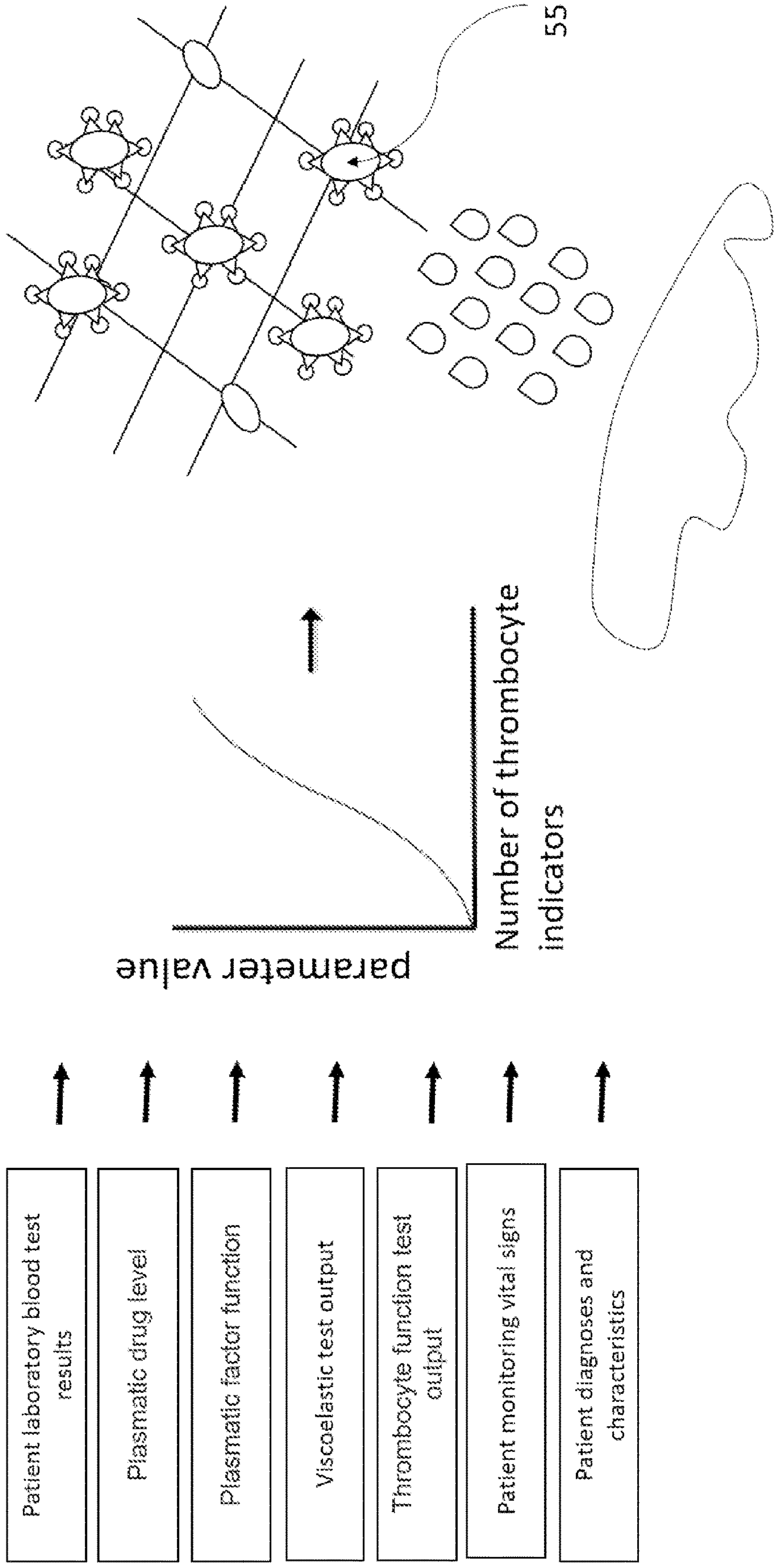

According to algorithm A29, changes in patient laboratory blood test results (plasmatic coagulation factor function), viscoelastic test output, patient monitoring vital signs, patient diagnoses and characteristics lead to a change in the number of thrombocyte indicators shown in the visual blood clot model 101 following an ease in ease out function. The ease in/out function causes very low and very high values of input coagulation function parameters to cause more extensive changes in number of thrombocyte indicators compared to normal and less low and less high input parameter values. This function serves to enable users to detect low and high-extremes. FIG. 30 provides a schematic overview of this algorithm. For specific pre-defined diagnoses and characteristics stored in memory, the algorithm creates specific changes in the number of displayed thrombocyte indicators, also stored in memory.

Example 1: The input: "high platelet count" causes the algorithm to increase the number of thrombocyte indicators 55 displayed.

Visual Blood Clot Algorithm A30 (Display of Specific Thrombocyte Indicator Labels)

This algorithm is used to make part 6 (FIG. 1) of the visual blood clot model 101 (thrombocyte indicators) appear in an individualized way, which is modeled after and has logical commonality with, the characteristics a blood clot would have in the real patient that the input data comes from. Algorithm A30 uses the following inputs, however, is not limited to these or by these, as persons skilled in the art may think of additional inputs without departing from the scope of the description: Patient laboratory blood test results (plasmatic coagulation factor function), viscoelastic test output, patient monitoring vital signs, patient diagnoses and characteristics.

Figure 31:
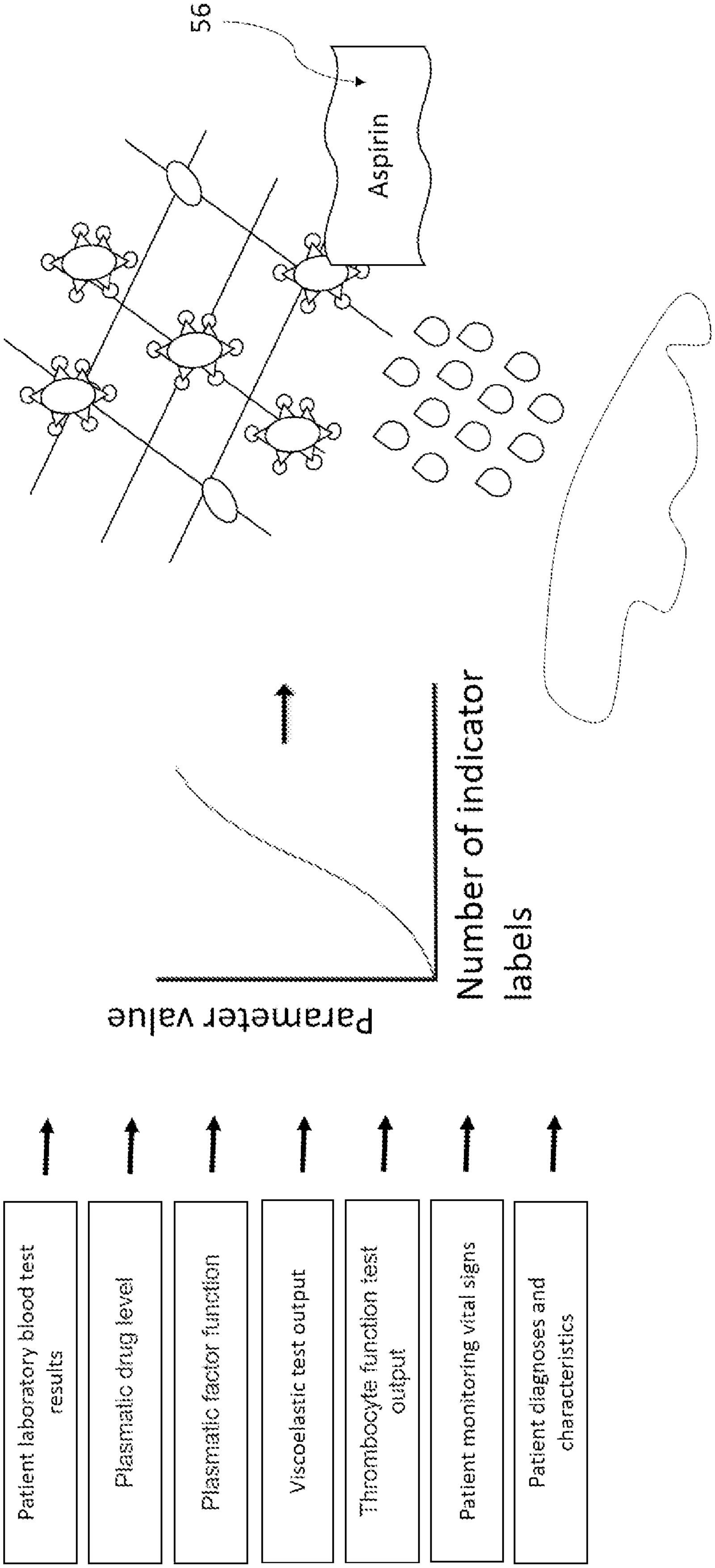

According to algorithm A30, changes in patient laboratory blood test results (plasmatic coagulation factor function), viscoelastic test output, patient monitoring vital signs, patient diagnoses and characteristics lead to a display of specific background indicator labels in part 6 (thrombocyte indicators) of the visual blood clot model 101 following an ease in ease out function. The ease in/out function causes very low and very high values of input coagulation function parameters to cause more or fewer specific blood drops and pool of blood indicators labels compared to normal and less low and less high input parameter values. This function serves to enable users to detect low and high-extremes. FIG. 31 provides a schematic overview of this algorithm. For specific pre-defined diagnoses and characteristics stored in memory, the algorithm displays specific thrombocyte indicator labels, also stored in memory. These background indicator labels may be in alphanumeric format, i.e. consist of text and numbers or be two or three-dimensional graphical indicators.

Example 1) The input: "Aspirin effect" causes the algorithm to show specific indicator labels over the thrombocyte indicators to indicate the presence of an Aspirin effect on thrombocytes 56.

Empirical Evidence for the Functionality of the Described Technology

This section provides the results of an extensive, international multi-center study that clearly demonstrated the functionality of the Visual Clot technology described above. A preferred embodiment of the Visual Clot technology was compared to the current state-of-the-art in viscoelastic test outputs (i.e., ROTEM technology, Instrumentation Laboratory, Bedford, MA, U.S.A.)

Analyzing 349 within-subject comparisons of therapeutic decisions after Visual Clot and ROTEM based presentation, we found that every single participating physician was able to make more correct decisions with the Visual Clot—regardless of previous experience with ROTEM. Overall, while with the conventional ROTEM display only 47% of therapeutic decisions were correct, with the Visual Clot it was 100%. This increase in correct decision-making was accompanied by quicker decision times, and lower perceived workload. Participants were also more confident in their decision.

Methods

Participants & Trial Design

This study was an investigator-initiated, within-subject, prospective, multicenter trial comparing two different ways to display ROTEM results. The ethics committee of the canton of Zurich issued a clarification of responsibility, declaring that the study does not require their approval (BASEC-Nr. Req-2018-00933). The study was conducted with a total of 60 anesthesiologists and intensivists in two large tertiary care hospitals experienced in ROTEM use: Half of the participants came from the University Hospital Zurich in Switzerland and the other half from the University Hospital Frankfurt in Germany. The selection of participants was random, as anesthesiologists and intensivists were invited during daily clinical practice in the operating ward or intensive care unit to take part in the study—regardless of gender, age, degree, position or ROTEM experience.

Setting

After signing an informed consent and completing a short demographic survey, participants were shown four introductory slides, explaining both the Visual Clot and the traditional ROTEM display. They were then shown 12 scenarios in randomized sequences. Randomization of the sequences was done by Research Randomizer Version 4.0 [randomizer.org, retrieved on Dec. 5, 2018). Each Visual Clot was created from a ROTEM scenario, according to the algorithm provided in Table 2 and enabling direct comparisons of matched ROTEM and Visual Clot pairs.

TABLE 2

The algorithm used to create the Visual Clots from the ROTEM scenarios

| | |
|---|---|
| Fibrin deficiency = true | IF "MCF FIBTEM" < 9 mm |
| Thrombocyte deficiency = true | IF "MCF FIBTEM" 9-25 mm AND "MCF Extern" < 40 mm OR "MCF Intern" < 40 mm<br>OR<br>IF "MCF FIBTEM" > 25 mm AND "MCF Extern" < 50 mm OR "MCF Intern" < 50 mm<br>OR<br>IF "MCF FIBTEM" < 9 mm AND "MCF Extern" < 30 mm OR "MCF Intern" < 30 mm |

TABLE 2-continued

The algorithm used to create the Visual Clots from the ROTEM scenarios

| | |
|---|---|
| | OR<br>IF "ML INTEM" > 15% OR "ML EXTEM" > 15% OR "ML FIBTEM" > 15% AND "MCF APTEM" < 30 mm |
| Plasmatic factor deficiency = true | IF "CT EXTEM" > 79 sec OR "CT INTEM" > 240 sec AND "Fibrin deficiency" = false AND "Thrombocyte deficiency" = false AND "Hyperfibrinolysis" = false AND "Hypercoagulability" = false AND "Heparin effect" = false<br>OR<br>IF "CT EXTEM" > 100 sec OR "CT INTEM" > 260 sec. |
| Hyperfibrinolysis = true | IF "ML EXTEM" > 15% OR "ML INTEM" > 15% OR "ML FIBTEM" > 15% AND "ML APTEM" < 15% |
| Hypercoagulability = true | IF "MCF EXTEM" > 72 mm or "MCF INTEM" > 72 mm |
| Heparin effect = true | IF "CT INTEM" > 240 sec AND "CT HEPTEM" < 240 sec |

In a within-subject design for direct comparison, the 12 scenarios always consisted of six matched pairs of Visual Clot and ROTEM images. The different scenarios with their correct solutions are available as Supplemental Appendix. Each Visual Clot was created from a ROTEM scenario, enabling direct comparisons of matched ROTEM and Visual Clot pairs. The scenarios were shown on an Acer Aspire V15 Nitro laptop (Acer Inc., New Taipei City, Taiwan) and the participants gave their corresponding answers on an iPad-(Apple Inc., Cupertino, CA, U.S.A.) and iSurvey-based (Harvest Your Data, Wellington, New Zealand) data collection tool.(14) For each scenario the question "If there are clinical signs of bleeding present, what treatment is required?" was asked, with the following possible answers: Fibrinogen, platelets, tranexamic acid (antifibrinolytic), protamine (to reverse heparin effect), plasmatic factors, nothing (normal ROTEM or hypercoagulable). Multiple answers were possible. The time it took to complete a question was measured by the data collection software in seconds. After each scenario participants then answered questions about their diagnostic confidence and their perceived workload.

Outcomes

The decision-making outcome was assessed by the percentage of correct decisions in response to different scenarios. For each scenario participants would reach the maximum score of 1 per scenario if they picked all necessary, but no incorrect treatments (e.g. 1 out of 1 correct answer results in 1 point, or 3 out of 3 answers results in 1 point). Scenarios could also be answered partially correct (e.g. 2 out of 3 answers results in 0.667 points). For each incorrect treatment selected, a score would be deducted equivalent to one correct answer in this scenario (e.g. 1/1 correct answer with 1 wrong answer results in 0 points, 2/2 correct answers with 1 wrong answer results in 0.5 points). The participant's final outcome was the percentage reached of the maximum possible score. Time-to-decision was measured in seconds.

Diagnostic confidence was assessed after each scenario on a 4-point Likert scale (0=very unconfident, 1=unconfident, 2=confident, 3=very confident). Workload was also evaluated after each scenario by the National Aeronautics and Space Administration Task Load Index (NASA-TLX). The NASA-TLX consisted of only five questions, as the otherwise sixth question on "physical demand" was removed for the purpose of this study.

Experience in the interpretation with ROTEM was assessed by the ROTEM experience score, which was calculated from each participant's years of clinical experience multiplied the number of ROTEM interpreted in the last year.

Statistical Analysis

Distribution of variables is expressed using medians and interquartile ranges (IQR) regardless of normality. Normality was assessed with the Shapiro-Wilks test and visual inspection of quantile-quantile plots of dependent variables. Group differences between the Visual Clot and ROTEM were then assessed by paired t-test for normally distributed data or by Wilcoxon matched-pairs signed-ranks test for non-normally distributed data. Group differences were calculated for decision-making, time to decision, perceived workload and NASA-TLX. Association of ROTEM experience and successful decision-making, as well as association of self-rated ROTEM skill and successful decision-making, was assessed by Spearman's correlation.

All analyses were carried out and figures created in GraphPad PRISM 8.1.1. (GraphPad Software Inc., CA, U.S.A.). A p-value of less than 0.05 was considered to indicate statistical significance.

Results

Participants

From Dec. 6, 2018 to Apr. 17, 2019, 30 anesthesiologists and intensivists from each study center were recruited. All 60 participants rated six matched pairs of ROTEM and Visual Clot scenarios, resulting in a total of 360 direct comparisons. 11 paired scenarios were excluded after completion because of an error in the display.

The participants from the University Hospital Frankfurt were more experienced than the ones from the University Hospital Zurich, with a median experience of 9 years (IQR 6 to 12) compared to 5 years (IQR 2 to 10). Consequently, physicians from the University Hospital Frankfurt also interpret more ROTEMs (52 per year, IQR 19 to 56) than at the University Hospital Zurich (20 per year, IQR 7 to 50) (Table 3).

TABLE 3

Study and participant characteristics.

| | |
|---|---|
| Number of participants: | 60 |
| Number of different ROTEM cases rated: | 11 |
| Number of direct comparisons between ROTEM and Visual Clot | 349 |

TABLE 3-continued

Study and participant characteristics.

| | USZ (Zurich) | UKF (Frankfurt) |
|---|---|---|
| Study duration | 132 days (Dec. 6th, 2018 - Apr. 17th, 2019) | 53 days (Feb. 18th - Apr. 12th, 2019) |
| Number of participants at study site | 30 | 30 |
| Sex (female) participants (%) | 14 (47) | 9 (30) |
| Participants position | | |
| Senior physician (%) | 14 (47) | 21 (70) |
| Resident physician (%) | 16 (53) | 9 (30) |
| Median anesthesia experience of physicians in years (IQR) | 5 (2-10) | 9 (6-1.2) |
| Median number of ROTEMS interpreted by physicians per year (IQR) | 20 (7-50) | 52 (19-56) |
| Median duration per data collection in minutes (IQR) | 22 (20-26) | 20 17-22) |

Decision Making

Figure 32:
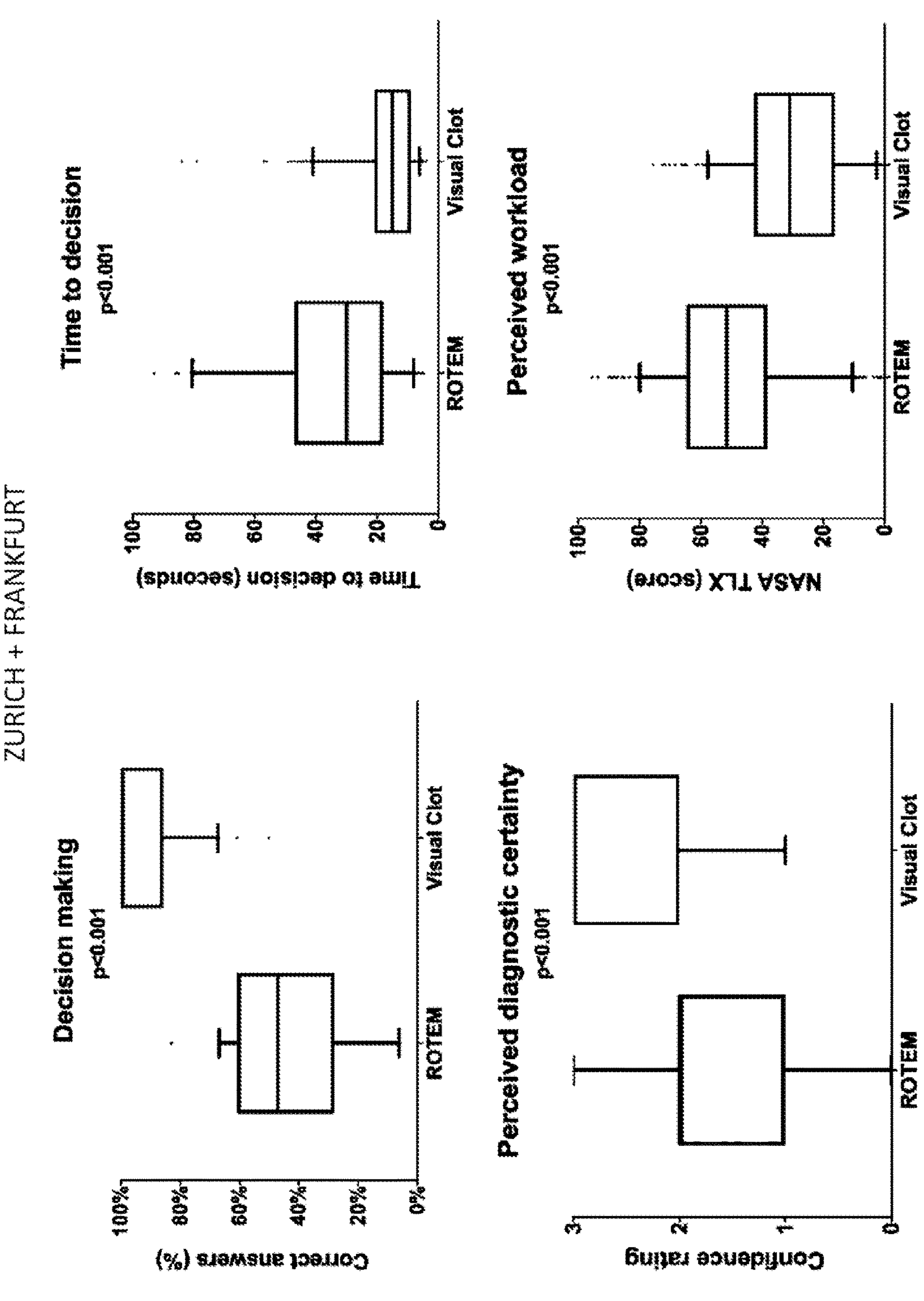
FIG. 32: Overall group differences between the conventional ROTEM display and the Visual Clot.

FIG. 32 illustrates overall group differences between the conventional ROTEM display and the Visual Clot. Box plots are medians with interquartile range, whiskers are 5-95 percentile, dots are individual outliers. Perceived diagnostic confidence: 0=very unconfident, 1=unconfident, 2=confident, 3=very confident. Perceived workload: NASA=National Aeronautics and Space Association, TLX=Task Load Index. N for decision making=60, N for time to decision, perceived diagnostic certainty, perceived workload=349.

Overall median percentage of correct therapeutic decisions was 47% (IQR 28 to 61) for all traditional ROTEMs scenarios, compared to 100% (IQR 86 to 100) for Visual Clot scenarios. Wilcoxon matched-pairs signed rank test determined the Visual Clot to enable significantly better decision-making (p<0.001) (cf. FIG. 32).

Median time to decision with the Visual Clot was 15 seconds (IQR 9 to 21) and was significantly faster than the 30 seconds (IQR 18 to 47) it took with the conventional ROTEM (p<0.001) (cf. FIG. 32).

Figure 33:
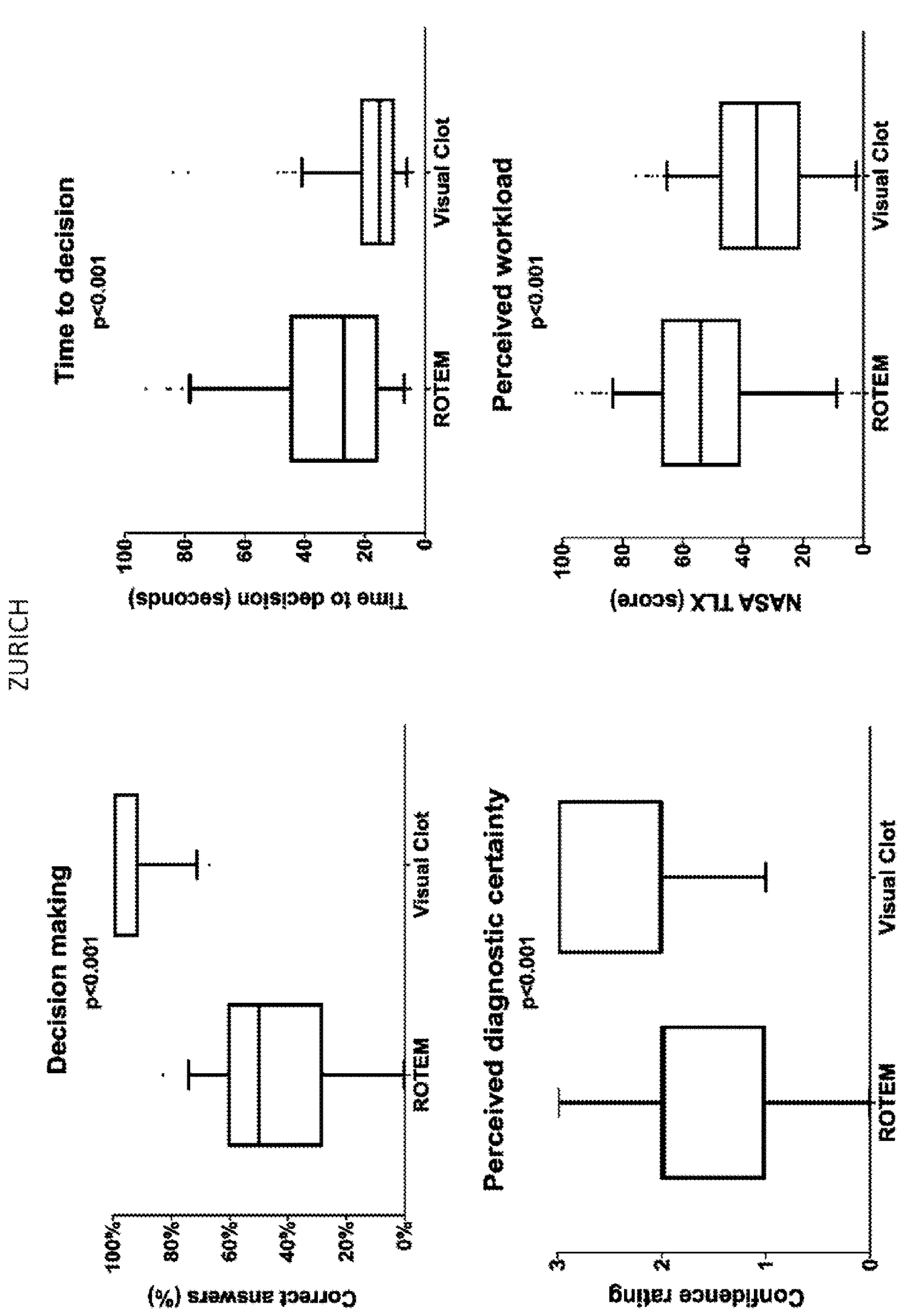
FIG. 33: Group differences between the conventional ROTEM display and the Visual Clot for Center Zurich.
Figure 34:
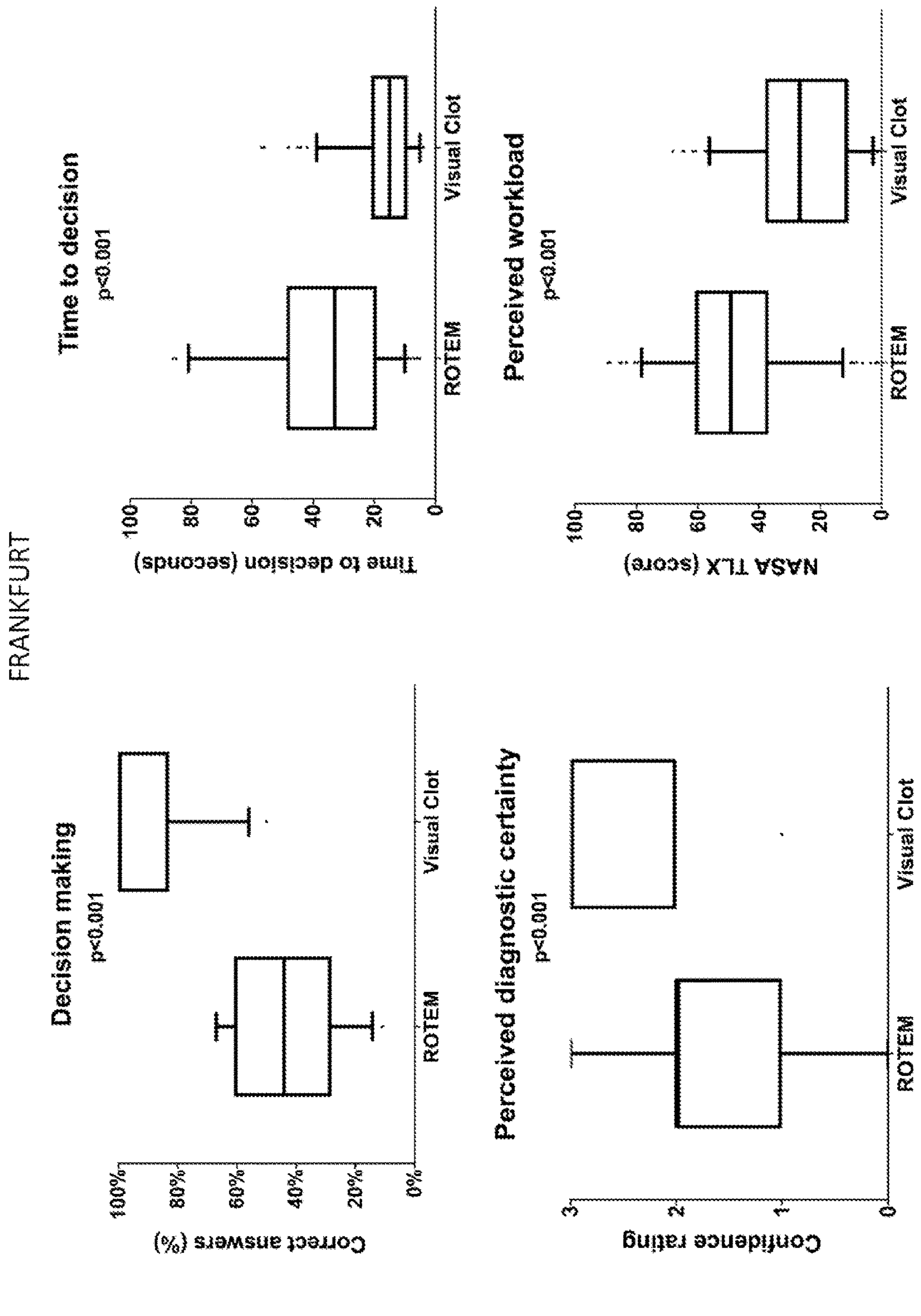
FIG. 34: Group differences between the conventional ROTEM display and the Visual Clot for Center Frankfurt.

Perceived workload was also significantly lower with the Visual Clot than with ROTEM, with median NASA-TLX scores of 31 (IQR 16 to 43) and 52 (IQR 38 to 65) respectively (p<0.001) (cf. FIG. 32). Participants rated their diagnostic confidence to be higher with the Visual Clot (median "3=very confident", IQR "2=confident" to "3=very confident") than with the ROTEM (median "2=confident", IQR "1=unconfident" to "3=very confident") (p<0.001) (cf. FIG. 32). The separate results for study center Zurich only are shown in FIG. 33, the separate results for study center Frankfurt only, in FIG. 34.

Figure 35:
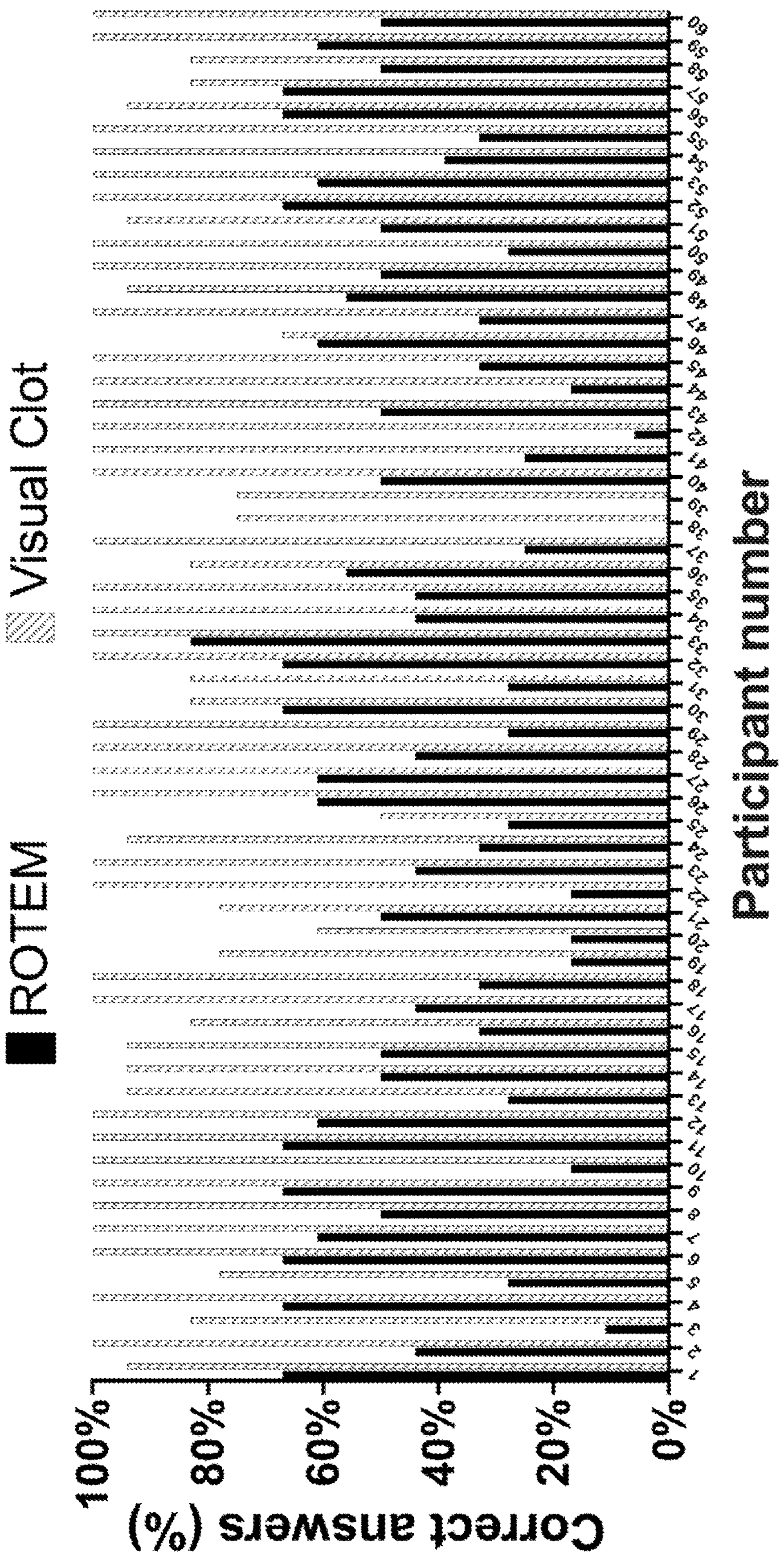
FIG. 35: Decision-making on an individual participant level. Percentage of correct answers for each of the 60 participants.

Participant wise analysis shows that every single participant was able to determine more correct answers regarding therapeutic decision-making with the Visual Clot than with the ROTEM (cf. FIG. 35). Further, scenario wise analysis shows that Visual Clot based decision-making is significantly superior to the conventional ROTEM in 10 out of 11 scenarios. No difference in decision-making was found for the Hyperfibrinolysis scenario (cf. Table 4).

TABLE 4

Scenario based results for both study centers. All variables are medians with interquartile range, except "participants with score of 100%," which is count and percentage. Perceived diagnostic confidence: 0 = very unconfident, 1 = unconfident, 2 = confident, 3 = very confident. Perceived workload: NASA = National Aeronautics and Space Association, TLX = Task Load Index.

| Case | ROTEM | Visual Clot | P-value |
|---|---|---|---|
| 1. Normal (10 min) n = 24 | | | |
| Decision making score | 100% (0%-100%) | 100% (100%-100%) | 0.016 |
| Participants with score of 100% | 24/24 (100%) | 17/24 (71%) | <0.001 |
| Time to decision seconds | 49 (27-65) | 12 (7-19) | <0.001 |
| Perceived diagnostic confidence | 2 (1-2) | 3 (3-3) | <0.001 |
| Perceived workload NASA TLX score | 58 (39-69) | 25 (11-35) | |
| 2. Normal (60 min) n = 36 | | | |
| Decision making score | 100% (0%-100%) | 100% (100%-100%) | <0.001 |
| Participants with score of 100% | 34/36 (95%) | 21/36 (58%) | <0.001 |
| Time to decision seconds | 18 (11-37) | 8 (6-12) | <0.001 |
| Perceived diagnostic confidence | 2 (1-3) | 3 (2-3) | <0.001 |
| Perceived workload NASA TLX score | 45 (28-55) | 25 (5-35) | |
| 3. Fibrin deficiency (10 min) n = 24 | | | |
| Decision making score | 0% (0%-0%) | 100% (100%-100%) | <0.001 |
| Participants with score of 100% | 5/24 (21%) | 22/24 (92%) | <0.001 |
| Time to decision seconds | 49 (38-56) | 19 (15-34) | <0.001 |

TABLE 4-continued

Scenario based results for both study centers. All variables are medians with interquartile range, except "participants with score of 100%," which is count and percentage. Perceived diagnostic confidence: 0 = very unconfident, 1 = unconfident, 2 = confident, 3 = very confident. Perceived workload: NASA = National Aeronautics and Space Association, TLX = Task Load Index.

| Case | ROTEM | Visual Clot | P-value |
|---|---|---|---|
| Perceived diagnostic confidence | 1 (1-2) | 2 (2-3) | <0.001 |
| Perceived workload NASA TLX score | 55 (46-67) | 33 (10-40) | |
| 4. Platelet deficiency (10 min) n = 36 | | | |
| Decision making score | 0% (0%-0%) | 100% (100%-100%) | <0.001 |
| Participants with score of 100% | 8/36 (22%) | 32/36 (89%) | <0.001 |
| Time to decision seconds | 34 (22-46) | 13 (8-18) | <0.001 |
| Perceived diagnostic confidence | 1 (1-2) | 3 (2-3) | <0.001 |
| Perceived workload NASA TLX score | 50 (41-65) | 25 (15-35) | |
| 5. Plasmatic coagulation factor deficiency (60 min) n = 36 | | | |
| Decision making score | 0% (0%-100%) | 100% (100%-100%) | <0.001 |
| Participants with score of 100% | 10/36 (28%) | 31/36 (86%) | 0.008 |
| Time to decision seconds | 27 (15-38) | 20 (15-26) | <0.001 |
| Perceived diagnostic confidence | 2 (1-2) | 2 (2-3) | <0.001 |
| Perceived workload NASA TLX score | 50 (35-65) | 43 (19-53) | |
| 6. Hyperfibrinolysis (60 min) n = 18 | | | |
| Decision making score | 100% (0%-100%) | 100% (100%-100%) | 0.38 |
| Participants with score of 100% | 13/18 (72%) | 16/18 (89%) | <0.001 |
| Time to decision seconds | 35 (22-44) | 13 (11-16) | <0.001 |
| Perceived diagnostic confidence | 2 (1-2) | 2 (2-3) | <0.001 |
| Perceived workload NASA TLX score | 56 (45-65) | 28 (15-37) | |
| 7. Heparin effect (60 min) n = 24 | | | |
| Decision making score | 0% (0%-100%) | 100% (100%-100%) | <0.001 |
| Participants with score of 100% | 10/24 (42%) | 22/24 (92%) | <0.001 |
| Time to decision seconds | 45 (29-68) | 16 (13-26) | <0.001 |
| Perceived diagnostic confidence | 2 (1-2) | 3 (2-3) | <0.001 |
| Perceived workload NASA TLX score | 53 (40-65) | 32 (14-44) | |
| 8. Hypercoaguability (10 min) n = 36 | | | |
| Decision making score | 100% (100%-100%) | 100% (100%-100%) | 0.008 |
| Participants with score of 100% | 28/36 (78%) | 36/36 (100%) | <0.001 |
| Time to decision seconds | 16 (9-36) | 10 (6-16) | <0.001 |
| Perceived diagnostic confidence | 2 (1-3) | 3 (2-3) | <0.001 |
| Perceived workload NASA TLX score | 43 (15-55) | 20 (5-40) | |
| 9. Platelet deficiency masked by high fibrin (60 min) n = 60 | | | |
| Decision making score | 0% (0%-0%) | 100% (100%-100%) | <0.001 |
| Participants with score of 100% | 2/60 (3%) | 57/60 (95%) | 0.001 |
| Time to decision seconds | 25 (13-37) | 15 (10-22) | <0.001 |
| Perceived diagnostic confidence | 2 (1-3) | 3 (2-3) | <0.001 |
| Perceived workload NASA TLX score | 50 (39-60) | 30 (15-40) | |
| 10. Comb. fibrin, platelet and plasmatic factor deficiency (60 min) n = 19 | | | |
| Decision making score | 77% (77%-100%) | 100% (100%-100%) | 0.003 |
| Participants with score of 100% | 9/19 (47%) | 17/19 (89%) | 0.003 |
| Time to decision seconds | 30 (24-43) | 23 (19-34) | 0.008 |
| Perceived diagnostic confidence | 2 (1-2) | 2 (2-3) | <0.001 |
| Perceived workload NASA TLX score | 60 (40-65) | 35 (15-55) | |
| 11. Comb. fibrin, plasmatic factor deficiency and hyperfibrinolysis (60 min) n = 36 | | | |
| Decision making score | 77% (77%-100%) | 100% (77%-100%) | <0.001 |
| Participants with score of 100% | 17/36 (47%) | 27/36 (75%) | 0.002 |

TABLE 4-continued

Scenario based results for both study centers. All variables are medians with interquartile range, except "participants with score of 100%," which is count and percentage. Perceived diagnostic confidence: 0 = very unconfident, 1 = unconfident, 2 = confident, 3 = very confident. Perceived workload: NASA = National Aeronautics and Space Association, TLX = Task Load Index.

| Case | ROTEM | Visual Clot | P-value |
|---|---|---|---|
| Time to decision seconds | 28 (19-43) | 21 (16-30) | <0.001 |
| Perceived diagnostic confidence | 2 (1-2) | 2 (2-3) | <0.001 |
| Perceived workload NASA TLX score | 55 (36-67) | 35 (15-46) | |

Correlation with ROTEM Experience

Figure 36:
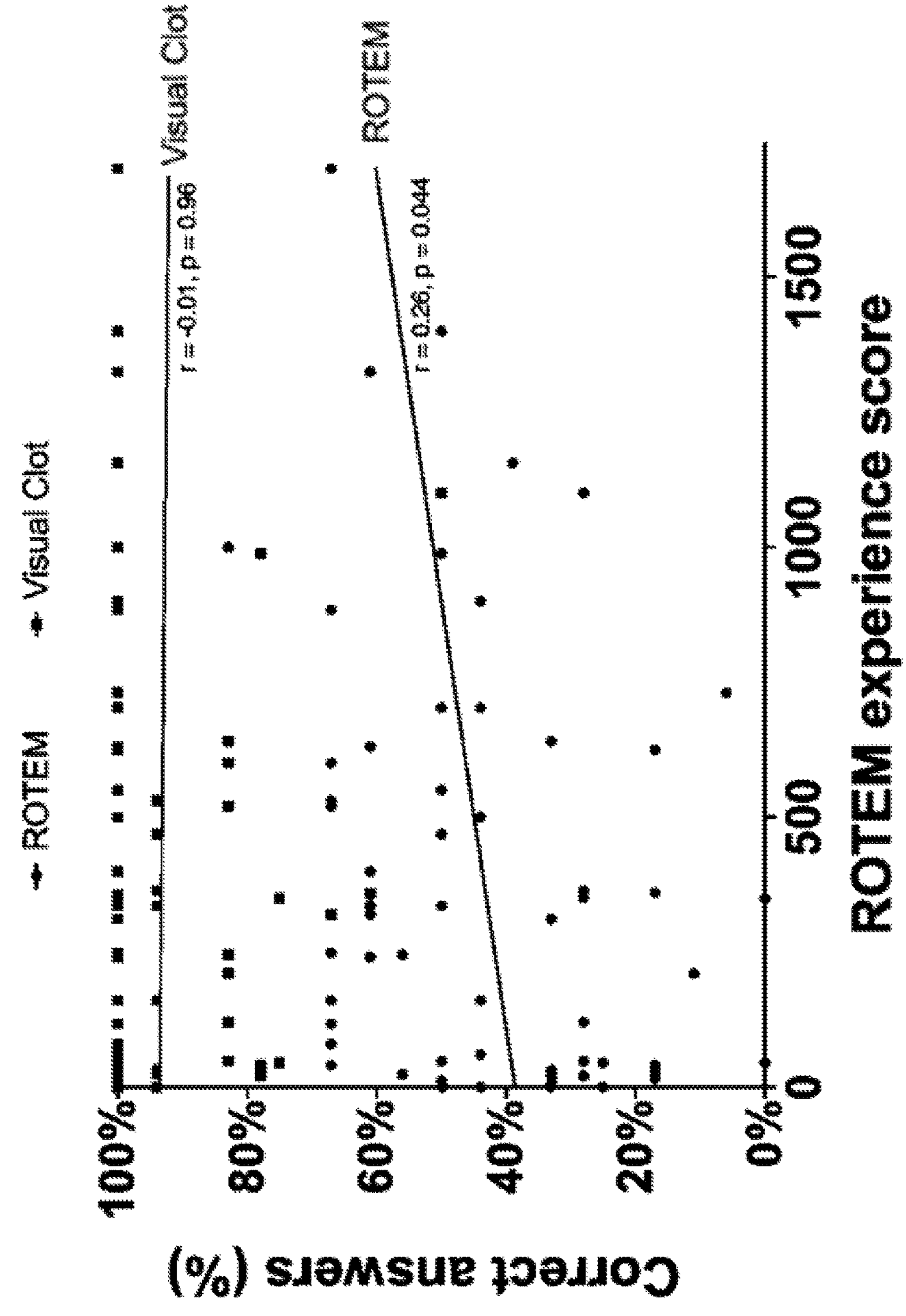
FIG. 36: Spearman's correlation of ROTEM experience and correct decisions.

A Spearman's rank-order correlation was run to assess the relationship between ROTEM experience and correct therapeutic decisions with both the conventional ROTEM display and the Visual Clot. Preliminary analysis showed the relationship to be monotonic, as assessed by visual inspection of a scatterplot. There was a statistically significant, fair positive correlation between ROTEM experience and correct therapeutic decisions with conventional ROTEM display, Spearman's correlation ($r_s(58)=0.260$, $p<0.045$). Correct therapeutic decisions based on the Visual Clot were independent from ROTEM experience, Spearman's correlation ($r_s(58)=-0.007$, $p=0.96$) (cf. FIG. 36). The ROTEM experience score is calculated from the number of ROTEM interpreted in a year multiplied the participants experience in years. N=60.

Figure 37:
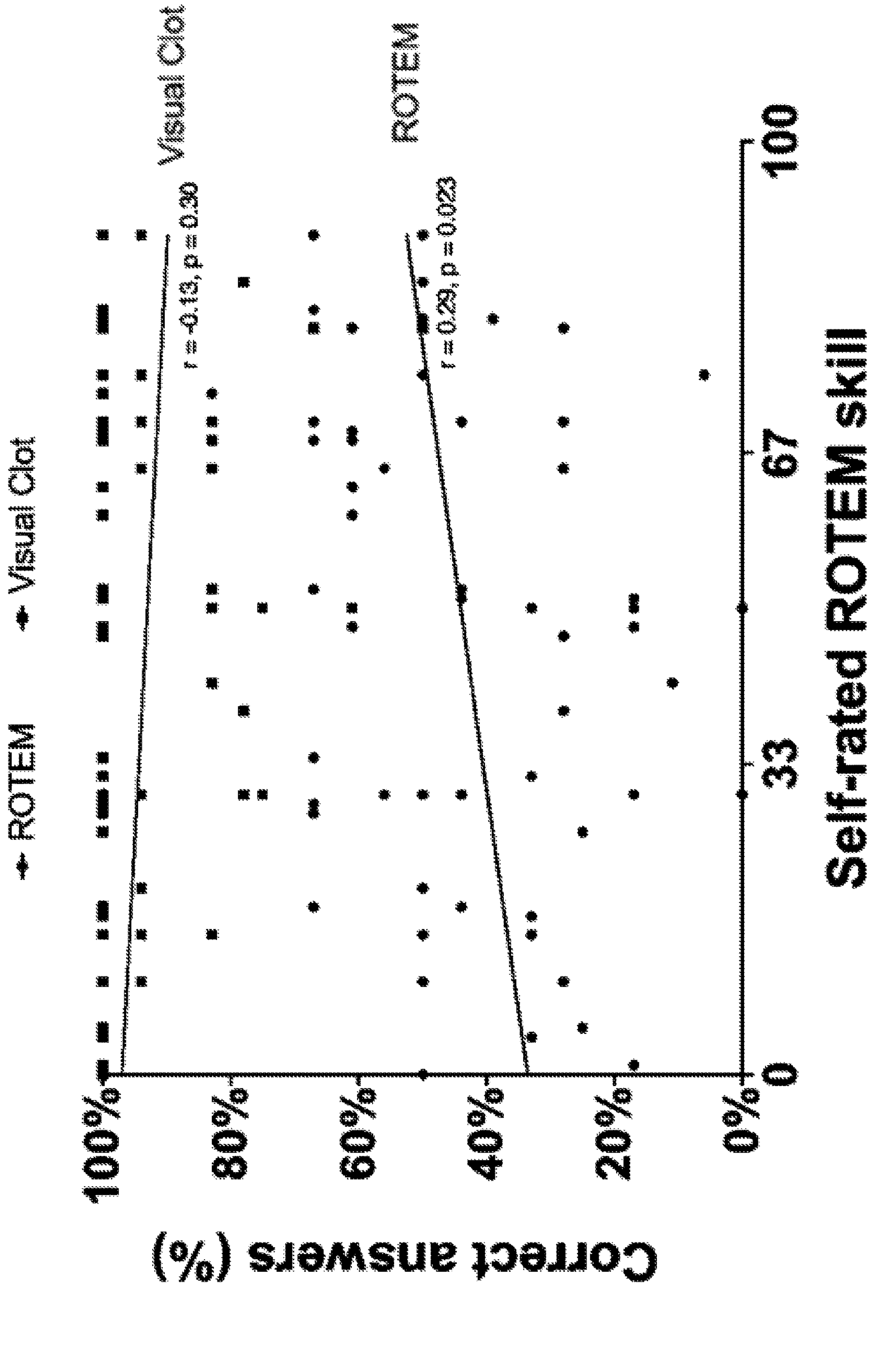
FIG. 37: Spearman's correlation of self-rated ROTEM skill and correct decisions.

Additionally, another Spearman's rank-order correlation was run to assess the relationship between self-rated ROTEM skill and correct therapeutic decisions with both the conventional ROTEM display and the Visual Clot. There was a statistically significant, fair positive correlation between self-rated ROTEM skill and correct therapeutic decisions with conventional ROTEM display ($r_s(58)=0.292$, $p<0.023$). Correct therapeutic decisions based on the Visual Clot were independent from self-rated ROTEM skill ($r_s(58)=-0.14$, $p=0.30$) with N=60. (cf. FIG. 37).

Validation of the Visual Clot

To validate the Visual Clot, the inter-rater reliability of all seven different animations used in the Visual Clot to represent different hemostatic conditions was calculated. The inter-rater-reliability of each of the seven animations or hemostatic conditions was >95% (Table 5).

TABLE 5

Inter-rater-reliability of the Visual Clot. For example, in 58 of 60 total cases, or 97%, the normal Visual Clot was correctly recognized as a normal clot.

| Hemostatic condition | Recognized (%) |
|---|---|
| Normal dot | 58/60 (97) |
| Fibrin deficiency | 75/79 (95) |
| Thrombocyte deficiency | 114/115 (99) |
| Plasmatic factor deficiency | 89/91 (97) |
| Hyperfibrinolysis | 51/54 (94) |
| Heparin effect | 24/24 (100) |
| Hypercoagulable | 18/18 (100) |

The invention claimed is:

1. A computer-implemented method for monitoring a coagulation function of a patient, the method comprising:

dynamically rendering a graphical representation of a blood clot using a synthetic two- or three-dimensional visual blood clot model, the visual blood clot model representing a real-time coagulation function status of the monitored patient, wherein the graphical representation of the blood clot includes red and white blood cells, thrombocytes, medication icons, fibrin mesh, plasmatic factors, blood drops and a pool of blood, wherein the visual blood clot model has at least one region that is allocated to at least one coagulation function quantity, and wherein the at least one region is one of the following regions:

Red blood cell indicators

Drug indicators

Thrombocyte indicators

Fibrin mesh indicators

Plasmatic factor indicators

Blood drop indicators

Pool of blood indicators, the method further comprising:

loading, from one or more coagulation function measurement devices, raw input data into a system memory wherein the raw input data includes one or more coagulation function parameters indicative of the coagulation function status of the patient;

transforming the raw input data into corresponding coagulation function quantities by using at least one ease-in-ease-out function that applies a non-linear transformation such that a degree of change in a resulting visual output attribute is non-linear relative to a degree of change in an underlying coagulation function parameter, wherein the visual attribute includes a volume or area for the respective allocated region, or a number of graphical representations of the respective allocated region, or a color value for the respective allocated region, or a particular form of graphical representations of the respective allocated region;

automatically rendering the at least one region with at least one of the resulting volume or area for the respective allocated region, the resulting number of graphical representations of the respective allocated region, the resulting color value for the respective allocated region, and the resulting form of graphical representations of the respective allocated region, depending on a current value of the at least one coagulation function quantity; and re-rendering, in real-time, the at least one region when the current value of at least one coagulation function quantity changes so that the blood clot model represents the real-time coagulation function status of the monitored patient according to the raw input data by a change of the volume or area for the respective allocated region, or by a change of the number of graphical representations of the respective allocated region, by a change of the color value for the respective allocated region, or by a change of the form of graphical representations of the respective allocated region, wherein the at least one predefined ease-in-ease-out function causes values of the one or more coagulation function parameters that deviate to a clinically significant extent to cause more extensive changes in volume/area, or number, or color value or form of the graphical representations of respective allocated regions compared to coagulation function parameters values that do not deviate to a clinically significant extent.

2. The method of claim 1, wherein the blood clot model has a plurality of regions, wherein transforming includes providing a plurality of coagulation function quantities, wherein each region is allocated to at least one coagulation function quantity of said plurality of coagulation function quantities, and wherein re-rendering includes to adjust, in real-time, any one region of the plurality of regions when the respective allocated coagulation function quantities change, thereby indicating a change of the coagulation function state of a monitored patient.

3. The method of claim 2, wherein the graphical representation of the blood clot is rendered such that it creates an impression of being looked at from a top view, wherein a point of view is a 45° angle from a bottom view with a 30° angle of tilt upwards.

4. The method of claim 1, wherein re-rendering comprises applying the particular ease-in-ease-out function to changes of coagulation function parameters in the following combination:

a) changes in patient laboratory blood test results, blood gas analysis results, or patient monitoring vital signs, leading to a change in volume or area of blood cells shown in a background of the visual blood clot model wherein the ease-in-ease-out function causes very low and very high values of input coagulation function parameters to cause more extensive changes in volume or area of parts or area of blood cells compared to normal and less low and less high input parameter values;

b) changes in patient laboratory blood test results, blood gas analysis results, Viscoelastic test output, or patient monitoring vital signs, leading to a change in a number of drug indicators shown in the visual blood clot model wherein the ease-in-ease-out function causes very low and very high values of input coagulation function parameters to cause more extensive changes in the number of drug indicators compared to normal and less low and less high input parameter values;

c) changes in patient laboratory blood test results, viscoelastic test output, or patient monitoring vital signs, leading to a change in volume or area of a fibrin mesh indicator shown in the visual blood clot model, wherein the ease-in-ease-out function causes very low and very high values of input coagulation function parameters to cause more extensive changes in the volume or area of the fibrin mesh indicator compared to normal and less low and less high input parameter values, and a low fibrin input further leading to a change of the form of the fibrin mesh indicator;

d) changes in patient laboratory blood test results, viscoelastic test output, or patient monitoring vital signs, leading to a change in volume or area of a plasmatic factor indicator shown in the visual blood clot model, wherein the ease-in-ease-out function causes very low and very high values of input coagulation function parameters to cause more extensive changes in volume or area of parts or area or the form of the plasmatic factor indicator compared to normal and less low and less high input parameter values;

e) changes in plasmatic coagulation factor function, plasmatic drug levels, viscoelastic test output, thrombocyte function tests, or patient monitoring vital signs, leading to a change in a number of blood drops and pool of blood indicators shown in the visual blood clot model, wherein the ease-in-ease-out function causes very low and very high values of input coagulation function parameters to cause more extensive changes in number of blood drops and pool of blood indicators compared to normal and less low and less high input parameter values; and f) changes in plasmatic coagulation factor function, viscoelastic test output, or patient monitoring vital signs, leading to a change in form of thrombocyte indicators shown in the visual blood clot model, wherein the ease-in-ease-out function causes very low and very high values of input coagulation function parameters to cause more extensive changes in form of thrombocyte indicators compared to normal and less low and less high input parameter values, and wherein the very high values change the form of thrombocyte indicators to appear activated.

5. The method of claim 1, wherein re-rendering comprises applying the particular ease-in-ease-out function to changes of coagulation function parameters in the following combination:

g) changes in patient laboratory blood test results, blood gas analysis results, or patient monitoring vital signs, leading to a change in volume or area of blood cells shown in a background of the visual blood clot model wherein the ease-in-ease-out function causes very low and very high values of input coagulation function parameters to cause more extensive changes in volume or area of parts or area of blood cells compared to normal and less low and less high input parameter values;

h) changes in patient laboratory blood test results, blood gas analysis results, or patient monitoring vital signs, leading to a change in volume or area of drug indicators shown in the visual blood clot model wherein the ease-in-ease-out function causes very low and very high values of input coagulation function parameters to cause more extensive changes in volume or area of parts or area of drug indicators compared to normal and less low and less high input parameter values;

i) changes in patient laboratory blood test results, viscoelastic test output, or patient monitoring vital signs, leading to a change in volume or area of a fibrin mesh indicator shown in the visual blood clot model, wherein the ease-in-ease-out function causes very low and very high values of input coagulation function parameters to cause more extensive changes in the volume or area of the fibrin mesh indicator compared to normal and less low and less high input parameter values;

j) changes in plasmatic coagulation factor function, viscoelastic test output, or patient monitoring vital signs, leading to a change in volume or area of the plasmatic factor indicator shown in the visual blood clot model, wherein the ease-in-ease-out function causes very low and very high values of input coagulation function parameters to cause more extensive changes in volume or area of parts or area of the plasmatic factor indicator compared to normal and less low and less high input parameter values;

k) changes in plasmatic coagulation factor function, plasmatic drug levels, viscoelastic test output, thrombocyte function tests, or patient monitoring vital signs, leading to a change in volume or area of the blood drops and pool of blood indicators shown in the visual blood clot model, wherein the ease-in-ease-out function causes very low and very high values of input coagulation function parameters to cause more extensive changes in volume or area of parts or area of blood drops and pool of blood indicators compared to normal and less low and less high input parameter values; and l) changes in plasmatic coagulation factor function, viscoelastic test output, or patient monitoring vital signs, leading to a change in volume or area of the blood drops and pool of thrombocyte indicators shown in the visual blood clot model, wherein the ease-in-ease-out function causes very low and very high values of input coagulation function parameters to cause more extensive changes in volume or area of parts or area of thrombocyte indicators compared to normal and less low and less high input parameter values.

6. The method of claim 1, wherein the at least one coagulation function quantity represents any one of the following quantities:

hemoglobin concentration
thrombocyte count
individual plasmatic factor function data
international normalized ratio and quick-value
activated partial thromboplastin time
drug specific anti-factor-ten-a-activity
specific plasmatic levels of drugs affecting coagulation
thrombocyte function tests
viscoelastic tests
Patient diagnoses and characteristics
Blood gas analysis results
Patient monitoring vital signs.

7. The method of claim 1, wherein re-rendering of regions of the blood clot model, based on one or more algorithms, includes using one or more further patient monitoring algorithms selected from the group of:

a. a first further algorithm wherein the area (2D) or volume (3D) of the rendered region is altered with a current value any of:
-Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
wherein said area (2D) or volume (3D) of the rendered region is re-rendered when the current value of
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
respectively changes, and wherein said area (2D) or volume (3D) of the rendered region is proportional to the current value of
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics, respectively;

b. a second further algorithm wherein the color of the rendered region is altered with a current value of:
-Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
wherein said color of the rendered region is re-rendered when the current value of
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
respectively changes, and wherein said color the rendered region is proportional to the current value of
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics, respectively;

c. a third further algorithm wherein a number of specific indicator labels shown above the rendered region is altered with a current value of:
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
wherein said number of specific indicator labels shown above the rendered region is re-rendered when the current value of
Patient laboratory blood test results
Plasmatic drug levels
Plasmatic coagulation factor function
Blood gas analysis results
Viscoelastic test outputs
Thrombocyte function test output
Patient monitoring vital signs
Patient diagnoses and characteristics
respectively changes and wherein said number of specific indicator labels shown above the rendered region is proportional to the current value of
Patient laboratory blood test results
Plasmatic drug levels
Plasmatic coagulation factor function
Blood gas analysis results
Viscoelastic test outputs
Thrombocyte function test output
Patient monitoring vital signs Patient diagnoses and characteristics, respectively.

8. The method of claim 1, wherein the two- or three-dimensional blood clot model is computed by using an individualized blood clot model being a blood clot model tailored to the coagulation function parameters of an individual patient, session trend information providing a monitoring session history, and model animations to be performed on the individual blood clot model.

9. The method of claim 1, wherein re-rendering of the at least one region occurs at a first re-rendering frequency associated with a first simplified state when a current value of the at least one coagulation function quantity falls into a first range of coagulation function quantities associated with the first simplified coagulation function state, and occurs at a second re-rendering frequency associated with a second simplified state when the current value of the at least one coagulation function monitoring quantity falls into a second range of coagulation function quantities associated with the second simplified state, wherein the first and second simplified states include predefined coagulation conditions stored in memory, and the at least one coagulation function quantity is associated with a simplified state when the current value of the at least one coagulation function quantity falls within a predefined range or threshold for a corresponding one of the predefined coagulation conditions.

10. A computer program product for monitoring a coagulation function of a patient, the computer program product comprising a non-transitory computer-readable medium storing program code that is adapted, when executed on a computer, to:

dynamically render a graphical representation of a blood clot using a synthetic two- or three-dimensional visual blood clot model, the visual blood clot model representing a real-time coagulation function status of the monitored patient, wherein the graphical representation of the blood clot includes red and white blood cells, thrombocytes, medication icons, fibrin mesh, plasmatic factors, blood drops and a pool of blood, wherein the visual blood clot model has at least one region that is allocated to at least one coagulation function quantity, and wherein the at least one region is one of the following regions:

Red blood cell indicators
Drug indicators
Thrombocyte indicators
Fibrin mesh indicators
Plasmatic factor indicators
Blood drop indicators
Pool of blood indicators, and further wherein the program code, when executed on a computer, causes the computer to:

load, from one or more coagulation function measurement devices, raw input data into a system memory wherein the raw input data includes one or more coagulation function parameters indicative of the coagulation function status of the patient;

transform the raw input data into corresponding coagulation function quantities by using at least one ease-in-ease-out function that applies a non-linear transformation such that a degree of change in a resulting visual output attribute is non-linear relative to a degree of change in an underlying coagulation function parameter, wherein the visual attribute includes a volume or area for the respective allocated region, or a number of graphical representations of the respective allocated region, or a color value for the respective allocated region, or a particular form of graphical representations of the respective allocated region;

automatically render the at least one region with at least one of the resulting volume or area for the respective allocated region, the resulting number of graphical representations of the respective allocated region, the resulting color value for the respective allocated region, and the resulting form of graphical representations of the respective allocated region, depending on a current value of the at least one coagulation function quantity; and re-render, in real-time, the at least one region when the current value of at least one coagulation function quantity changes so that the blood clot model represents the real-time coagulation function status of the monitored patient according to the raw input data by a change of the volume or area for the respective allocated region, or by a change of the number of graphical representations of the respective allocated region, by a change of the color value for the respective allocated region, or by a change of the form of graphical representations of the respective allocated region, wherein the at least one predefined ease-in-ease-out function causes values of the one or more coagulation function parameters that deviate to a clinically significant extent to cause more extensive changes in volume/area, or number, or color value or form of the graphical representations of respective allocated regions compared to coagulation function parameters values that do not deviate to a clinically significant extent.

11. The computer program product of claim 10, wherein the blood clot model has a plurality of regions, wherein transforming the raw input data includes providing a plurality of coagulation function quantities, wherein each region is allocated to at least one coagulation function quantity of said plurality of coagulation function quantities, and wherein re-rendering the at least one region includes to adjust, in real-time, any one region of the plurality of regions when the respective allocated coagulation function quantities change, thereby indicating a change of the coagulation function state of the monitored patient.

12. The computer program product of claim 10, wherein the two- or three-dimensional blood clot model is computed by using an individualized blood clot model being a blood clot model tailored to the coagulation function parameters of an individual patient, session trend information providing a monitoring session history, and model animations to be performed on the individual blood clot model.

13. The computer program product of claim 10, wherein re-rendering of the at least one region occurs at a first re-rendering frequency associated with a first simplified state when a current value of the at least one coagulation function quantity falls into a first range of coagulation function quantities associated with the first simplified coagulation function state, and occurs at a second re-rendering frequency associated with a second simplified state when the current value of the at least one coagulation function monitoring quantity falls into a second range of coagulation function quantities associated with the second simplified state, wherein the first and second simplified states include predefined coagulation conditions stored in memory, and the at least one coagulation function quantity is associated with a simplified state when the current value of the at least one coagulation function quantity falls within a predefined range or threshold for a corresponding one of the predefined coagulation conditions.

14. A computer system for monitoring a coagulation state of a patient, wherein the system comprises:

a central processing unit;

a memory;

a graphics processor; and a display device, wherein the computer system is configured to dynamically render a graphical representation of a blood clot using a synthetic two- or three-dimensional visual blood clot model, the visual blood clot model representing a real-time coagulation function status of the monitored patient, wherein the graphical representation of the blood clot includes red and white blood cells, thrombocytes, medication icons, fibrin mesh, plasmatic factors, blood drops and a pool of blood, wherein the visual blood clot model has at least one region that is allocated to at least one coagulation function quantity, and wherein the at least one region is one of the following regions:

Red blood cell indicators

Drug indicators

Thrombocyte indicators

Fibrin mesh indicators

Plasmatic factor indicators

Blood drop indicators

Pool of blood indicators, and further wherein the computer system is configured to load, from one or more coagulation function measurement devices, raw input data into a system memory wherein the raw input data includes one or more coagulation function parameters indicative of the coagulation function status of the patient;

transform the raw input data into corresponding coagulation function quantities by using at least one ease-in-ease-out function that applies a non-linear transformation such that a degree of change in a resulting visual output attribute is non-linear relative to a degree of change in an underlying coagulation function parameter, wherein the visual attribute includes a volume or area for the respective allocated region, or a number of graphical representations of the respective allocated region, or a color value for the respective allocated region, or a particular form of graphical representations of the respective allocated region;

automatically render the at least one region with at least one of the resulting volume or area for the respective allocated region, the resulting number of graphical representations of the respective allocated region, the resulting color value for the respective allocated region, and the resulting form of graphical representations of the respective allocated region, depending on a current value of the at least one coagulation function quantity; and re-render, in real-time, the at least one region when the current value of at least one coagulation function quantity changes so that the blood clot model represents the real-time coagulation function status of the monitored patient according to the raw input data by a change of the volume or area for the respective allocated region, or by a change of the number of graphical representations of the respective allocated region, by a change of the color value for the respective allocated region, or by a change of the form of graphical representations of the respective allocated region, wherein the at least one predefined ease-in-ease-out function causes values of the one or more coagulation function parameters that deviate to a clinically significant extent to cause more extensive changes in volume/area, or number, or color value or form of the graphical representations of respective allocated regions compared to coagulation function parameters values that do not deviate to a clinically significant extent.

15. The computer system of claim 14, wherein the blood clot model has a plurality of regions, wherein transforming the raw input data includes providing a plurality of coagulation function quantities, wherein each region is allocated to at least one coagulation function quantity of said plurality of coagulation function quantities, and wherein re-rendering the at least one region includes to adjust, in real-time, any one region of the plurality of regions when the respective allocated coagulation function quantities change, thereby indicating a change of the coagulation function state of the monitored patient.

16. The computer system of claim 14, wherein the two- or three-dimensional blood clot model is computed by using an individualized blood clot model being a blood clot model tailored to the coagulation function parameters of an individual patient, session trend information providing a monitoring session history, and model animations to be performed on the individual blood clot model.

17. The computer system of claim 14, wherein re-rendering of the at least one region occurs at a first re-rendering frequency associated with a first simplified state when a current value of the at least one coagulation function quantity falls into a first range of coagulation function quantities associated with the first simplified coagulation function state, and occurs at a second re-rendering frequency associated with a second simplified state when the current value of the at least one coagulation function monitoring quantity falls into a second range of coagulation function quantities associated with the second simplified state, wherein the first and second simplified states include predefined coagulation conditions stored in memory, and the at least one coagulation function quantity is associated with a simplified state when the current value of the at least one coagulation function quantity falls within a predefined range or threshold for a corresponding one of the predefined coagulation conditions.

* * * * *